US007468277B2

(12) United States Patent
Goldman et al.

(10) Patent No.: US 7,468,277 B2
(45) Date of Patent: Dec. 23, 2008

(54) ENRICHED PREPARATION OF HUMAN FETAL MULTIPOTENTIAL NEURAL STEM CELLS

(75) Inventors: Steven A. Goldman, South Salem, NY (US); Hideyuki Okano, Osaka (JP)

(73) Assignees: Cornell Research Foundation, Inc., Ithaca, NY (US); Japan Science and Technology Corporation, Tokyo (JP)

(*) Notice: Subject to any disclaimer, the term of this patent is extended or adjusted under 35 U.S.C. 154(b) by 0 days.

(21) Appl. No.: 09/747,810

(22) Filed: Dec. 22, 2000

(65) Prior Publication Data

US 2002/0012903 A1 Jan. 31, 2002

Related U.S. Application Data

(60) Provisional application No. 60/173,003, filed on Dec. 23, 1999.

(51) Int. Cl.
*C12N 5/02* (2006.01)
*C12N 5/08* (2006.01)

(52) U.S. Cl. .................... 435/368; 435/366; 435/377; 435/378

(58) Field of Classification Search ............... 435/366, 435/377, 325, 368
See application file for complete search history.

(56) References Cited

U.S. PATENT DOCUMENTS

| 5,750,376 | A |   | 5/1998  | Weiss et al. ............ 435/69.52 |
| 5,753,506 | A | * | 5/1998  | Johe .......................... 435/377 |
| 5,851,832 | A | * | 12/1998 | Weiss et al. ................ 435/368 |
| 5,874,304 | A |   | 2/1999  | Zolotukhin et al. ......... 435/366 |
| 5,968,829 | A | * | 10/1999 | Carpenter .................. 435/467 |
| 6,245,564 | B1 |  | 6/2001  | Goldman et al. |

FOREIGN PATENT DOCUMENTS

| WO | WO 96/38541 | 12/1996 |
| WO | WO 97/07200 | 2/1997  |
| WO | WO 98/32879 | 7/1998  |
| WO | WO 99/29279 | 6/1999  |
| WO | WO 99/49014 | 9/1999  |
| WO | WO 00/23571 | 4/2000  |

OTHER PUBLICATIONS

Brustle et al. In vitro generated neural precursors participate in mammalian brain development. Proceed. Natl. Acad. Sci. Dec. 1997, vol. 94, pp. 14809-14814.*
Azizi et al. Engraftment and migration of human bone marrow stromal cells implanted int he brains of albino rats—similarities to astrocyte grafts. Proceed. Natl. Acad. Sci. Mar. 1998, vol. 95, pp. 3908-3913.*
Zimmerman, L. et al. Independent Regulatory Elements in the Nestin Gene Direct Transgene Expressin to Neural Stem Cells or Muscle Precursors. Neuron. Jan. 1994, vol. 12, pp. 11-24.*
Goldman, S. Glia as Neural Progenitor Cells. Trends in Neuroscience. Nov. 2003, vol. 26, No. 11, pp. 590-596.*
Keyoung et al. High-Yield Selection and Extraction of Two Promoter-Defined Phenotypes of Neural Stem Cells from the Fetal Human Brain. Nature Biotechnology. Sep. 2001, vol. 19, pp. 843-850.*
Salim et al. Identification of Proteomic Changes During Differentiation of Adult Mouse Subventricular Zone Progenitor Cells. Stem Cells Dev. 2007, vol. 16, pp. 1-23.*
Bonnert et al. Molecular Characterization of Adult Mouse Subventricular Zone Progenitor Cells During the Onset of Differentiation. Eur. J. Neurosci. 2006, vol. 24, No. 3, pp. 661-675.*
Weiss et al, "Is There A Neural Stem Cell in the Mammalian Forebrain?," *Trends in Neuroscience*, 19(9):387-393 (1996).
Goldman et al, "Neural Precursors and Neuronal Production in the Adult Mammalian Forebrain," *Annals of the New York Academy of Sciences*, 835:30-55 (1997).
Wang et al, "Isolation of Neuronal Precursors by Sorting Embryonic Forebrain Transfected with GFP Regulated by the Tα1 Tubulin Promoter," *Nature Biotechnology*, 16:196-201 (1998).
CytoTherapeutics, Inc., Press Release "CytoTherapeutics' Researchers First to Directly Isolate Normal Human Neural Stem Cells Key Step Toward Clinical Application of Proprietary Stem Cell Technology," *BW Healthwire* (Nov. 2, 1999).
Gloster et al., "The Tα1 α-Tubulin Promoter Specifies Gene Expression as a Function of Neuronal Growth and Regeneration in Transgenic Mice," *The Journal of Neuroscience* 14(12): 7319-7330 (1994).
Okano et al., "Musashil, a Universal Marker for CNS Stem Cells of Vertebrate Animals," Proceedings of the International Workshop, Tokyo, Japan (Feb. 25-26, 1999).
Zimmerman et al., "Independent Regulatory Elements in the Nestin Gene Direct Transgene Expression to Neural Stem Cells or Muscle Precursors," *Neuron* 12:11-24 (1994).
Roy et al., "Identification, Isolation, and Promoter-Defined Separation of Mitotic Oligodendrocyte Progenitor Cells From the Adult Human Subcortical White Matter," *The Journal of Neuroscience* 19:9986-9995 (1999).

(Continued)

*Primary Examiner*—Deborah Crouch
(74) *Attorney, Agent, or Firm*—Nixon Peabody LLP

(57) ABSTRACT

The present invention relates to a method of separating multipotential neural progenitor cells from a mixed population of cell types. This method includes selecting a promoter which functions selectively in the neural progenitor cells, introducing a nucleic acid molecule encoding a fluorescent protein under control of said promoter into all cell types of the mixed population of cell types, allowing only the neural progenitor cells, but not other cell types, within the mixed population to express said fluorescent protein, identifying cells of the mixed population of cell types that are fluorescent, which are restricted to the neural progenitor cells, and separating the fluorescent cells from the mixed population of cell types, wherein the separated cells are restricted to the neural progenitor cells. The present invention also relates to an isolated human musashi promoter and an enriched preparation of isolated multipotential neural progenitor cells.

8 Claims, 48 Drawing Sheets

(8 of 48 Drawing Sheet(s) Filed in Color)

OTHER PUBLICATIONS

Lothian et al., "An Evolutionarily Conserved Region in the Second Intron of the Human Nestin Gene Directs Gene Expression to CNS Progenitor Cells and to Early Neural Crest Cells," *Eur. Journal of Neuroscience* 9:452-462 (1997).

Sakakibara et al., "Mouse-Musashi-1, a Neural RNA-Binding Protein Highly Enriched in the Mammalian CNS Stem Cell," *Developmental Biology* 176:230-242 (1996).

Good et al., "The Human *Musashi Homolog 1 (MSI1)* Gene Encoding the Homologue of Musashi/Nrp-1, a Neural RNA-Binding Protein Putatively Expressed in CNS Stem Cells and Neural Progenitor Cells," *Genomics* 52:382-384 (1998).

Okano, Annual Meeting of Japanese Society for Neuroscience (Jul. 7, 1999) (abstracts and slides).

Gage et al., "Survival and Differentiation of Adult Neuronal Progenitor Cells Transplanted to the Adult Brain," *Proc. Natl. Acad. Sci. USA* 92:11879-11883 (1995).

Yaworsky et al., "Heterogeneity of Neural Progenitor Cells Revealed by Enhancers in the Nestin Gene," Developmental Biology 205:309-321 (1999).

Kawaguchi et al., "Concentration of Nerve Stem Cells Using Nestin-GFP Transgenic Mouse and Cell Sorter," 22nd Annual Meeting of the Molecular Biology Society of Japan, Program and Presentation Abstract, p. 697 (2P-1064) (1999).

Sawamoto et al., "Analysis of Dopamine Nerve Cell [Dopaminergin Neuron] Differentiation Process Using GFP and FACS," 22nd Annual Meeting of the Molecular Biology Society of Japan, Program and Presentation Abstract, p. 697 (2P-1067) (1999).

\* cited by examiner

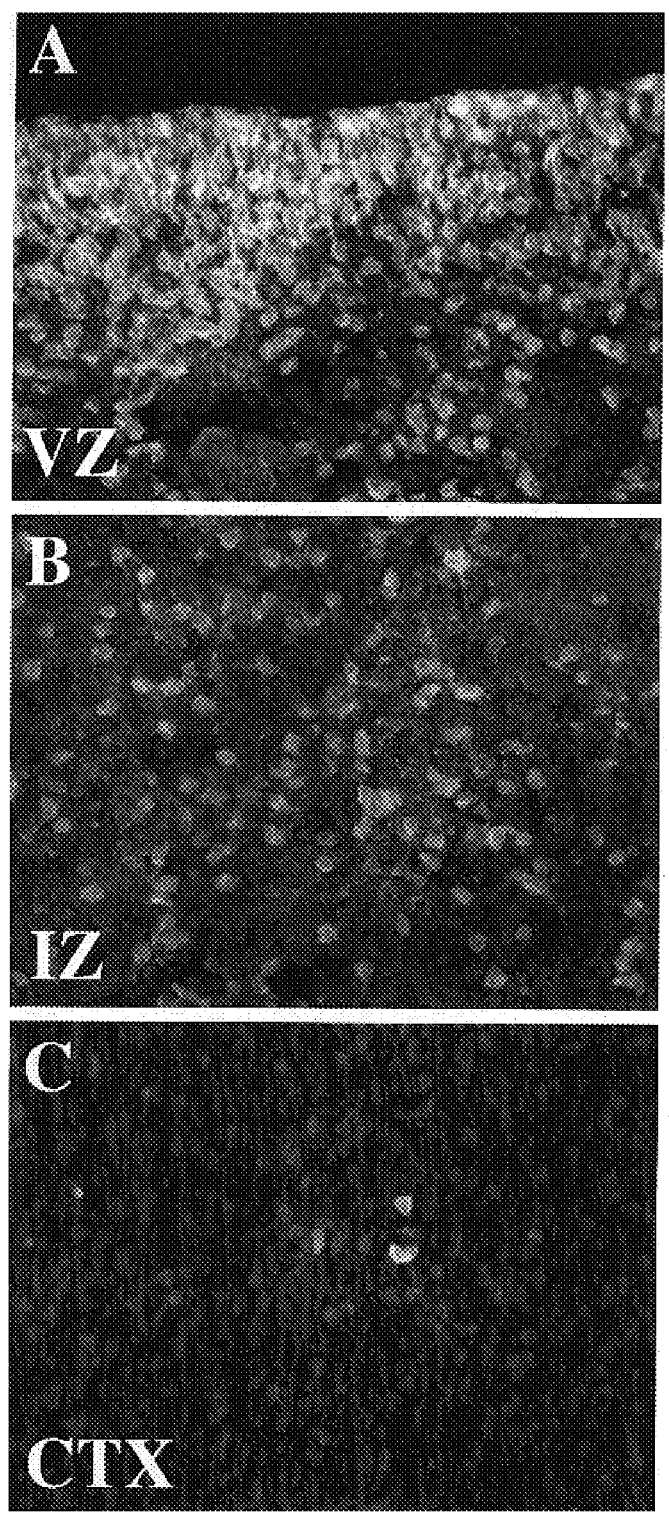
FIGURE 2 A-C

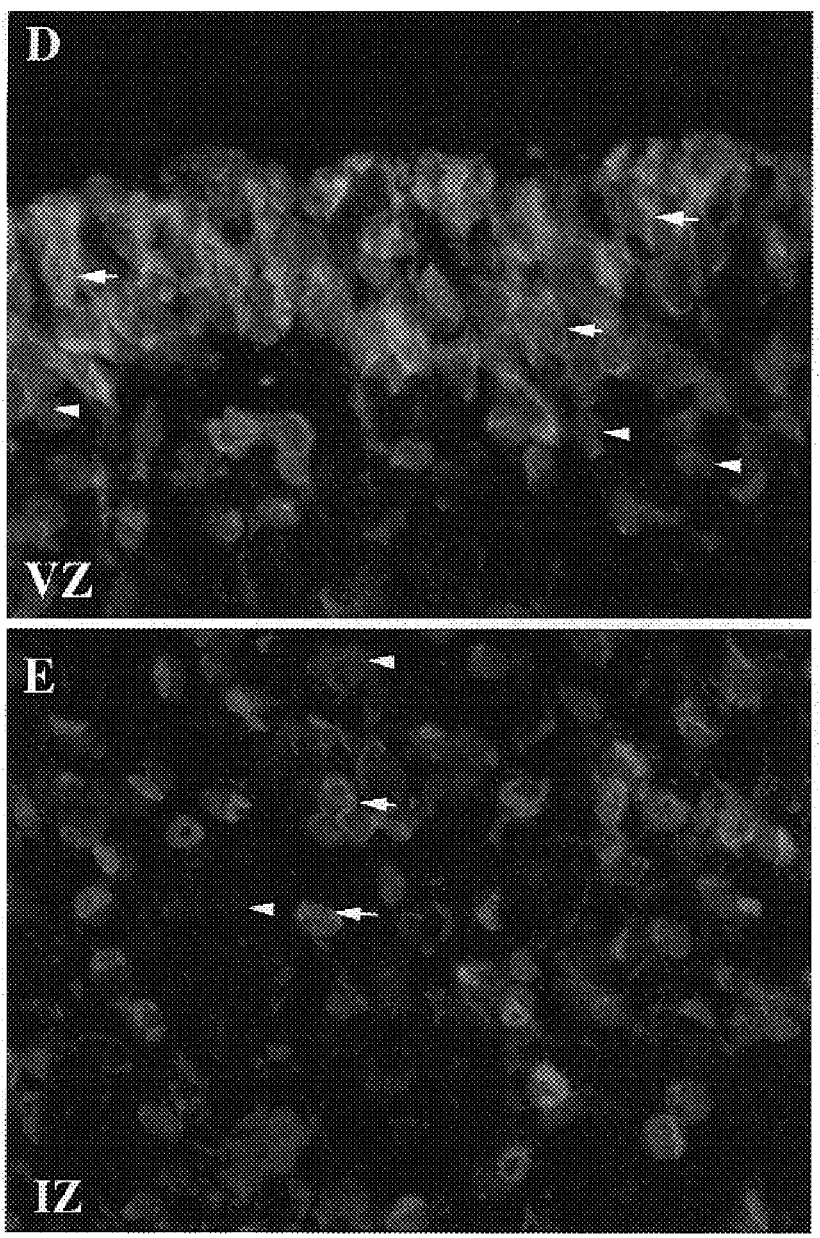
FIGURE 2 D-E

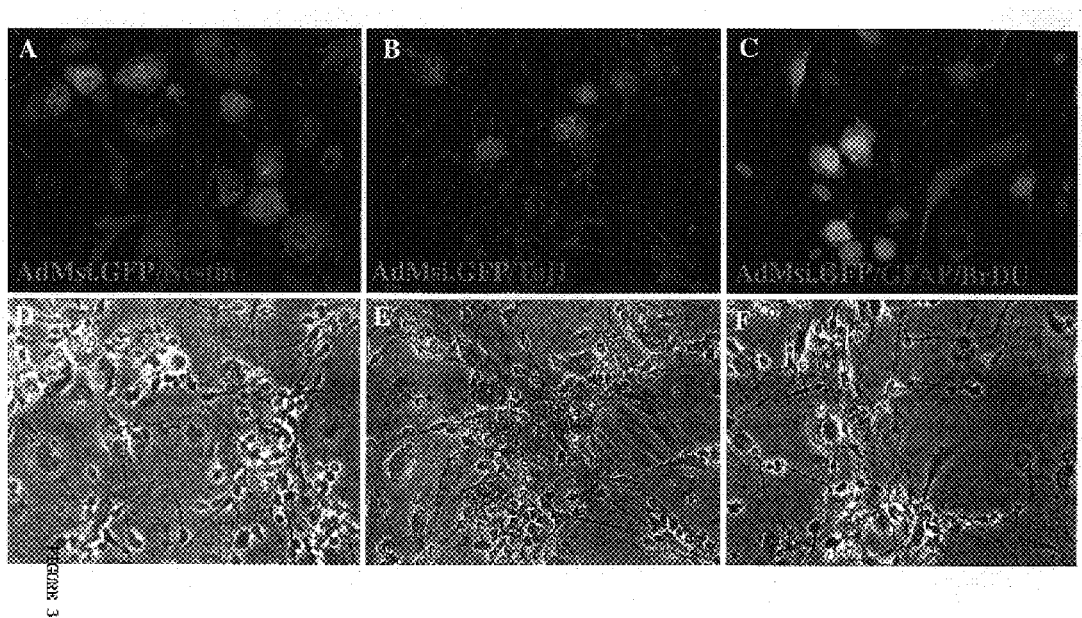

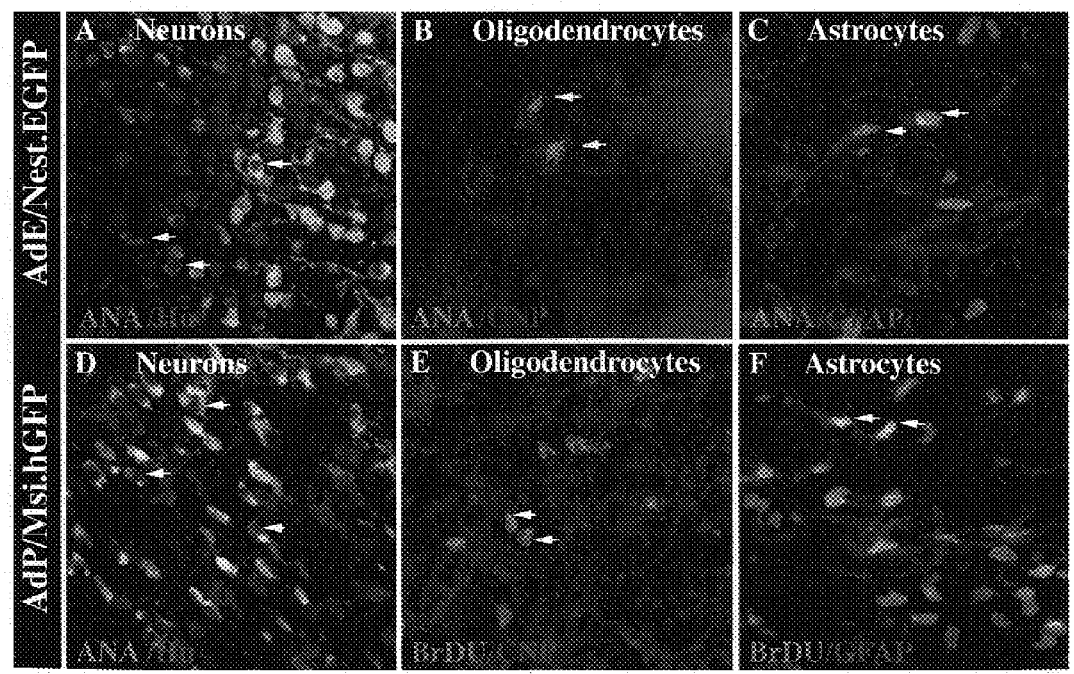

```
              10        20        30        40        50        60
       ...|....|....|....|....|....|    ...|....|....|....|....|....|
       gatccgcccgcctcagcctcccaaagtgct    gggattacaggcatgagtcacggctcccag  60
       tagtttatttttttgagacagagtctcactg   tgttgcccaggctggagagcagtggcagat 120
       cttggctcactgcaacctccgcctcccagg    ttcaagcaattctcctgtctcagcatcccg 180
       agtagctgggattacaggcacccgccacca    tgcccggccaagttttgtattttagtaga  240
       gatgaggtttcactatgttggccaggctgg    tctcaaactcctgacctcaggtgatgcacc 300
              310       320       330       340       350       360
       ...|....|....|....|....|....|    ...|....|....|....|....|....|
       cacctcagcctcccaaagtgctgggattac    aggcaggaaccacggcacctggcttctttt 360
       ctttttaattaagctttattggccaggcat    ggtggctcatgcctgtaatcctagcacttt 420
       gggaggccaaggcaggaggattgcttgagc    ccgggaggtcaagatcagcctgggcaacat 480
       agtgagacccacgtctctacaaaaaatacaa   aaagttagccaggcatggtggtgcacacct 540
       gtagtctcagctactcggaaggtggaggca    ggaggatcacaggagctcaggaggtcaatg 600
              610       620       630       640       650       660
       ...|....|....|....|....|....|    ...|....|....|....|....|....|
       ctgaataagccatgattgcgtcactgcact    ccagcctggacaacagagtgagaccctgtc 660
       ttttttttttttttttttttgagacgga     gtctcgctctgttgccgaggcttgagtgca 720
       gtggcgcgatctcggctcactgcaagctcc    gccttccggggttcacaccattctcctgcct 780
       cagcctcccgagtagctgggactacaggcg    cccgccaccacgcctgactaattttgtttt 840
       tgtattttagtagagatggggtttcaccg     tgttagccaggatggtctccatctcctgac 900
              910       920       930       940       950       960
       ...|....|....|....|....|....|    ...|....|....|....|....|....|
       cttgggatccgcccacctcagtctcccaaa    gtactgggattacaggcgtgagccaccatg  960
       cccagccgagaccctgtcttaataaacaaa    caagcaaacaaaaactttatttttggagc  1020
       agttttaggttcacagcaatattaagcaga    aggtacagagatttcctatatatctctctc 1080
       ctctccagacacaggcacagcttccccat     tatcaacgtaccctacatgagtggtgtttt 1140
       gtttgtttgtttgtttttgaggcagagttc    tgctcctgttgcccaggctggagtgcagtg 1200
```

FIGURE 11--A

```
         1210      1220      1230       1240      1250      1260
    ┌ⁱⁱⁱⁱ│ⁱⁱⁱⁱ│ⁱⁱⁱⁱ│ⁱⁱⁱⁱ│ⁱⁱⁱⁱ│ⁱⁱⁱⁱ│  ⁱⁱⁱⁱ│ⁱⁱⁱⁱ│ⁱⁱⁱⁱ│ⁱⁱⁱⁱ│ⁱⁱⁱⁱ│ⁱⁱⁱⁱ│
    gcgtgatctcggctcaccgcaacctccgac  tcccgggtttaagcgcttctcctgcctcag 1260
    cctcacaagtagctgggactacaggcacgt  gccaccacactcagctaattttttatatttt 1320
    ttcttttttttgttttttgagacagagtttc gctcttgtctcccaggctagagtgcaacgg 1380
    tgcgatctcagctccctgaaacctctgcct  cccaggttcaagcaattctcctgcctcagc 1440
    ctcccgagtagctgggattacaggcacttg  aacttctgacctcaggtgatccacctgcct 1500
         1510      1520      1530       1540      1550      1560
    ┌ⁱⁱⁱⁱ│ⁱⁱⁱⁱ│ⁱⁱⁱⁱ│ⁱⁱⁱⁱ│ⁱⁱⁱⁱ│ⁱⁱⁱⁱ│  ⁱⁱⁱⁱ│ⁱⁱⁱⁱ│ⁱⁱⁱⁱ│ⁱⁱⁱⁱ│ⁱⁱⁱⁱ│ⁱⁱⁱⁱ│
    cgacctcctaaagtgctgggattatacgca  tgagccaccgcgcccagcctgtattttag  1560
    tagagacagagtttcaccattttggccagg  atggtctctatcttctgacctcatgatccg 1620
    ccctccttggcctctcagagtgttgggatt  acaggcgtgagccaccgcacccagcttgta 1680
    tttttagtagagacggggtttcaccatttt  ggccaggatggtctctatcttctgatgtca 1740
    tgatgcgccgcctcggcctctcaaaatgt   tgggattacaggcgtgagccaccgcgccca 1800
         1810      1820      1830       1840      1850      1860
    ┌ⁱⁱⁱⁱ│ⁱⁱⁱⁱ│ⁱⁱⁱⁱ│ⁱⁱⁱⁱ│ⁱⁱⁱⁱ│ⁱⁱⁱⁱ│  ⁱⁱⁱⁱ│ⁱⁱⁱⁱ│ⁱⁱⁱⁱ│ⁱⁱⁱⁱ│ⁱⁱⁱⁱ│ⁱⁱⁱⁱ│
    gctatggctcactcttgatgctgcacattc  tgtgggtttggacagatgtataatgatatg 1860
    taccaactaactttttggagtctttccaaa  gcattcaactgcattcatagaaacatccgt 1920
    cttcttttccgactcatattttatcagttt  gtcctatataattataagatttaattacaa 1980
    gagtaactgatggccgggcgcagcggctca  tgcctgtaatcccagcgctttgggaggcg  2040
    aggcaggcagattacttgaagtcaggagtt  cgagaccagcctggccaacatggtgaaaca 2100
         2110      2120      2130       2140      2150      2160
    ┌ⁱⁱⁱⁱ│ⁱⁱⁱⁱ│ⁱⁱⁱⁱ│ⁱⁱⁱⁱ│ⁱⁱⁱⁱ│ⁱⁱⁱⁱ│  ⁱⁱⁱⁱ│ⁱⁱⁱⁱ│ⁱⁱⁱⁱ│ⁱⁱⁱⁱ│ⁱⁱⁱⁱ│ⁱⁱⁱⁱ│
    ttgtctctactaaaaatacaaaaattagcc  aggcatggtggtatgtgcccgtaatcccag 2160
    ctactccggaggctgaggcacaagaatcgc  ttgaagctgggaggtgaaggttgcagtgag 2220
    ccgagattatgccactgtactccacccttg  gcaacggagtgagactccgtctcaaaaaaa 2280
    ggagtaactgatgggagaaccaaccccect  gactcttgataaccacatggtcacatcttc 2340
    actcaacaggagttagtggcttgtcacact  agaaatgaacccaccagctgctgtgggcct 2400
         2410      2420      2430       2440      2450      2460
    ┌ⁱⁱⁱⁱ│ⁱⁱⁱⁱ│ⁱⁱⁱⁱ│ⁱⁱⁱⁱ│ⁱⁱⁱⁱ│ⁱⁱⁱⁱ│  ⁱⁱⁱⁱ│ⁱⁱⁱⁱ│ⁱⁱⁱⁱ│ⁱⁱⁱⁱ│ⁱⁱⁱⁱ│ⁱⁱⁱⁱ│
    cacattgttctagattttatagcaggcaaa  gcgagcatttgttaagctagtgagccaatt 2460
    ccagggatttttttttttttttttttggta  gagacggggtcttgccaagttgcccaggct 2520
    gcttctgaactcttggcctcaagcaatcct  cctaccttggcctctcaagtcgctgggatt 2580
    acaggaatgagccaccacgtctggcctccc  atgaattttttaatccagtgagttggtttat 2640
    ccagaaagctttccctatacaaccataaac  aaaaagtataacaaaaagtgatctcactgg 2700
```

FIGURE 11-B

```
         2710      2720      2730      2740      2750      2760
agtaattgaagtgaccagggttgattctgt ccttttactcatttatattttccagctttt 2760
ttgtacctttaatgtagatgaaagttggga tgtgtgtgtgtgtgtgttttgaagactt   2820
aattaagactatagggtcatatatgcctag ggctgaatgaactatactagacttcaaatt 2880
ccttgaatcgagcgtattgtaaaaggctgg acttgacataacatgcctaattgggataat 2940
gacagtggaaaaatcttggtattaggccat gtttctcaaagtgtgccccaggactggcag 3000
         3010      3020      3030      3040      3050      3060
cagcaacatcgcctgggaacttgctagaaa tgtaaattcttgggagccgccccagaactg 3060
ctgcatcagatactttgggatggggttcag aaatctgtgtttgaacaagccctccaaagg 3120
attctggtgttccctcaaattaacagatgg ctcacctcacaggtttaccactcagaggct 3180
gtgtgatctcagacaagtcactgcacctct ctgaacctatttcttctctgataagaataa 3240
tagcagacctaccttacagaatgattgtga aggttaaattaaataatatgtgtaggcaca 3300
         3310      3320      3330      3340      3350      3360
gtgcctgacacacagaagacactcactaaa tgttaggaaagctaatattattttaggaa  3360
ttcatgagtggcagctctaattagggtgaa aaacatgggagtagggtgtggtagctcaca 3420
cctgtaatcccagcactttgggagactgag gtgggagcatcacttgagtccaggagttgg 3480
agaccagtctggggaatatagtgaaactcc tgtctccacaaaaaatttttaaattagctgc 3540
atgtggtagtatgtgcctgtagttccagct actcaggaggctgagctgggaggatggctt 3600
         3610      3620      3630      3640      3650      3660
gagctcaggagattgaagccgtagtgagcc gtgattgtgccactgtactccagcttgggc 3660
aactgagtgagactttgtctcaaaggaaaa aaaaaggaagaaagaaaaacatttgggag   3720
aaaagaggaaaagatgttatggagtttaaa atatttctggtggggaacagtggctcatgc 3780
ctgtaatcacagcactctgggaggcctgag gcaggaggattgcttgagtccaggagttca 3840
agaccagcctgggcaacatagtaggacccc atctctataaaaataaataagtacctataa 3900
         3910      3920      3930      3940      3950      3960
tcccagtactttgggaggctgaggtgggcg aatcacttgaggtcaggagttcaagtccag 3960
cctggccaacattgtgaaaccccgtctcta ctaaaaatataaaaattacccgggtgtggt 4020
ggtgggcacctgtaatcccagctactcggg aggctgagacaggagaatcacttgaaccca 4080
ggaggtggagtctgcagtgagcagagatcg caccactgcactccagcctgggcaacagaa 4140
tgagactcagtctctaaataaataaattac aaactatttctgactaggcactttgacctt 4200
```

FIGURE 11-C

```
        4210      4220      4230       4240      4250      4260
    ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
    attatgtaccttcaccctccgaataaacat  gttaaagtagaagcaggtatcattatattc  4260
    cctgcccatttcacagatatggagactgag  ggttggtggggctgaatgatagctaagaag  4320
    tagcagagctgggacctaaccatatccatg  tgccccacctcactctcagcctcaaacaga  4380
    tgcaggcagattgcccactcaccagagcct  ccccccttccccaaaccatctgccctctg   4440
    attgttttcttggggctctagaagtcaggc  ctttcagctcatctttactgcacagggatt  4500
        4510      4520      4530      4540      4550      4560
    ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
    tctccattggccggtttctgctgcctgaga  cccttgcccagccccagccaacaccagcat  4560
    gattcactttctgttttttgagatggagt   ttccctctcgttgcccaggctggagtgcag  4620
    tgacgtaatctcggctcactgcaacctctg  cctccagattcaagcaattctcctacctc   4680
    agcctcccaaatagctgggactacaggagt  gcaccaccacacctggctaatttttggtact 4740
    tttagtagagacagggtttcgccatgttgt  ccaggctggtctccaactcctgacctcagg  4800
        4810      4820      4830      4840      4850      4860
    ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
    tgatgcaccctcctcggtctcccaaagtgc  tgggattacaggtgtgagccaccgcgccca   4860
    gccatgattcacatttgaacctgagaccag  agctcataaatgcattaattcattaatttc   4920
    tcaaacattctacatgctatgggataggta  cttggggtacagagaggagcaaaatggaca   4980
    ttggccctactgcaaagaacctgaatattc  acgtggagtatttcccatcactttctaggc   5040
    ctagccttgattttgctgaaccggggcca   aggcagaggcacaggtgcctccacagagca   5100
        5110      5120      5130      5140      5150      5160
    ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
    gaaccagacaaatattgtacactatagtca  gtgcagggatgggaacacaacctggctctg   5160
    taagaggccagaagaggcccttgatcaatc  tgcgggtggaagggaatccatgaagacttc   5220
    ctgcaggtggtgacctctgaggctgattag  gaggtgtttgccatagtgtttcatcatttt   5280
    ctcatttatagatggcaaaatgagtccag   agagaatgacttagcccatgtattcaatca   5340
    attgagcaaacatttccctaatatctacat  tccccattattgagccctgagcctggggat   5400
        5410      5420      5430      5440      5450      5460
    ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
    acagaggtgaataaggttaacaggcctgct  agagggaatggtatagagaggcctcaagta   5460
    tccaggatacctcaccaatcactgcccatt  ggcctctgttttttgtatgtatttattt     5520
    tattattattattttgtaaattttgagaca  tggtctcactccgttgtccaggctggagtg  5580
    cagtggtggaaatataactcactgcagcct  caattccctagcctcaagcaatcctcccat   5640
    ctcagcctccccactagcaaggactacagg  catgtgccactgtgcccagttaatttttttt 5700
```

FIGURE 11-D

```
        5710      5720      5730      5740      5750      5760
ttttttttttggtagagataggatcttgcca  tgttgcccaggctggtcttgaactcctgag  5760
atcaagagctcctcccacctcggcttccaa   agtgctgggattacagacgtgagccaccac  5820
acctggcctatttatttacctttttaaa    agtcaggattggccgggcacggtggctcac  5880
acctgtaatcccagtactctgggaggccga   ggcaggtgaatcacctgaggtcaggagatt  5940
gagaccagcctgcccaatatggcaaaaccc   catctctactaaaaatacaaaaattagct   6000
        6010      6020      6030      6040      6050      6060
gggcatggtggtgcacacctgtagtcccag   ctactcaggaggctgaggtaggagaattgc  6060
ttgaacctgggaggtggaggttgtagtgag   ctcagaccgtgccactgtagtctagcctgg  6120
gcaacagagcgagactctttctcaaaaata   aatacataaataaaattaaaaatgataaaa  6180
gtcatggttattgcagtatacatacagtaa   aattctccttttagtacatatgtggcaa   6240
atgcatagtcctgtaatcatcatcacaatc   aagacacaaagacacaggtcatcatttgaa 6300
        6310      6320      6330      6340      6350      6360
tctttttttttttttttgagtcggaacctt   gccctttaccgaggctggagtgcagtggc  6360
gtgatcttggctcactgcaacctctgcttc   ccaggttcaagcaattatcctgcctcagcc 6420
tccggagtagcagggaccacaggcacgcac   caccacgctcagctaattttttgtatttta 6480
gtggagacagggtttcaccatgttggacag   actggtcttgaactcctgacctcaggtgat 6540
ccacccacctcagcctcccaaagtgctggg   attataggtgtaagccaccgcgcccggccc 6600
        6610      6620      6630      6640      6650      6660
atcatttgaatcttatgttcatcccacttc   ctgagtccaagccttccccttaattcactg 6660
tgttatcttgggcaactcttgccctctttg   aacctcagtttcttcatctttaaaatggga 6720
accataaaaccaccccttacaggattgctgt  gaggatggttgcctggcacacagtaagcgc 6780
tcaattaacaccagcttttattcacactcc   ttcccttttctagcccttttcaaactccccc 6840
tctccctctggtctctctccttctgggtct   gtctctccctctcacagacacacacacaaa 6900
        6910      6920      6930      6940      6950      6960
cacactccctctgggacacacacacacact   ctgggacacacacagggacacacacacaca 6960
cacactccctctggggacagacacacaca    cacacacacacacacatttgaagcctctt  7020
gtttcccagagaggttttatttataggctg   tgcctcattgtgaatgtgaaaaggagaaag 7080
cccaggccctccgtagacctttcatgtgta   aatcagccgggcctggagcacggggtcac  7140
caggaggaggatttcactcttaattactcc   tagagaaagcgggcgggaaggaggcctctc 7200
```

FIGURE 11-E

```
        7210      7220      7230      7240      7250      7260
tgggagcccagggcctcgcctggcgccggg ccoctcgctcccaggctggggagcgctgg 7260
ctctccagggccgggatcaggctagagctg gggccaacacttcctgggtctggccttgat 7320
ttctgctgaacctgagccaaggcagaggcg caggtgcctccagggagcagggccccaagt 7380
aggtttctttgagggcaagttgtttggaca cagaaagagggcacacagcttgacagggtt 7440
ggagatagcaagggtgatctgctgaagtgc caggcaggggtaattaaacaaaatttttaa 7500
        7510      7520      7530      7540      7550      7560
ggttttaaaattcatttctgatgtaaaaat cacacactctattatagaaaaatgtttgaa 7560
aagattcctatccaggccgttaacattgtt tatttcgaggggtaagtttgtttgtttatt 7620
tattttgagacggagtctcactctgtcat ccaggctggagtgcagtggggcaatttcag 7680
cttcctgcaacctctgcctcccgggttcaa gtgattctcgtgtcctcagcctcccgagta 7740
ggtgggataacaggtgcgcgccaccatgcc tggctaattttgtatttttagtagagagg 7800
        7810      7820      7830      7840      7850      7860
gggtttcaccctgttggccaggctggtctc acctcaggtgttccgcccacctcggcctcc 7860
caagtgctgggattacaggtgtgagctact gtgcctggccagcgggtaaatttagaggta 7920
aagaaagggacattattaacatttttatac atttttattttaaacttattacaatgac 7980
tatgtattgcttttaattaaaaagcacaa cgttattttcatagtatccatggtactgt 8040
tttctgattacagaaaagaaattaatattt gatataagacattgagaaaataaagtataa 8100
        8110      8120      8130      8140      8150      8160
aaactatctgtggctccatgaaagaatatc atttttttcttccttgattctgcattaaa 8160
ggaaatcaaagaaaaacactttaatatt aagtatatggccatagatgatttatttctt 8220
ggctaagtagttcatttttatttatgttc attttgcatacttatactgcacaaacactt 8280
tgggtacaacttaacacactgaggttttct tttttttcttttattcttttatttattt 8340
atttattttgagtcggggtgcagtggtgtg accttggctcactgcctcctctgcctcctg 8400
        8410      8420      8430      8440      8450      8460
ggttcaagcgattctcctgcctcaacctcc tgagtagctgggattacaagcacgcgccac 8460
cacacctggctaattttttgtatttttagta gagacggggtttcaccatgttggccacgct 8520
ggtctcgaactcctgacctggtgatccacc cgccttagcctcccaaagtgctgctgggat 8580
cacaggcgtgagccatggcatctggcctca cactgaggttttttcttccattcatcttt 8640
tctcttcttgtgctttatatacagtcgtca ttcagtgtccctgggggattagttctggca 8700
```

FIGURE 11-F

```
       8710      8720      8730      8740      8750      8760
   ╷┅┅┅╵┅┅┅┅╵┅┅┅┅╵┅┅┅┅╵┅┅┅┅╵  ┅┅┅┅╵┅┅┅┅╵┅┅┅┅╵┅┅┅┅╵┅┅┅┅╵
   cctccctcagataccaaaatccacagatgt  tcaagtccctgatatataaaatggcatagtat  8760
   ttgcatattatctatgcataccctcctgta  tactctaagtcatttctagattacttatga   8820
   tccctaatacaatgtcaatgcccggtaaat  cattgttatactgtgttttttagggaataa   8880
   tgataaggaaaaaagtctgtctatgttcaa  tacagatgcagggttttttcccaaatattt   8940
   tccatcaaggttggtggagtccagggatgt  ggaatgaataaatacagaggaccacctata   9000
       9010      9020      9030      9040      9050      9060
   ╷┅┅┅╵┅┅┅┅╵┅┅┅┅╵┅┅┅┅╵┅┅┅┅╵  ┅┅┅┅╵┅┅┅┅╵┅┅┅┅╵┅┅┅┅╵┅┅┅┅╵
   tatatgtatgttactggatggcattatttt  gaaatatgaaatacacaagcccttggggtc   9060
   cagcaattccacatctaaaattctattcat  gtgagtaggagtaggtaaatagtagaaaca   9120
   aatttgttcattttgaaggtgtttataaaa  gcaaaggctagcaacaaacttgatggtcat   9180
   cagtaggaaattaagtaagtaaatcatcat  gtaactttacagtgaaatgttttgtagtca   9240
   ttataagagtatatcggctgggcgtggtgg  ctcaggcctgtaatcccagcactttgggaa   9300
       9310      9320      9330      9340      9350      9360
   ╷┅┅┅╵┅┅┅┅╵┅┅┅┅╵┅┅┅┅╵┅┅┅┅╵  ┅┅┅┅╵┅┅┅┅╵┅┅┅┅╵┅┅┅┅╵┅┅┅┅╵
   gccgaggcgggtggatcacgaggtcaggag  ttcaggatcagcctagccaatatggtgaaa   9360
   ccctgcctctactaaaaatacaaaaattag  ccaggcgtggtggtgcgcacctgtaatccc   9420
   agctactagggaggctgaggcaggagaatc  actcgaacccgggaggcagaggttgcagtg   9480
   agccaagatcgtgccactgcactccagcct  gggcgacagagcaaggctccatctcaaaaa   9540
   aaaaaaaaaaaaagaaagaaagaaaaagaa  aaaaagagtatatcaggccaggtgcagcga   9600
       9610      9620      9630      9640      9650      9660
   ╷┅┅┅╵┅┅┅┅╵┅┅┅┅╵┅┅┅┅╵┅┅┅┅╵  ┅┅┅┅╵┅┅┅┅╵┅┅┅┅╵┅┅┅┅╵┅┅┅┅╵
   ctcacgcctgtaatcccagccatttgggag  gctgaggcgggtgtatcacttgaggccagg   9660
   agttggagaccagcctggccaacatagtga  aaccctgtctctactaaaaatacaaaaatt   9720
   agccgggcatggtggccctcacccataatc  ccagttactcggggaggctgaggcatgagaa  9780
   ttgcttgaatctgggaggcagaggttgcag  tgagccaagatcacgtcactgcattccagc   9840
   ctgggtgacagtgagactccgtctcaaaaa  aaaaaaaaaaagagtatatcatacatgcaa   9900
       9910      9920      9930      9940      9950      9960
   ╷┅┅┅╵┅┅┅┅╵┅┅┅┅╵┅┅┅┅╵┅┅┅┅╵  ┅┅┅┅╵┅┅┅┅╵┅┅┅┅╵┅┅┅┅╵┅┅┅┅╵
   agatatccaaaaatctgtactatagtaaat  aactaagcaagttccaaaatcatttggatt   9960
   gtgtgattctatatctattttttgttttgtt  ttgtttgagacggtctcactctgttgccca  10020
   gactagagtgcaatggcgtgattatacctc  actgcagcctcgacctcttgggctcaagtg  10080
   atcctcccatctcagcctcccaagtagcct  atatctatttttaaaatataataatcata  10140
   tctaagtatataggcatggaacattttttgg  aaggatatacatgaaattggtaacagttac  10200
```

FIGURE 11-G

```
           10210      10220      10230      10240      10250      10260
atttagggaaggagtctaaggggtaaagaa cttttactttttcatcttatacctttgtgt 10260
actgacgcatttttttcttttaatgtgagc acatgttacatttgtaattttttaaaaacta 10320
gctaatagaaatgtggtttagggctggatg cagtggctcatgcctgtaatccctacacat 10380
tgggaggctgaggtgggtggatcacctaag gtcaggagttcaggacaagcctggccaaca 10440
tggtgaaactctatctctactaaaaataca aaaattagccgggggtggtggcaggcgcct 10500
           10510      10520      10530      10540      10550      10560
gtcatcccagctgcttgggaggctgaggca ggagaattgtttgaacccggaaggcagagg 10560
ttgcagtgagcagagatcatgccactgcat atcagcctgggtgacagagcaagactctgt 10620
ctcaaaaacaaaacaaaacaaaagaaatgt ggttttgctatatataattctaatatatat 10680
ttattaaagaaaatacaggccgggcacgga ggctcacacctgtaatccaacatggtgaaa 10740
ccctgtctctactaaaaatataaaaattag ctgggcatggtgaggcgcacctgtagtccc 10800
           10810      10820      10830      10840      10850      10860
agctactcaggaggctgaggcaggagaatc gcttgaactttggaggcggaggttgcagtg 10860
agcagagatctcgccactgcactccagttt ggcaacagagcaagactccatctcaaaaaa 10920
aaaccaaaaaaacaaaaaatgtccattaaa taaacacagtttcttaaagaaatagtgttg 10980
attaaataaaatataatcccccatattatt caaggcaaccatattaacattttaatttat 11040
ttccttctagttttctctatatatatattt atacattttaatattttacaaattttttt 11100
           11110      11120      11130      11140      11150      11160
ttgagacagagttttgccctgttgcccagg ctggagtgcagtggtgcagtcttagctcac 11160
tgcaacctctgcctcctggggttcaagtgat tctcttacctcagcctctggagcagctggg 11220
actacaggcacacgccaccatgcccaacta agttttgtgtttttagtagagacggagttt 11280
cactatattgggtaggctggtcttgaactc ctgatctcatgatccacccaccttggcctc 11340
tcaaagtgctgggattacgggcgtcagcca ccgcaccaggaccttttttttttttttttt 11400
           11410      11420      11430      11440      11450      11460
ttttttttgagacaaagtcttgctctgtca cccaggctggagtgcagtggcatgatcttg 11460
gctcaccacaacctcttcctcccgggttca agcaattctcttgcctcagcctcccaagta 11520
gctgggactataggcacacaccaccatgcc cagctaatttttatattttagtagagaca 11580
ggggtttcaccatgttagccaggatggtct cgatctctgacctcgtgatccaccgcct 11640
cggcctcccaaagtgctgggattacaggca tgagacaccgtgcccggcgacacctacaa 11700
```

FIGURE 11-H

```
           11710     11720     11730     11740     11750     11760
       |....|....|....|....|....|....|    |....|....|....|....|....|....|
       ttctttaaactcccaacaactcaaaggaac  agatattattattactcccatttgcagatg  11760
       ggtaagtagaggcacagaaagatgagagga  tttgcccaaagacttggctggtatttggca  11820
       gaaccaggattcaaacccaacaggcaagag  cagagttgtacacttgacctagctattctg  11880
       ctattctgcctaatgaggttcttttttctt  ttcttttcttttttttaaattttttttttat  11940
       tttttgagacagagtctcactctgttgccc  aggctggaatgcagtggtgcgatctcggct  12000
           12010     12020     12030     12040     12050     12060
       |....|....|....|....|....|....|    |....|....|....|....|....|....|
       cactgcaacctccagctcctgagttcaagc  aattctcctgcctcagcctcttgagtagct  12060
       gggattacaggtgtgcaccaccacacccgg  ctaattttgtattttagtagagatgggg    12120
       tttcaccatgttggccaggctggtctcaaa  ctcctgacctcaagtgatctgcctgccttg  12180
       gcctcccaaagtgctgggattaccaggcgt  gagccaccgcgcccggccctaatggggttc  12240
       tgacaaaatccaggaattcagtgcagggtg  ggcggacctgtgagtgtgtgagtgagggat  12300
           12310     12320     12330     12340     12350     12360
       |....|....|....|....|....|....|    |....|....|....|....|....|....|
       atgcgtacttgtggagccacagatatgcac  atgtgtactcacgtgttcaccgtgagtctg  12360
       acggcgtgggtgcatgcatgtgttaaccag  tgctctgctgacatcatggtgcccaagcac  12420
       gtagagatgtatgtgcccatggattcccct  gtccaggctcccacaggacctatctccttg  12480
       gtttctccaccttccccttggtacacagga  ggcatgagtgtccaggaggggccagggttt  12540
       ggattccaaagcccagctgccacttcctta  ttcccaccatgtctcccaagagtagttagg  12600
           12610     12620     12630     12640     12650     12660
       |....|....|....|....|....|....|    |....|....|....|....|....|....|
       gtctggactcttaaaacatcaagctgggtg  ggaggcggtggctcacacccttaatcccag  12660
       cactttgggaggccgaggtgggtggatcac  ttaaggtcaggagttcgggaccaacctggc  12720
       caacaaggcaaaactccgtctctactaaaa  atacaaaaattagctgggcatggtggcaca  12780
       cgcctgtggtcccagctacttgggaggctg  aggcaggagaattgcttgaacccggaggc   12840
       ggaggttgcagtgagctgacatcatgccat  tgcactctagtatgggcaacagagccagat  12900
           12910     12920     12930     12940     12950     12960
       |....|....|....|....|....|....|    |....|....|....|....|....|....|
       tctgtctcaaacaaacaaaaaaacctcatc  aagctggccaggcacaatggcttacacttg  12960
       taatcccagcactttgagaggctgaggcag  gaggatcacttaagcccaaaagtttgaggc  13020
       tgcagtgagctatgatcacaccactacact  ctagccggggtgacagagcaagaccttgtc  13080
       tctataaaaaataacaaaataaaacattag  ctcttgcagggcgcggtggctcacgcctgt  13140
       aatcccagcactttgggaggctgaggcagg  cggatcacaaggtcaggatttggagaccag  13200
```

FIGURE 11-I

```
              13210     13220     13230     13240     13250     13260
    cattgccagcatggtgaaacccgtctcta ctaaaattacaaaaaattagccgggcatgg 13260
    tggcacacctgtgatcccagttactcagga ggctgaggcaggagaattgcttgaacccag 13320
    cagacagaggttgcagtaggccaagatcac gccattgcactccagtctgggtgacagagc 13380
    gagattccatctcaaaaaaaaaaaaaatca gctctttatgaagtagagttggcatatggg 13440
    ccagggaagtcggagaacaatgtggttttc cccaggaggcagcacccacagcttttagcc 13500
              13510     13520     13530     13540     13550     13560
    ctatctggcctccactgtgggtggctgata tctactaccacagtggaggccatatggtcc 13560
    tggttaagagtaagctgtaaagtgaaactg ttgggttcaaatcccagctttgccacttag 13620
    ctgtgtgatttcagcaacttactctcggat cctctacttccatccctgtgaagtgggagt 13680
    attataatagcaacaactttgaagggtttg gtattttaaatttatttttatttttattt 13740
    tatttattttttaatagagacagggtctc cctatgttgcctaggctggtctcgagcccc 13800
              13810     13820     13830     13840     13850     13860
    tgggctcaagtgatcctgccacctcggcct cccaaagtattgggattacaggtgtgagcc 13860
    acagtggctggccccctgaaggatttgtcg taaggctgaaataatgctgagctcaaactc 13920
    agtgttcaataaatgttagttttattacta ttttgaacccatactagacaagtaaagggc 13980
    agagaaatgtgcttttccagaagacagtgc ctttgtcatacgggtaaattatccaacctt 14040
    gtgaaacaggtattatttttcttttctttt tttgagacagagtttcactcttgtcgccca 14100
              14110     14120     14130     14140     14150     14160
    ggctggagtgcaatggcatgatcttgcctc actgcaacctacgcctcccaggttcaagcg 14160
    agtctcctgcctcagcctcccaagtagctg ggattacaggtgtgtgccaccatgcccagt 14220
    taattttgtatttttagtagagacggaga ttcaccatgttgtagacatgtttgtatgtt 14280
    tagtagagacggagtttcactggtctcgaa ctcctgacctcaggcaatccacccacctca 14340
    gcctcccaaagtgctgggattacaggcata agccaccacgcttggccccatttattta 14400
              14410     14420     14430     14440     14450     14460
    ttttttgttttgttttaaagaaatagagat gggatctcgctatgttgcccaggctagtct 14460
    caaagtcctgggctcaagtgatcctcctgc ctcagcctcccaaagtgctggaattacagg 14520
    tgtgcaccactgcacccagtctgtgcccat tttatggatgaggagactgaggctcagcag 14580
    tatgcagtaacttgtcccaggtcacagagc aagtaagtaacaaaaccagatttcacttgc 14640
    tggtctgcctccaattccagggctctttct gccacccaacagctgccttgttgtttggcc 14700
```

FIGURE 11-J

```
       14710     14720     14730     14740     14750     14760
tagaagcttcatcctgtaagctctgatttg cgcagattatctgccacctacatgtctttc 14760
tctcatgttgcctactcacaagagaatatg tagggatttgcaggtggtcagattttatgg 14820
gaaaaaaaatagacatttccacacagaaaa gaaactccagggagacagttgagacagtta 14880
ggcagggagttcttggaggaaaatgggagg ttcaaaaggcaattaatgctactgtctgaa 14940
actgtaaacagatagttactggctctgaca ccaccagcacacagacaaaaggcagacaga 15000
       15010     15020     15030     15040     15050     15060
aacagcgcaccacaaggaagctgggcatag actacgcccagggtggaaattaaatgtttt 15060
cctgaaagcagaaaggaaaaccatagttaa agccaatccatgactctaagtctatgactc 15120
catgacagcataagtccagtgagtaaaggc ccttcatttgcacctaggcgttgttatgaa 15180
tcttaaggccttactccacattctctcttg acctaagtttgtaaaacaaaagtaataatt 15240
agaagtgactcttcagcatatactgttatt ttaatcaaagatagatatacacacacacta 15300
       15310     15320     15330     15340     15350     15360
tatatgtgtgtgtatatatgtatatagagg atctatagtatatatcctctatatacatat 15360
atattataaatatatatgtatatatattta tctatatatacgtatatgtgtatatatgta 15420
tatatgtatatagagtatatatatttatac tctatatacacatatacatatatatacact 15480
atatatatgtgtgtgtgtgtgtgtgtgtgt atatatatataacagacatgagccaccaca 15540
cctggccccatttttgttttatttcttgttt tattttcaataaatagagatgggctctcac 15600
       15610     15620     15630     15640     15650     15660
tatgttgcccaagctggcctcaaactcctg ggctcaagtgatcctcctccctcagcctcc 15660
caaagtgctgaaattacaggtgtgcaccac catatatatatatggagagagagaaagatg 15720
tgtggctgggcacagtggctcacatctgta ctttggggaggccgaggtgggaggatcgctt 15780
gaggtcaggtgttgaagatcagcctgggca acatagcgagaccctgtctctacaaaacaa 15840
aacaaaacaaatatacatatattgtttgtt ttgtttcgtagatacggagtctcactatgt 15900
       15910     15920     15930     15940     15950     15960
cactcaggctggagtgcggtggcgtgatct tggctcactgcaacctccaccttccgggtt 15960
caagcgattctcttgcctcagcctcctgag tagctgggactacaggctcacgccaccgca 16020
cctagctaattttttgtatttttagtagagt cagggtttcaccatattggccaggctggtc 16080
tcgaactactgacctcatgatccacccatc tcagcctcccaaagtgctgggattacagac 16140
gtgagccaccgcgtctggcccatatatagc acacgcctgtaatcctataatcccagcact 16200
```

FIGURE 11-K

```
         16210      16220      16230      16240      16250      16260
     ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
     ccgggaggctgaggcaggtagatcacctga ggtcaggtgttcgagaccagcctgaccaat 16260
     atggtgaaacccatctctactagaaatac aaaaattagctgggcgtgatgctgtgccct 16320
     gtagtctcagctactcaggaggctggacgg gagaattgcttgaacccaggagatggaggt 16380
     ttcagtgagctgagatcggccactgaactg tggcctgggcaacagagcaagactccgtct 16440
     caaaaaaaaaaaaaaaatatatatatatat atatatatgtacatatatatagacagagag 16500
         16510      16520      16530      16540      16550      16560
     ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
     agagagagagagcacacacattggcacatt gttggcaagtttcctcagcattcctagttg 16560
     taaatgacagaaaactcactgatgcaaaca aagcaaagaatcataataattattattatt 16620
     tactgatttacaactggatcaaggagttca aagattccaattcatgtccttgccatgtct 16680
     tgactctgctttcttctgtggtttcaatct cagacagacacgctcctccccagggtgaca 16740
     agaaggctctcaggagctccacccatgctt tttcctgttggttaaaaaacagtgcctctc 16800
         16810      16820      16830      16840      16850      16860
     ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
     tccagcaaaaatctcaagtctcccactgat tggctcccattgggtcatatgcctgttctt 16860
     caaccaatcctgtggccaggctggatccca gggccaaccctggaggcacaggtgggcaga 16920
     gtaagttccatccaagatacaggaactgat attgggagagggagagttccccagggaaaa 16980
     ctgggggggctgtttccagaagacacatgtt caccatctggtagttgctgcctctctgtta 17040
     accaaatttaatgagaagctgtcatcagga gtaattttcttgtattttttactagagctgg 17100
         17110      17120      17130      17140      17150      17160
     ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
     ggcttcaccatgttgcccaggctggtctcc aactcctaagctgaggcaactgcccacctc 17160
     ggcttcctaaagtgctgggattacaggcat ggccaccacgcctggccatgtttatttctt 17220
     atcttcatctcacttcatcaatgggcaaat tgacagagaggttaaggaattggcccaagt 17280
     ttatacagagagtaaggagtggagccaggg catcctttccaaattctgtgctttagtttc 17340
     tccaggaactacagttagagctgatctatc tctcagaattgccagctccgtgccaatgag 17400
         17410      17420      17430      17440      17450      17460
     ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
     gaagccctgagccttctaaaggaccacctt gcaaggttaaccaatgtgggatggcagata 17460
     tcatccacacactcatgagggtttatcctg gagcagtgcctggacactgagaggtgtgac 17520
     aacaaggcaagtctgatccaaggaccattg tggactcaggagctgagattcctcggtagc 17580
     cctgcttccctacccacaggagtggaggag aaagagtgcaacgcacagagaagtgccaag 17640
     attgagcccctaacctgccgctaaccagct gttatgtgtcttgaataaactcctttaaga 17700
```

FIGURE 11-L

```
         17710     17720     17730     17740     17750     17760
    ┴┴┴┴┴┴┴┴┴┴┴┴┴┴┴┴┴┴┴┴┴┴┴┴┴┴┴┴┴┴┴┴ ┴┴┴┴┴┴┴┴┴┴┴┴┴┴┴┴┴┴┴┴┴┴┴┴┴┴┴┴┴┴┴┴
    tctctgtggccaggcacggtggctcacgcc tgtaatcccagcactttgggaggccaaagt 17760
    gggcggatcacctgaggtcaggagtttgag accagcctggccaacatggcaaaacctcgt 17820
    ctctactagaaatacaaaaattagccaggt gtggtggtgcttgcctgtaatcccagctac 17880
    ttgggaggctgaggcaagagaatcgcttga acccaggaggtggaggttgcagtgagccaa 17940
    gattgcgccattgcactccagcctgggcaa caagagcgaaactccatctcaaaaaaacaa 18000
         18010     18020     18030     18040     18050     18060
    ┴┴┴┴┴┴┴┴┴┴┴┴┴┴┴┴┴┴┴┴┴┴┴┴┴┴┴┴┴┴┴┴ ┴┴┴┴┴┴┴┴┴┴┴┴┴┴┴┴┴┴┴┴┴┴┴┴┴┴┴┴┴┴┴┴
    acaagatctttgtttctacatccataaaat gggcataataacaccttcctcagaggttag 18060
    cgaggattctattaaatactgcaggcaaaa taatacctgcttggctgggtgcggtggctc 18120
    atgcctgtaatcccagcacttcgggaggct gaggcaggaggatcgcttgagctcaggagt 18180
    tcaagatcaacctgggcaacatagaaagac ctcatctctacaaaaaatatgaaaaattag 18240
    ctgggtgtggtggcgtgcacctgtagtccc aggtactcaggaggccgagatgggaggatc 18300
         18310     18320     18330     18340     18350     18360
    ┴┴┴┴┴┴┴┴┴┴┴┴┴┴┴┴┴┴┴┴┴┴┴┴┴┴┴┴┴┴┴┴ ┴┴┴┴┴┴┴┴┴┴┴┴┴┴┴┴┴┴┴┴┴┴┴┴┴┴┴┴┴┴┴┴
    tcttgagccagggaagtcaaggctgcattg agccgagatcacgccagcccgggcaacaga 18360
    gcaagatcctgtctgtaatagtaacaataa caataataattcttgcttgtcacccagctg 18420
    gtctccatgaggttagttgtctccttttca tattatccccttctccatcccccagactt 18480
    agcaagagcaaggcaagcggagaaaggaaa gcatcttttatcttctcctagccggcctgg 18540
    tggggtctcctcccctcctcctctgcccag catctgtaatagcaccaaatgagcacggaa 18600
         18610     18620     18630     18640     18650     18660
    ┴┴┴┴┴┴┴┴┴┴┴┴┴┴┴┴┴┴┴┴┴┴┴┴┴┴┴┴┴┴┴┴ ┴┴┴┴┴┴┴┴┴┴┴┴┴┴┴┴┴┴┴┴┴┴┴┴┴┴┴┴┴┴┴┴
    cctcgcatcatgttcctgggtttgactccc agctcagccgtcctcttcctaggcttgtga 18660
    ccttggataagtccctgtcacccctctcag ctgaagaacatgctccctcatcgagtctga 18720
    tgaaaacgccctccataaacgtgcctggca catggtttgtttattctctggatctgaaac 18780
    ggtgaaagaggcagagctgagtaggtcggg ctgccttgggcatggctttggtcagcagag 18840
    gggccggcttcacgccacttcccatctcct gaataattcatgacgaacaaaatgactggg 18900
         18910     18920     18930     18940     18950     18960
    ┴┴┴┴┴┴┴┴┴┴┴┴┴┴┴┴┴┴┴┴┴┴┴┴┴┴┴┴┴┴┴┴ ┴┴┴┴┴┴┴┴┴┴┴┴┴┴┴┴┴┴┴┴┴┴┴┴┴┴┴┴┴┴┴┴
    ccagacctgggccctccctcctcctgtcgt gaaggcagaaaagtttctaattacagatca 18960
    gccggccaggctccccggggcccctgggcg ctgcacacaggggggcatttatgggaagaga 19020
    ccatggaggggaggggttcggtcccagctc cttccagaagaaactcaactccttttgaa 19080
    attgtaaccttggcctgctaaggcccagga agggactggggaaagaaacttagaagagga 19140
    agagaaaaccctgccgagggggtcagagaga agcgcccagaaaaaaatgtcaggtcaaaga 19200
```

FIGURE 11-M

```
        19210     19220     19230     19240     19250     19260
agggggctctggggacgtcctggcaagagga atacacaagctgtcaggggaggagatttgc 19260
tcgagtcccgtggaaagcatgacaaagccg ggcttcaaaaggaagctgtccttcgaaaat 19320
acattgagaaagaataagatctagcgttct accatacagtagggagactagagttaataa 19380
tttgtcatagagttcaaaattgcttggctg ggagcggtggctcacgcctgtaatcccaac 19440
actttgggaggccgaggcaggcagatcacc tgaggtcaggagttcgagaccagcctgtcc 19500
        19510     19520     19530     19540     19550     19560
aacatggcgaaagaacccgtctctactaaa aaaatacaaaaattagctggatgttgtagc 19560
gggtgcctgtaatcccagctacttgggagg ctgaggcaggagaatcacatgaacctggga 19620
ggcggaggttgccgtaagccgagatcacgc cactgcactctggcctgggccacagaatga 19680
gattccgtctcaaaaaaaaaaaaaaaaaa aaaaatttgctggaggagaggaacggaga 19740
tgtttcccaacatgaagaaggggtgaatat ttgggttgatggatgtcccagttatcctga 19800
        19810     19820     19830     19840     19850     19860
tttgatcatcacacattgcatgtatgtatc aaaataccacatgtgcccccaaaatatgta 19860
ccattattatgtataacttttttttttttt gagatggagtatcgctctgtcgcccagtcc 19920
tgagtgcagtggcgccatctcagctcactg caagctccgcccccggttcacgccattc 19980
tcctgcctcagcctccccagtagctgggac tacaggcgcccgccatcacgccggctgat 20040
gttttgtatttttagtagagacggggtttc accatgttagccaggatggtctcaatctcc 20100
        20110     20120     20130     20140     20150     20160
tgacctcgtgatccgcctgccttggcctcc caaagtgctgggattgcaggcatgagccac 20160
cgcgcccggcccatgtgtcactttttttaaa aaaggaagatttcttgactccaacaccaca 20220
gcctctcagttacactacaatttactcatt catctgtaaaatggggagatgcccaataat 20280
gctaccttacagcattattgaggagttaca caagtaaataaatgtcaagtgcttagaata 20340
ctgcctcacacataaactaaaaatatatat tagtagttgtagagttttttttttttatatt 20400
        20410     20420     20430     20440     20450     20460
atgctccctccatagagtggtcagtaaagg gtgaaggtgacaagaagagaagatttgggg 20460
agattgttagagagaacaatgattgtcagg tagtttagtatagtgattaagatgaggacc 20520
ccatacataataccgtaataataataataa aagaggtcagctgcggtggctcatgaccgt 20580
aatcccagcactttgggaggctgaggtggg cagatcgcttgagttcaggagttcaagacc 20640
agcctgggcaacatggtgaaaccctgtctc tactaaaactacaaaaattagccaggcatg 20700
```

FIGURE 11-N

```
            20710     20720     20730     20740     20750     20760
          ....|....|....|....|....|....|....|....|....|....|....|....|
          gtggagggtgcctgtagtcccagctacttg ggaaagtgaggcatgagaattgcttgaacc  20760
          caggaggtgaaagtttcagtgagccaagat gggcaacagagcgtgactctgtccaaaaaa  20820
          aataaataaataaaataaaaaagaggccag gtgtggtgtggtggctcacgcctataatcc  20880
          agcactttgggaagctgagggggagtggatt gcttgagttcaggagttcaagaccagcctg  20940
          ggcaacatagtgagaccctgtctctacaaa aagtacaaaaattagctgggcgtggtggtg  21000
            21010     21020     21030     21040     21050     21060
          ....|....|....|....|....|....|....|....|....|....|....|....|
          ggtacatgtagtcccaactacttgggaggc tgaggtgggaggatcacttgagcctgggag  21060
          gtggaggctgcagtgagccaagatcgtgct gctgctctccagtctgggcgacacagtgag  21120
          accctgtttcaaaaaaatttaaaaagtaag gactccagcactagtttgcctgggttcaaa  21180
          tcccagctctgcctcttactagttgtgtga tcttggacaggtttgctgtaggtctccgag  21240
          ctcctattcactgtctgtaataaacggtag ccactgcagttagtggagagtggtgaacaa  21300
            21310     21320     21330     21340     21350     21360
          ....|....|....|....|....|....|....|....|....|....|....|....|
          aatgaccaaggtccctgtcctcatggagct tacagtctagcaggaaggttatactaatca  21360
          agagcgtttattgcatgccaactgtgtgca ggtcctgtgcacttggcagacattctctta  21420
          acgaaatttcacagaatccaccoctgtctt acagatgaagagggtgaaactcaaagaggt  21480
          cacaagcagagagaggatttagaactgaaa ggtcactccacagtatggatgaatcaccac  21540
          attagcatggtgagcgaaaaaagccagatg caaacgagtacacattgtatgatttcattt  21600
            21610     21620     21630     21640     21650     21660
          ....|....|....|....|....|....|....|....|....|....|....|....|
          atatgaaactctagaaaatgcaaactaact tatagtgacagaaagcagatcaggggttgc  21660
          gtgggacagggtgggcggggcattcactgc aaagagcctgaggaacctatttgagaagat  21720
          ggaaatgttttacatctgacattgatacta gttacatgggtgtatgcatttgtcaatgtt  21780
          catcgaactggacacttaaaatgggtgtat tttcctgcatgtaaattatacctcaatgaa  21840
          gctgatcttttcaaggggtgtgggaaggta taccagactccagagctctgcaacccttcc  21900
            21910     21920     21930     21940     21950     21960
          ....|....|....|....|....|....|....|....|....|....|....|....|
          tatattatttgagtgtctgatttcaagctc atttgtgggcagagactgtaatagattcat  21960
          ctttaggtcctcccctcacttcccagcctg agggcctagcaaaattcttttttttgtttt  22020
          ttttttttgagatggactctgactatgttg cccaggttggagtgtggcagcacaatgttg  22080
          gctcactgcaacctctgcctcccggttca agagattctcttgcctcagcctcccaagta  22140
          gctgggattacaggcgactgccaccacatc tggctaattttgtatttttagtaaagacg  22200
```

FIGURE 11-O

```
       22210     22220     22230     22240     22250     22260
    |....|....|....|....|....|....|  ....|....|....|....|....|....|
    gggtttcaccatgttggccaggctggtctt  gaactcctgacctcaggtgatctgcccgcc  22260
    ttggcctcccaaagtgttgggatgacaggc  gtgagccatcgcgcccaaccaaaattctta  22320
    aacccaatagttcagattagcaaatatacc  ctgggcaccttctctgtgctgggtgctgcg  22380
    gtcacagaccaatcagtctagtggggaaca  cagacggaaaaggccaaatagacacagtac  22440
    agtgggtaaatgtgctgatggagtaaacag  ttcattactgggccacagcaatgaatcctg  22500
       22510     22520     22530     22540     22550     22560
    |....|....|....|....|....|....|  ....|....|....|....|....|....|
    catagagtctggaacttgggatgtgaagat  ctcaaactgcaattcatcacctgcattcaa  22560
    atctccactctaccgcttgctgtatgactt  tgggtgaccattttagcatgccaaacctca  22620
    gtttccacctctggaaaatggagatcatag  tagctccaatctagagggtgttatgagaa  22680
    ttaaaggagacagcaataaaatgtttagca  tggcaggcatagtaagtacttcataattgt  22740
    tagtcattttatcatgaatgaagagcagg   gaggtggggagaggcacacggggtgtgtgt  22800
       22810     22820     22830     22840     22850     22860
    |....|....|....|....|....|....|  ....|....|....|....|....|....|
    atgtgtagtgggttcactacccaacctg    aggtgagagaggactgagaggtgctttccc  22860
    agagaggtgatgcttggaggaggaattggc  tagtttaagtggccatgggggcaggaggga  22920
    gtgggaacagcttggaacaaacgctcaata  aatatttgctcaataaataaaaaaacagag  22980
    actgtgcaaaacctgcctgtaaccaagggg  acagagagggcccgccagaggagactgggg  23040
    ggtcctcaggaggcggggctgggtggctg   gcccccacaggcaggctccagaccttccta  23100
       23110     23120     23130     23140     23150     23160
    |....|....|....|....|....|....|  ....|....|....|....|....|....|
    gcctggtccgaccccaccctgtgccctgcc  cagttcccctgataggtttggacagcccca  23160
    gacctgaggcctggagcccacgggaggagg  aacggtggggagggctggcgggacggggt   23220
    gctcacaggccttctccctctaatgagaaa  cggccaagtcccgcaaggcgcctccgcg    23280
    ccccgttgtccgagccacaaaggaccagg   atcaatggaaggcgggagcgaccgaggggc  23340
    ctcctctttgtgcggctgtctcaggcctgt  ttgcgccgcgtctccgcgccccattgat    23400
       23410     23420     23430     23440     23450     23460
    |....|....|....|....|....|....|  ....|....|....|....|....|....|
    caggcatgtggaaagattccgcctccggg   ctccctttgtggccgcgttgccaggctgcg  23460
    cccggagtgactgcaccgcgcagggtgtac  ccgcctgcggtgggcacgggctgcgagac   23520
    ggggtgggatcccaggagggcagggtggcc  agatttagcaaataaaaatacaggacttcc  23580
    agttaaatgtgaatttctgataaataacaa  aagcagacaaaaaacaaagtataagtatgt  23640
    cccaaatattgcatgggacatacttacact  caaaaagtattggttgattatctgaatttt  23700
```

FIGURE 11-P

```
              23710     23720     23730      23740     23750     23760
    ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
    caacttaactaggcgtcctgtattttgtct ggcacccttttgaaggggaagctgaatacat 23760
    ctgcattgcctagcacttatattacccca acttcagtggttgaagttttgtttgtttgc 23820
    ttgcttttttgttttttattttttattttttg gccatatctgcacaccccgaactgctatttt 23880
    agatagaattttttctttaaataaatttatt ttttaaaaatcttaacctggccgagctccg 23940
    tggctcaagcctgtaatcccagcactttgg gaggctgaggggggggaggatcacttgaagc 24000
              24010     24020     24030      24040     24050     24060
    ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
    caggagttcaagatcagcttgagcaacaaa gtgagatcccatctctacaaaacaaaacaa 24060
    aaaactcccttaacctattaaccgtgatttt attgatgcatagtgcaaatacattaacttg 24120
    aacaaatatgaaatgtacctgttgatgcat ttttgcctacaagaacactcatgtgaccgc 24180
    acccacatcaagatatagaatattccggc cagcagtggtggctgacgcctgtaatctca 24240
    gcactttgggaggccgaggtgggcgaatca cttgaagtcaggagttcgagaccagcctgg 24300
              24310     24320     24330      24340     24350     24360
    ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
    ccaacaaggtgaaatcccctctctactaaa aatacaaaaattagccaggggtggtggtgc 24360
    acgcctgtaattccagctactcaggaggct gaggcaggagaattacttgaacccgagaag 24420
    cggaggttgcagtgaaccgaagtggtgcca ctgcactctggcctgggcgacagagcgaga 24480
    ctccatctcaaaaaaaaaaaaaaaaagata tagaatattcccatcaccccagaaggttcc 24540
    ctggcgtccctgagcagttgagcagtatcc acctccccattggcagccatagatttgctt 24600
              24610     24620     24630      24640     24650     24660
    ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
    tagctattcttgaacttcgtatcagtggaa tcgtatagtataatgtgtacactcaagtct 24660
    agcttctttcgctcagtattatgtttgtga ggatgggcatggtggctcacgcctgtaatc 24720
    ccagcactttgagaggcccaggtgggtgga tcagtatcacctgaggtcaggagttcgaga 24780
    ccagctggccaacacagcgaaacccatct ctacaaaaatgcaaaaattagctgggcatg 24840
    gtggcaggtgactgtaatcccagctacttg ggaggctgagataggagaatcacttgaatc 24900
              24910     24920     24930      24940     24950     24960
    ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
    cgggaggcggaggttgcagtgagccaaaat tgcaccactgcactccagcctgggctacag 24960
    agtgagatttcatttcaaaaaaacaaaaaa caaaacaaacaaacaaaaaaagtctgtgac 25020
    atttgtccccattgtagattgaccagttgt ttgttcccttttgctgctggctgagtattc 25080
    cattatatggctgttccacggtttgttcct ctattttcttgttgatgggtgtcttgattg 25140
    tttccagttttttgctattatgaataaagcc gctatgaccatacttgcactggtcactgta 25200
```

FIGURE 11-Q

```
        25210     25220     25230     25240     25250     25260
tgaacttaaatatatttaacctaagcaata ctatttgtgaactcacaggcttaaaatgct 25260
actttaattttttttctcctgcacattaaa tatataacgatgacacatgtttctgggaac 25320
atctttgtattgaccaagctcactgtgaat ggtcacatatcaaactgcagaatagacgtt 25380
aagagaacagactggcttggggtaggtctc gagcaagtgcgtcagtccctctgggcctcg 25440
gtttcttcatctgtgcaatgggggtgata  atgttaattatctcacagagtggttgaaaa 25500
        25510     25520     25530     25540     25550     25560
ggcaaaatgggccgggcacggtggctcaca cctgtaatcccagcacttttggaggctgag 25560
gtgggtggatcatgaggtcaggagttcaag actagcctggccaagatgacaaaaccctgt 25620
ctctgctcaaaccacaaaaattagccaggc acggtggcaggcaccttaatcccagctact 25680
tgggaggctgaggcaggagaattgcttgaa cccgggcagcagaggttgcagtgagccgag 25740
atggtgccactgcactccagcctgggcaag aaagtgagactgtctcaaaaaagaaagaaa 25800
        25810     25820     25830     25840     25850     25860
ggaaagaaggaggaaggaagaaaggaagga aggcaggcaggcaggcgggcaggcaaggca 25860
aaatggggtaacaccttataaaagggccag ccatggtggcacacaggagagttgcttgag 25920
cccaggagttcaagatcagcctgggcaaca tagtgagacccgtctcaaaaaaaaaaaaa  25980
aaaaggatacagcatagggctgacacatag tgggtgctctacacagggagctattatcca 26040
gtgctggatgggcagtagcaattgaactgg ctatgttagatgcctgttctcattctattc 26100
        26110     26120     26130     26140     26150     26160
tcatttcaacccttttgaggtagctactgtt attatcaacctatttacagattaggaaac 26160
tgaggctctgagaggcagtcacttgcccaa aatggtatagttagtaagcggcaaaggcac 26220
cacctagtgtgttttccagagcccaagggg gcaggagggaccaatgaggctctcatgcct 26280
ggagatgagaatggggttatacaggaggagg agctgggtaccttctccttcctgcctctgc 26340
atccccaattagcgcccagcttgaaggcaa gcaggtttctctttggagggtgggaggagc 26400
        26410     26420     26430     26440     26450     26460
tggcctggacatttctaggagacgccaagc cttccagccaacgggcaggtgggaggacag 26460
gcagggcaagtctgacggggtaaggagggg aacagaggaagccggaagctggaggaaaag 26520
cctggcctcctgtagccacagccgctgggc agagccggcctgctacctgccatctgaa   26580
gggcacgggaactgctgatctcaggcgatt agcataacaatccccgatccggcgtcctcg 26640
ggtcccaaagctgggtctgcacaatcccat ttcaagccagctctttctttagctggttaa 26700
```

FIGURE 11-R

```
         26710     26720     26730     26740     26750     26760
     |||||||||||||||||||||||||||||||||||  |||||||||||||||||||||||||||||||||
ttagggagggcacagactacttaaagggcc ctgtacacacggccttggctgcagctggga 26760
gcaggagagggcccgacaataccttcagtc ctggcaggtgtgggtgctgccatagtgctt 26820
cacggcaggccacggcgaaaaggctgctct caccggggatttcacgggcctcctgttgc 26880
caccctccaaagccccattagtgcacatct aggatagatatggcctgttcacagctcatg 26940
ccagggctcggcacagaataggtgctcaaa tataacttctaaaataagtaactgggccag 27000
         27010     27020     27030     27040     27050     27060
     |||||||||||||||||||||||||||||||||||  |||||||||||||||||||||||||||||||||
gcgcagtggctcatgcctgtaatcctagca ctttggaggccaaggcaggaggatcactt 27060
gagtttcagaccagcctggccaacatggca aaaccttgtctctactaacaatacaaaaat 27120
gagctgggcgtggtggcacacgcctgtaat cccagcaactcaggaggctgaggcatgaga 27180
atcgcttgaactcgggaggtggaggttgca gtgagccaagattgccccaccgcattccat 27240
cccgggcaacagagcaagactctgtctcaa aacataaaaataaaataaaataaattatcc 27300
         27310     27320     27330     27340     27350     27360
     |||||||||||||||||||||||||||||||||||  |||||||||||||||||||||||||||||||||
aggtgtggtggtgcgtgcctgtggtcccag ctacttgggaggttgaggtggggaagatcgc 27360
ttgagcctgggaggctgaggcttcagtaag ctgcgatcctgccaccgcattccaccctgg 27420
gtgacagagcaaaaacttgtcacgaaaata aataaaataagataactcactgaagcatgg 27480
agcccatagtccagaactcaggactctacc tactcatataatgagggcccaggctgaatg 27540
ctaatggagggtacaggggcagccccagcc ttgcaggtccctcagggtcctaagcccttc 27600
         27610     27620     27630     27640     27650     27660
     |||||||||||||||||||||||||||||||||||  |||||||||||||||||||||||||||||||||
cttccccttcccacagcctccttgcactgg aagtccaagagggcacttggatcagagtag 27660
gcagaacatagtctttgggatgagatagag ggtagagctgggttcgaatcctggctctgc 27720
tgcttactagctgtgtgatccagaggaagt ctcttaacctctctgaggctgttttctctt 27780
ctgtaaatggggatgatcaaaacctgcttc aaaagttgtttacaggtatttcttaaaata 27840
tcatatgagagcgtctgccacagagttggg gctcagggaatgggagtccttcctcttctg 27900
         27910     27920     27930     27940     27950     27960
     |||||||||||||||||||||||||||||||||||  |||||||||||||||||||||||||||||||||
tagaaatacccactgcctttctaccogcgt ggctaatgttccccaggtccccatcatgca 27960
cccgctcagtgcttgttctctctgccatcc tgtcaatgcccttgtgaggtaagttctgtg 28020
ctttctttttttttttttgagatggagtct cactctgtcgcccaggctggagtgcagcgg 28080
tgcgatctcggctcactgcaagctccacct cccggggttcatgccattctcctgcctcagc 28140
ctcccaagtagctgggactacaggcacctg ccatcacacacagctaattttttgtatttt 28200
```

FIGURE 11-S

```
              28210     28220     28230     28240     28250     28260
         ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
         tttagtagagacagcatttcactgtgttag ccaggatggtcttgatctcctgacctcgtg 28260
         atccacccgcctcggcttcccaaagtgctg ggattacggggtgagccaccgctccctgcc 28320
         agttctgtgcttttaaagaaaaggggccc ggtggtgcagtggctcatgcctataatccc 28380
         agcactttttgtttgtttgtttgtttgtt tgtttgaggcagagtcttgttctgtcgccc 28440
         aggctggagtgcagtggcacaatctcggct cactgcaacctctgcctccgggttcaagt 28500
              28510     28520     28530     28540     28550     28560
         ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
         gattctcctatctcagcctcccaagtagct gggattacaggcacctgccaccacgcccag 28560
         ctaattttgtaattttgtagagatggggt ttcgccacgttggccagactggtcttgaac 28620
         tcctgacctcaggtcatctgcccacctcgg cctcccaaagtgctgggattacaggtgtga 28680
         gtcactgcgcctggccaataatcctagcac tttggaagacctaggcaggaggatcacttg 28740
         aggccaggagtttgagatcagcctgagcaa tgtagcaagaccctgtttcttcaacaaaat 28800
              28810     28820     28830     28840     28850     28860
         ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
         tatatattcaaaatgttaaggctgagcgtg gtggcttgcggctctaataccaacactttg 28860
         ggaggctgaggtggggaggatggcttaagcc caggagtgcaagatcagcctgggcaacatg 28920
         gtgagacatcatctctacaaacaaaatttt ttaaaataaaaaataatgatttttaggcca 28980
         gatttggtggctcatgactgtaatcacaga actttgggagggcaaggcaagctgatctct 29040
         tgaggtcaggagttcaagaccagcctggcc aacatggtgaaaccccatctctactaaaaa 29100
              29110     29120     29130     29140     29150     29160
         ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
         tattaaaaaattagagccaggcacagtggc tcacacctgtaacccagaactttgggagg 29160
         ccgaggcgggcggatcacaaggtcaggaga tcgagaccatcctggtcaacatggtgaaac 29220
         cccgtctctactaaaaatacaaaaattagc tgggcgtggtggcacatgcctgtaatccta 29280
         gctactcgggaggctgaggcaggagaatcg cttgaaccgggaagtcagaagttgcagtga 29340
         gccaagatcgtgccactgcactccagcctg gcgacagagcgagactctgtttaaaaaaaa 29400
              29410     29420     29430     29440     29450     29460
         ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
         aaaaggccgggcgcagtgactcacacctgc ctgtaatcccagcactttgggaggctgagg 29460
         caggcagatcacctgaggtaaggagttcga gaccagcctgaccaacatggagaaacccca 29520
         tctctactaaacatacaaaaaaaaaatta gccaagcgtggtggtgcatgcctgtaatcc 29580
         cagctgctcaggaggctgaggcaggagcat cactggaacccaggaggcagaggttgccgt 29640
         gagccaagatcacaccattgccctctagct ggggcaacaatagcgaaatgccatctcaaa 29700
```

FIGURE 11-T

```
       29710     29720     29730      29740     29750     29760
aaaaaaaaaaattagttaggtgtgatgacac  acgcctgtaatcccagctagttgggaggct  29760
gaggcaggagaatctcttgaacctgggaag  cccactgcactcagagtgaatgagactggg  29820
ccacagagtgaatgagactctgtctcaaaa  taaataaataaataaatataataataattt  29880
tttaaaaaggaaaatgaagtcagagacaaa  gtgacttgcccaaggccacacggctagaaa  29940
gtttcaaagggaggcttgagctcagctaac  cctaagaacaatggctctggagccaggaaa  30000
       30010     30020     30030      30040     30050     30060
ggatgggcattattgcagccactgctccct  ttccactcagccagccagatagtctcaggt  30060
atcttttgatcttctgctgtgtgttaagca  ttgtgctgagggcagggatagagctgagc  30120
acaatcgccattttccatcaatgtctgtga  gtgttaagggcttgaggacagtaaaacagg  30180
gtgataggctagaggcctgggggtctagga  agacttcttctgtataggtgatacttgaac  30240
tgcaggattgccatgggaagagggggcag   gtaagtgggaagcattccaggtaggcggga  30300
       30310     30320     30330      30340     30350     30360
gagcaggtgcaaaggtcctgaggtaggact  tagtttggggtatctcaggaactgaaaggc  30360
agccagtgtggctggagcactgggagggag  agtgagagtgggatgggccaggctggagag  30420
ggaggaagggccttaagggacatcctaaga  actccttccttcccttcctccctcttcctt  30480
tccttcttctctccctcccttccttccttc  ccttcctcctcctccttcctttcttccctc  30540
cctcccttcctgccttccttctcttttttc  ttcccttccttccttcttctccttccct   30600
       30610     30620     30630      30640     30650     30660
cccatcctttttttcttacttcctccctca  atctctctctctcttcctactttccttccc  30660
tccttccttccttctcttgttccttcctcc  cccctctcctttccttccttccctcctcct  30720
tccctcttccctcccttccttctctccttc  cctctgtccttttttttttttttttttttt  30780
gagacagagtctcagccaggcatagtggct  cacgcctgtactcccagtacttggggaggc  30840
cgaggcaagtggatcacctgagatgaggtc  aggagagtttgagaccaacctggccaacat  30900
       30910     30920     30930      30940     30950     30960
ggtgaaaccctgtctctagtaaaaatacaa  aaattagctgggtgtggtggtgggtgcctg  30960
taatcccacctacttgggagactgaagcag  gagaatcacttgaacctgggaggcagcagt  31020
tgcagtgagccaagatcatgccactgcact  ccagcctgggcgacagagcgagactccgcc  31080
tcaaaaaaaaaaaaaaaaaaaaaaagaga   cagagtcttgttctggcaccatctcagctc  31140
actctaacctctgcctcccgggttcaagca  attctcctgcctcagtctcctaagtagctg  31200
```

FIGURE 11-U

```
           31210     31220     31230     31240     31250     31260
        |....|....|....|....|....|....|  ....|....|....|....|....|....|
        ggattacaagcacctaccaccacatctggc  taattttgtgtttttagtagagacggggt 31260
        ttcaccatgttggccaggctggtctcgaac  tcctgacctcaagtgatctgcccacctcag 31320
        cctcccaaagtgctgggattacaggtgtga  gccaccgcgccaggctccttccttccttcc 31380
        ttctttccttcctcttttcttcctcccctt  ccctccctccgttcctcccttccttctttt 31440
        ctctctctccttcctttcttccttccccc   ttcctcccttttccctgccttcctacct   31500
           31510     31520     31530     31540     31550     31560
        |....|....|....|....|....|....|  ....|....|....|....|....|....|
        tccttccttctttctctccttccttcctcc  cctcctccctctcttccttccttcctcctc 31560
        tccttccctccctccctccttcctctctcc  cttccttcctcctctccttccctccctccc 31620
        tccttcctctctcccttcctaccttccttc  cttccctcccctccttccttcctcccctcc 31680
        ttcctctcttccttccttccctccgtcctt  ccttctttccctccgtccatgcctactgtt 31740
        tctcaagcactggcccagggggctgcaggc  ctctgagtctctctgtgcttctctccctct 31800
           31810     31820     31830     31840     31850     31860
        |....|....|....|....|....|....|  ....|....|....|....|....|....|
        tcccttctcccttcctctccctccccctc   ctcttctaacagccgccccaccccactgg  31860
        tccagctcttcccctccctctaccccatc   ccctcccctccacgccaccccctcccactg 31920
        acaatggggaggaaccctgggctcagctcc  ccacagtattgtccctttaaggaatccta   31980
        aatccggacaccctctcctcccccacctg   agaaccaattagggttcccgaattcaagta 32040
        gaggcttttgtgtgtcacgtgtttgtggaa  caaagccctctccggcaggaataaaagctt 32100
           32110     32120     32130     32140     32150     32160
        |....|....|....|....|....|....|  ....|....|....|....|....|....|
        ctattcaggagccagtttgctctcattcta  atcgtttccactccagcctcgcctccttcc 32160
        cgggttcccagggccgccagctcggcctc   accttcccgcttcagcaccctgtattagtg 32220
        ccctacccaaaagcaggtggccaccgaccc  agggctctgcccacctttcttcccgaaag  32280
        atcacgtgatgccgactggctccgagctgg  gccctgggctcagcgctgtgtgagcatcat 32340
        tgtacgggactgtgaatagcctcaatgcaa  cggaggaaactgaggctcagagaggttagg 32400
           32410     32420     32430     32440     32450     32460
        |....|....|....|....|....|....|  ....|....|....|....|....|....|
        gcacttgcctgaggtcatacggctggtaag  acaggagtctacaccctcgggcattattc  32460
        tatggtaccccagctggccctagcatagc   acagggtgcagaagaagggagctgccattt 32520
        ttataaagcccatggggccaggcacctgct  ggatattagagactcctgacaatgccacgt 32580
        gaaggagcaacgattgaggtcaaagtcact  gacaagtcgaggcaggatggcgtttgggac 32640
        tcagaacttggagggaaacagtggggccct  caggtctgaagatgaagagacagggagtat 32700
```

FIGURE 11-V

```
         32710      32720      32730      32740      32750      32760
gggaagcccatattacgaagccattaagaa aactgtattgatatggaatggtaattgaca 32760
cattgccaagagaaaaaggcagtacattga atggaatatgatctcatttgcataagagga 32820
aaaggaaatatctacacacaaacatgtata cacatatcgcacatttctatctgtatggaa 32880
taaatttggggaaaaaaacatcataaattgt agtatcctttatttcctttgaagagtggaa 32940
atagagcatggagagaagtcacttagtacc attctgtgctgtttgaaaaaagatattttc 33000
         33010      33020      33030      33040      33050      33060
ttactatgatcatgtatttattttatgata attattttgttttattgaagttaactatt 33060
ttaaagcttgcatttcagttgcatttagta tatttacaacgttttcatcccctaaaggc 33120
aaacttctaacatcatatccagtaagcaat tacttctccttccttattccccccgcccct 33180
ggcaatcactaacctgctttctgtctctac agatttacctattttagatatttcatagaa 33240
atggaattatagcatttcatagaaatggaa tcagtatgtgacctttttcatctggctttt 33300
         33310      33320      33330      33340      33350      33360
ttctttttccttcttttttttttttttttt agatgagctctcactctgtcacccaggttg 33360
gagtgcagtggcgcgatctcagctcactgc aacctccacctcccgggctcaagcgatcct 33420
cctgcctcagcctcccaagtagctgagacc acaggtgtccgccaccacacccaactaatt 33480
ttttttgtatttttgatagagatagggtttc tccatgttgtccaggctgatctcaaactac 33540
tggattcaagcgatctatctggcttggcct cccaaagtgctgggattaaggccggcaaaa 33600
         33610      33620      33630      33640      33650      33660
tgcacccctgagctcagcctggtttttttc atttaggatgatgtccctcaggtttatcca 33660
tgttgtagcatgtgtcctatttcattcctt ttaacggctaaatagtattcccttgcatgg 33720
gtatactacatcttgtttacccattcatca cttgatggacatttggggttgtttcaatctt 33780
ttggcagtcgtgaatggtgctgctatgatc atgcatgttttgtctgaataccgtttttt 33840
aattattttgggtatatgcctaggatctgg gtcatatgataattctgttttacttttttga 33900
         33910      33920      33930      33940      33950      33960
gataccatcgaacggttttccacagtgcca caccatttacgctcacaccagcaacgtac 33960
agaaagctccaatttctccacattcttgcc aacacttgtcatttccatttatttattta 34020
ttcatagctgtggtagtaggtgtggaatga tatctcattgtggcctttgccttgcatttca 34080
ctaatggctcaagatgaatatcttttcacg agcttattggctatttatgtatttttctttg 34140
aagaaatatctattcaagtcctttgcctat ttgtacttattttaatttatttttgag 34200
```

FIGURE 11-W

```
            34210     34220     34230     34240     34250     34260
aaagagtcgcactttattgcccaggctgga gtatagtggcttgatcacagctcactgtag 34260
cctcgacctccctgggctcaagtcctcctg cctcagcctcccaagtagctgggactacag 34320
gcacacgccaccatgcctggctaattttg  tattttttttttttttgtagagatagggt 34380
ttcaccatgttggccaggctgttctcaaac tcctgacctcaagtgatccgcccacctcag 34440
cctcccaaagtgctgagattacaggtgtta caggtgtcagccactgcacccagcccttt 34500
            34510     34520     34530     34540     34550     34560
cactttttttttttttttttttgagacagt ctcgctctgttgcccagactggagtgcagt 34560
ggcacaatcttagctcacagcaacctccac ttcccaggttccagcgattctcccacctca 34620
gcctcccgagtagctgggactacaggcgcc caccaccactctaagctaattttttgtatt 34680
tttaatagagatggggttttaccatgttgg ccaggctggtctcgaactcctgacctcaag 34740
tgattcgcctgccttggcgtcccaaaatgt tgggattataggcgtgagccaccacacctg 34800
            34810     34820     34830     34840     34850     34860
gcctcactttcttgatagtgcctttgatg  cccaagttttatttttatttatctattca 34860
tttatttattttgagacagggtctcgctct gtcacccatgctggagtgcagtggcacaat 34920
catagctcactacagcctcgaactcctgag ttcaagccatcctccagccttagccttcca 34980
agtacctaggactccaggctcgtgccacca cccagctaaatttgttatttatgtagag  35040
acgaggtcttactatgttgcccaggctggt ctcaaactcctgagtttaagcaaccctcct 35100
            35110     35120     35130     35140     35150     35160
gcttagcctcacaaaatgctgggattacag gcatgagccactgcacccagccaaaagttt 35160
taaatttaaatgaagtccaatatatctatt gttttcttgtgttgtttgtgcatttggtga 35220
cataactaagaattgccaaatttaaggtca taaagatttacccctgtgtttcttttatcc 35280
attttgagttcatttgttttacatggtg   ccaggtccaactttattctttcacatgtaa 35340
atatcctataataattgtttttaatctttg tctttgctgtcttaagaaatgatctccaaa 35400
            35410     35420     35430     35440     35450     35460
tttttgtgatgatacatccctaagaggaaa caatctttgagctcatatttctagcataca 35460
tacatttatatatttacaaaatatatacat actctactgttataatatctatgttacaaa 35520
catctatgcaaaagaaatttaaaaagatg  aaataggctgggcacagtgtctcatgcctg 35580
taatcccagtactttgggaggctgaggtgg gtggatcactggaggcgaggagttcaagcc 35640
cagcctggccaatacggtgaagcccagtct ctcctaaaaatacaaaaattaggccgggag 35700
```

FIGURE 11-X

```
       35710      35720     35730      35740      35750      35760
cagtggcacgcacctgcaatccaagcactt  tgggatgctgaggcaggcgaatcacctgag 35760
gtcagggattcgagaccagcctggccaaca  tggcaaaaccccatctctactaaaaataca 35820
aaaattagctgggcatggtggcgtgtgcct  gtaatcccagctacttgggaggctggggca 35880
ggagaatctcttgaacccaggaggcagagg  ttgcagtgagccgagattgcaccactgccc 35940
tccaacctgggccacagagtgagactccat  ctcaaaaaaaaaaaaaaaaaaaaagctggg 36000
       36010      36020     36030      36040      36050      36060
cgtggtggcacatgcatataatcccagata  ctcagtaggctgaggcaaaagaatcacttg 36060
agcctgggaaaaagagattgcattgcagtg  agctaagattgggccactgcactctagcct 36120
aggcgacaaagtgagattctgtctaaataa  ataaataaaataagaaattagccagatata 36180
gtggcacgcacctgttgtcctagctactca  ggaggctaaagtgggaggaaggcttgaacc 36240
caggagttcaaggcttcggtgagttatgat  tacatcactgctgcactccagcctgggcaa 36300
       36310      36320     36330      36340      36350      36360
cagaggcacaccctgtcttaaaaaaaaaaa  aaaaaaaaaaagagcggggaaaagagatga 36360
aatagaaaaaatactatagaaggcctgat   cttttcttggtggatgattttgagtgctcc 36420
cagagacactcacccctctggtgcttgctg  gtgctgctgatgacagagtgaggtcagccc 36480
accctctaaaggcacagctgggacagctgc  aggcaggcatgggagtgggctctccaggtt 36540
gggtctgacttccctcttctgagtcacaaa  atttcacatcagaaggacgggtgtttgaat 36600
       36610      36620     36630      36640      36650      36660
cctggttccatctatttcctagttgtgtgt  cactatattaagctgtatttggccgcgtgt 36660
ggtggctcacacctataattgcagcacttt  gggaggctgaggcaggtggatcacctgagg 36720
ttagtagttcgagaccagcctggccaacat  gatgaaatcccgtctgtactaaaaatacaa 36780
aaattagccagatgtgctagcaggggccta  caatcccagatacttgggaggctgagacag 36840
gagaatcgcttgaacctggaaggtggaggt  tgcagtgagccaagatcacaccactgcact 36900
       36910      36920     36930      36940      36950      36960
ccagcctaggcaacaaagtgagacaccgtc  tcaaaataaaagccatatagctatattaaa 36960
aagcaaagtcttaacagccttttttttttt  tttagacagggtattcttctggtatccagg 37020
ctggaatgcagtggcacgatcatagctcac  cgcacccttgatctcccgggcccaagcgat 37080
cctcccacctcaggtttccgggtagctggg  cctacaggcaagtgccaccatgcctggcta 37140
attttaaattttttgtagagacagagtctc  cctttgttgctcaggctggtctcgaactcc 37200
```

FIGURE 11-Y

```
       37210     37220     37230     37240     37250     37260
    |....|....|....|....|....|....|....|....|....|....|....|....|
    tggccttaagcaatcctcccacctcggcct tccagagtgttgggtttataggtgtgagcc 37260
    ttacacttagccttttttttttttttttt  tttgagacggagtttcactcttgtccctca 37320
    ggctggagtgcaatggtgcaatctctgctc actgcaacctctgcctcccaggttcaagca 37380
    atcctcctgcttcagcctcctgaacagctg agattacaagcatccgcccccatgccaggc 37440
    taatttttttttttcccatgacagaatctt gctctgtcgcccagaactggagtacaatgg 37500
       37510     37520     37530     37540     37550     37560
    |....|....|....|....|....|....|....|....|....|....|....|....|
    ctcgatcttggctcactgcaacctccacct cccaggttcaagcaattctcctgactcagc 37560
    ctcccgagtagctgggattacaggcgcatg ccacctgcccggctaattttttgtatttttt 37620
    agtagagacaggatttcaccatattggcca ggctggtctcgaactcctgacctcgtgatc 37680
    tgcccgcctcagcctcccaaagtgttggga ttacaggcgtgagccaccacgcccagctgg 37740
    ttattatttcttaaggcttaaagggccaa  tgtgtcttccccacaatttacctatttgtt 37800
       37810     37820     37830     37840     37850     37860
    |....|....|....|....|....|....|....|....|....|....|....|....|
    cattcagccaagatgtaaagaatgcctgct atgtgccagccataatggggaacaagaaga 37860
    aagcagtccttattatttatttatttattt atttatttatttatttatttatttattttt 37920
    agaggtgagagtcttgttatgttgcctagg tgtttgtaacggtgcctggctaacagtcct 37980
    ttcttttgagaagcatatgacctcgggata cacagacattacaatatacacacacaaata 38040
    cacattgtctgtatttatgcagtggagcaa tcataactcactacagcctctaccttctgg 38100
       38110     38120     38130     38140     38150     38160
    |....|....|....|....|....|....|....|....|....|....|....|....|
    actcaagggatcctcccacttcagcctccc aagtggctgggagccaccatactcaaggca 38160
    tgagccaccatactctgctaatcttttatt tttagtagaggtggggttctcagtctttt g 38220
    cttaggctgctctgtcttgaactcctgacc tcaagtggtcctcctatcttgggctcctgt 38280
    ctagctaggattacagggacatgcacacca ctctcagctaattttatctctgcatttctg 38340
    atgaatgagttttttttttttttttttttt ttttttttttagatggtatttcactctgtc 38400
       38410     38420     38430     38440     38450     38460
    |....|....|....|....|....|....|....|....|....|....|....|....|
    gcccaggctggagtgcggtggtgcaatctc agctcactgcaacctctgcctcccagtttc 38460
    aactgattcttgtggctcagcctcccgagc agctgagcagctgggattacaggcatgtgc 38520
    caccatgcccagtaattttgtatttctagt agagatgaggttagccaggctggtctcgaa 38580
    ctcctgacctcaggtgatccgcccaccttg gcctcccgaagtgctgagattgcaggcgtg 38640
    agccacctagcctggccaaatgagttttt  aatttaatttttttctgccccgaaacca   38700
```

FIGURE 11-Z

```
        38710     38720     38730     38740     38750     38760
ccctgaatgagttctattctgcatcagtta accaataatttaatgttgactcaacatcat 38760
ggtggacactagaggcaatagttgggccgg tggtaaatacacagttcagccaacacaagt 38820
acccactggctctcctttgaggagtgccca cttctctgtttctgcttttccgacccagct 38880
tagatgccagccttcccttctctccaac ccactgtactccctccctccttgagcttc 38940
caaagctctcttaaggctctcatactttgc tttgggatataatttgtccctttactggag 39000
        39010     39020     39030     39040     39050     39060
cgtaaatgcctcaagaactgtcagcaagcc ttattcaggtgtggatacctccagagtacc 39060
tgacacggtggaaaaggcacatttgattca ttcactgagaagagaagaggcaaagatgta 39120
gccgctgagtactagctgtgtgaccttggg aaaaataattctttctttggatctctaagt 39180
ttatccataaagcaagagggggggcatcaga ggctctccaaggcagccttctcaacctttt 39240
ttaaaattgggacactcctgatgaatggca ttcccacgtgactcatgcttccatggtgtt 39300
        39310     39320     39330     39340     39350     39360
cagataagatagtctgaattctgcgtaacc ccagctcttcctctctcctctggagagct 39360
tgtccaaaggccagggagcaagagtgacgt tatttatagacataaccttgactccacttc 39420
tcctcatttgtttatttcttttttcttcttc atttatttatttaaggcaaagaaagcattc 39480
tcaagcttcagtagaggtagtggttaaaaa taccagaccagaaaccagagacacttgcct 39540
ttgaatccctctttgccatttctgagtgt agtatccttgggtaagtttgctgagcctca 39600
        39610     39620     39630     39640     39650     39660
gtttccccatctacaacatgggaggatcat catagaactaactttagaagactgtagagg 39660
ggattaaatgcgatcagacaggaaagctct tagcaccatgctgtacatggtaagggctca 39720
gtaaagttgtcaatatctactttgttgtta ttagttacatgttacatgtgacacactaaa 39780
aaattgggatatgatgctgagaccaaaaag taaactcttgattagcttctgccaaatttg 39840
atcttttgtgattttctcacccagtcttgg ggacgctgagccgtggtgaatttctctgct 39900
        39910     39920     39930     39940     39950     39960
ggtggaaatagattcacggatgtagctcaa tcctttcttattttgtttatttattttt 39960
gagatacagtctcactctgttgcccaggct ggagtgcagtggcgcgatctcggctcactg 40020
caagctccgcctcccgggttcacgccattc tcctgcctcagccttctgagtagctggaac 40080
tacaagcgcccgccaccatgctaatttttt gtatttttagtagagacggggtttcactgt 40140
gttagccaggatggtctcgatctcctgagc tagtgatccacctgccttggcctcccaaag 40200
```

FIGURE 11-AA

```
           40210     40220     40230     40240     40250     40260
     ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
     tgctgggattacaggtgtgagccaccgcac ccggccagatgtagctcaatccttctttac  40260
     ctttgttactctatctccactcgctcatcc tattcccctttaattttttctgttttttt   40320
     tttttgtaaagtatcactctcactctcac  ttctttttttctttttgacagggtcttgt   40380
     tctgtcacccaggctggaatgcagtggcac aatcatggttcactgtttcctcaaactccc  40440
     gggctaaagagatcctcctgccttagcctc tcaagtagctgggactacaggctcatacca  40500
           40510     40520     40530     40540     40550     40560
     ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
     acatatctggctaattttcttatatttttg tagaggtggggttttgttatgttgcccagg  40560
     ctggtcttgaactcctggcctcaagtgatc ctcccaccttggcctcacaaagtgctggga  40620
     ttagaggtgtcagccactatgctcggcttg gatgaatttcaaaaattgtaggttgaggcc  40680
     gggcacagtgactcatgcctgtaatcctag cactttaggaggtggtggagggcagatcac  40740
     ttgagcctaggagtttgagaccagcctgga caacatggcaaaaccccatctctatgaaaa  40800
           40810     40820     40830     40840     40850     40860
     ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
     atacaaaaattagccggggatggtggtgca tgcctgtagtcccagctactcaggaggctg  40860
     aggcaggaggatcgcttgaacttgcttgag gtcaaggctgctgtgagccgagatcatgcc  40920
     actgcactccagcctgtgtgacaaagtgag accttgtttcaaaacaacaacaacaacaac  40980
     aacaaactgtatgagcaaaagaagccagat gcaaaaaaatacatacaaaaattccattta  41040
     tatgaaattatggaacaggcaaaactaatc tatgggaagacaggtcatagtcgcatttat  41100
           41110     41120     41130     41140     41150     41160
     ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
     ctttgggaagcagatattgacttggaagca ggagataactttctggaggaaggaaagctt  41160
     caatatcagtgctgcccaatagaaataaaa tgccagctacactcacgcctgtaatcccag  41220
     cactttgggaggccaaggcaggcggatcac gaggtcaggagattgagaccatcctgacta  41280
     acactgtgaaacccccatctctactaaaaat gcaaaaaattggccgggcgtggtggcgggc  41340
     gcctgtggtcccagctacttgggaggctga ggcaggagaatggcatgaacccaggaggcg  41400
           41410     41420     41430     41440     41450     41460
     ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
     gagcttgcagtgagacaagatcgtgccact gcactccagcttgggcaacagagcaagact  41460
     ccgtctcaaaaaaaaaaaaaaagccagct  acagctgtaaaccatatatgtaatttaaaa  41520
     attttctaggaaccacattaaaaagacata aaggccgggcgcggtggctcactcctgtaa  41580
     tcccagcactttgggaggccgaggcaagtg gatcacctgaggtcaggagttggagaccag  41640
     cctggccaacagggtgaaaccatgtctcta ctaaaaatacaaaaattagctgggtgtggt  41700
```

FIGURE 11-BB

```
         41710     41720     41730     41740     41750     41760
ggtgggtgcttgtaatcgcagctactcggg aggctgaggcagaagaatcatttgaacgaa 41760
ggaggtggaggttgcaatgagccaagattg cgccactgcactccagcctgggtgaaagag 41820
taagactccatctcaaaaaaataaaaataa ataaataaataaataaaataaaaagacat  41880
aaaatgaaacaggtgaaatttattttaata atatattcaaaaattacgtttcaacatgta 41940
atcaatgtaaaattattatcactgtatttt acattcattttctgcattctttgatatcca 42000
         42010     42020     42030     42040     42050     42060
atgtatattttgcacttacagcactggtta gtttggccagctgcatctcaagtgctcag  42060
tagccacacgtggtgagtggtcacttttat ggatctgtatcttaatctgggttttagcta 42120
tatataaaaatttatatataaaacttggga ggcactccagcctgggtgacagagcaagac 42180
tttgtttcaaaaaaaaagaaagaaagaaa  ttcatttgtattgttatatgtatctgtcat 42240
ttgtgtgttttttttttttttttttgagat ggagttttgttctgttgcccaggctggagt 42300
         42310     42320     42330     42340     42350     42360
gcagtggcacgatctcgatcttggcttact ccaatctctgcttcctggattcaggcaatt 42360
ctcctgcctcagcctccccagtagctggga ccacaggctcacaccaccacacctggctaa 42420
ttttgtatttttagtagagacagtctcac  gatgttggccaggctggtcttgaactcctg 42480
gcctcaagcaatctgaccacctcagcctcc caaagtgctgggattacaagcgtgagccac 42540
caagcatggtcttttttttcttttttcttttt tttttttcttttttttttgagatggaatctc 42600
         42610     42620     42630     42640     42650     42660
tgtcacccaggctggagtgcagttgcgtga tcttggagtgatcttggcacactgcaacct 42660
ccacctcccggggttcaagtgattctcctgt ctcagcctcccaagtagctgggattacagg 42720
cctgtgccactacacccagctaattttgt   attttagtaaagatggggtttcaccatgt  42780
tggcaaggctggtcctgaactcctggcctc aagtgatccaccccgccttggcctcccaaag 42840
tgttgggcgccggcccttttcattttaca  tagtattccattgtacgaatatatcatagt 42900
         42910     42920     42930     42940     42950     42960
ttatccattctcctgttgatggacgtttgg attacttccaatttctgcttattatgaata 42960
atgctgctatcagtgttcttgaacagtctt taaatagactcatttaaattatttttactg 43020
ttttctggttgttaagataaatccatactc acagaaaaaattcatactcatactaacaca 43080
cacgcctccccaccacgttaaacagttttt actgttttctggttgttaagataaatctat 43140
actcacagaaaaaattcatactcatactaa cacacacgcctccccaccacattaatggtt 43200
```

FIGURE 11-CC

```
       43210     43220     43230     43240     43250     43260
tgatgcaaatggcttatggtttgatgtaaa ttcttttcctccacatatagaatcatgtat 43260
tatcattattaataaaattgtcactttgat ggttcctcccttggttgtctgactcctggg 43320
ggtgctgcgtagctcttaatccttgccctt cttgttgtaaggtctctagaagaccaaaac 43380
tggaaaggatgtagtgatcatctagtccag agaaggcaacgctatagcacaccttctact 43440
gttccatgactacctgcaccaaggcagaca tcactaatcaatcacccgatttctatcctt 43500
       43510     43520     43530     43540     43550     43560
gcccagccctagccactaccagtcattttg gaggtaatttgagaggccaagtagaaaaac 43560
tgaaaccaattttccatctctggaataata tgccactttccattttgcacatgaataaac 43620
tagcgctcagagaggggaagagcctgtttc aaggtcagaggtggagcccaggctcctaa 43680
ctccctaatacttttttccactaagttcaca aactccaaaaactatttccctggtccctga 43740
aaacctgggctctagggagggtgctttgtt ctccagatggggctcagagatgagaacctc 43800
       43810     43820     43830     43840     43850     43860
ccctctagccagcccttcacctttaggtct ggcctaagtgtaagagaagcccctgcctgc 43860
agcctggcacccctttcccaccgtcagcac tgacagacctgcggtttcacttctccaggt 43920
ccacagtttcagtttcccaaaataaacatt aaaaacaataaaacataaaggaggcatcct 43980
cttaacatctttgtctttggcccctgaatt gtagaatgattagttgagcagattaaatca 44040
cagagttaattacagcagagaggtgacttc agatgctgaaaccatagaactctgaagcat 44100
       44110     44120     44130     44140     44150     44160
ccccccttttcaccgacacatcaaaccagcc ctggctgtcattggaagcgacagtgagaaa 44160
gtgagaaagtgggagagtcagcaggtctgg acagactgtgggtgttctcagctgggcaag 44220
cagaatagtttatttaattccctccctgcc agggcagtggggaaagtcgggggtgggga 44280
atggagacagagtgtagcataatgtttggg tcaggtagagctagattttagactggcca 44340
gctgcatgaccttgggcatgtcacttcaga tgtttgagtttcagcttcgtcatctgtaag 44400
       44410     44420     44430     44440     44450     44460
gcaagcacattaatagaacctactacattt aattattgcagtgattcaaatgacttggtt 44460
aaaaagatgtgtatcagccaggcgtggtgg tgcatgcatgtaatcccagcactctgggag 44520
gctgaggcgggaatatcgcttgagctcagg agttcaagaccagcctaggcaaaaaagatg 44580
tatgtaaaactactgtgtctccagattgtc acatctgtgaaagtaggaatcactgtctgt 44640
ctcattcaccatctcatcctccagccctag cacagtgatggtttctaggcaagcacaact 44700
```

FIGURE 11-DD

```
           44710     44720     44730     44740     44750     44760
agtgaggccgggcatggtgactcatgcctg taatcccagcacctggggaggctgaggcag 44760
gcagatcacttgagctcaggaattcgagac cagcctgggcaacatagcaaaactctgtct 44820
ctataaaaaatacaaaaactagctgagtgt ggtggcttgagcctgtagtcgcagctattt 44880
ggggggctgaggtgggaggatcctttgagc ccaggaggcagaggttgcagtgagccgaga 44940
tcatgccactgcattccagcctgagtgaca gagtgagaccctgtctcaaaaacaaacaaa 45000
           45010     45020     45030     45040     45050     45060
caaacaaacaaaaaccaactattgagtact tagtgtaaggtatggtcctgaggataaggg 45060
gtggtggaggagaatgcaaagaggtttaag ggactttcccttagagagctcccattccag 45120
cataacagacattccagaaccatctgtaat aataggtgcattgtgtgtgcattaaatagg 45180
tagataacataaaattatgttcatgatgaa gtgcatgatgggaattctggtatcagactt 45240
gaattcaaatctcagcccctcacttacca cccgtcttatctttattagcaagttgacct 45300
           45310     45320     45330     45340     45350     45360
ctcaatgctttcatttcctgatctgtaaaa tagcgacctgcctcagagagctgttgcaag 45360
gattgaatgagtttcccaacgcaaagtgcc tgagacacaataattgctcagagtctgact 45420
ctgttgcccaggcggggagtgcagtggcagg atctggctcgctgcagcctctgcctcctg 45480
ggttcaagtgattctcccacctcagcctcc ccagtagctgggattacaggcatgtgccac 45540
cacgcctggtcaattttttgtattttttcgta gagacggggttttgccatgttggccaggct 45600
           45610     45620     45630     45640     45650     45660
ggtctcaaactcctaacctcaagtgatctg tccacctcagcctcccaaaatgctaggatt 45660
acaggcgtgagtcagcacaccggcacccc catagtgcttttgatggactacctttactt 45720
tcccatagtgctttagagtgtctaaggtgc tttcaaatacatgatctcacttaagtcttg 45780
cagcaactccgaaagtaaatggaagctcag aaggctaagtggtgtatccctagaaccacc 45840
cgaccagaaacagtggtagtcccaagacca gcatatggatctttggactctcagtcaagt 45900
           45910     45920     45930     45940     45950     45960
gctttcattactccagctcatagccttctg gttgagtccagaaatctgagagaaggaaaa 45960
aaaaagagagaaaaattaggacaaaaaagt gagggactgaagacctatgtccacacaaaa 46020
acctgagctttaatcataattgccagaact tgaaggcaaccaagatgtctttcaggaggt 46080
gaagggatgcataaaccgtggtacatctag agcacagactattatgcagcactaaaaaca 46140
gacaagctatcaagctatggaaagacatag acggggtcaggcgaggtggctcacacctgt 46200
```

FIGURE 11-EE

```
         46210     46220     46230     46240     46250     46260
   ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
   aatcccagcactttgagaggctgaggcagg tggatcacttgaagctaggagttccagacc 46260
   agcctgggcaacatggtgcaaccctgtctc tacaaaaaatacaaaaattagccaggggcg 46320
   gtggtgtgtgcctgtagtcccagctattct gtagtcccagctgttggggaggctgaggtg 46380
   ggaggattgcttgagcctgagaggttgagg ctgcagtgagcctgaacatgccactgcact 46440
   ctagcctgggcgacagagtgaaaccttgtc tcaaacaaacaaacaaacaaacgaaacaaa 46500
         46510     46520     46530     46540     46550     46560
   ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
   cgagcaaaaaaacccaggaaacaaaaaaat aaaacccacacacaaaaaaagccaccatag 46560
   aggaatcttaactgtgtgttactaagtgaa agaagccaatctgaaacagctactactgta 46620
   tgattcaagctatacgacgttcttttttt  ttgagacgaagtcttgctctgttgcccagg 46680
   ctggagcgcaacggggcgatcttggctcac tgcaagctctgcctcctgggttcacgccat 46740
   tctcctgcctcagcctcccgagtagctgga actaaaagcgccgctaccatgcccagcta 46800
         46810     46820     46830     46840     46850     46860
   ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
   atttttgtatttttagtagagacggggtt  tcatcatgttagccaggatgggctcgatct 46860
   cctgacctcgtgatccgcctgcctcggcct cccaaagtactgggattacaggcgtgagcc 46920
   accgcgtccggcctatatgacattcttgaa aagagaaaactatggagagtgaaagatcag 46980
   gggttgtcaggggttggggagggagaac   aaataggtggagcacagagaatgtttagga 47040
   cagtgaaactactctgtatgacagtataat gggagatacatgtccttatacatttgccca 47100
         47110     47120     47130     47140     47150     47160
   ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
   aacccatagaatgtataaaaccaagagtga actctaaactatggactctgggtgataaca 47160
   atgtgtcagtataggttcaccaattgtaac aaatgtaccactctggtgggggatgttgac 47220
   agtgggaaaggttacacacatgtggggtca ggcggtatggggaaatctctgtactttctc 47280
   ctcaataaaaataaagtctacttttaggc  tgggcatagtggcttatatttgtaatccca 47340
   gcactttgggaggccgtggtggcagaggat tgcttgagtgcaggagcttgagaccagcct 47400
         47410     47420     47430     47440     47450     47460
   ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
   gggcaacatagttagaccccgttctgcaaa acaaaacgaaacaaaaattagctgggcatg 47460
   gtggcgtgcatgtgtagtcccagctatttg ggaggctgcattgggaagactgcttgagcc 47520
   caggaggttgaggctacagtgaaccctcat cgtgccaccgcgctccagcctgggcaacag 47580
   agtgagaccctgcctcaaaaaaagaaagaa aaaataaagtatatatatataggtatatat 47640
   atatattttttaagtgggggaagtttgta  aaatgggctgattataaatgcatggctctt 47700
```

FIGURE 11-FF

```
           47710     47720     47730     47740     47750     47760
     |....|....|....|....|....|....|....|    |....|....|....|....|....|....|
     aatcagcttacagtaaattttttccttgtct  tgcatggacaagaaatgggaagttccaggt  47760
     aattcagggctttgcttggatattgcattt   tcttttgttctttttttttctgagacggag  47820
     tctcattctgtcacccaggctggagtgcag   tggtgcaatcttagctcacttcaacctccg  47880
     tctcctgagttcaagcaattctcctgcctc   agtctccccagtagctgggattacaggcgt  47940
     gcgccaccacgccaggctaattttttgtatt  tttagtagagacgggtttcaccatgttgg   48000
           48010     48020     48030     48040     48050     48060
     |....|....|....|....|....|....|....|    |....|....|....|....|....|....|
     ccaggtggtctcgaactcctgacctcgtga   tctacccacctcggcctcccaaagtgctgg  48060
     gattacaggcgtgaatcactgcgcccggcc   aatattgcattttcaaagaatgagaacact  48120
     gtgaaatactctgcacgctaaaaccacatg   gactataatttaatctttaattttgttgtt  48180
     gtcattctcaaaggctcttcaatatatctt   aaagctgtgtttctccaagagtggccaagg  48240
     aaaaccctcagctctcagccttctcatctg   atagaggtgtctgttcaaaaactgccattt  48300
           48310     48320     48330     48340     48350     48360
     |....|....|....|....|....|....|....|    |....|....|....|....|....|....|
     tctgagcccccatccacccctagtccactt   gacctacagttttagagtagtgaaagtcaa  48360
     aatatgaacgttaattatcattgtacttaa   gagatgcagacattctgcttaaatgagagt  48420
     tctgtatcatagagtagactcatttacctc   atctccttcaagtctttgctaaaacgtctc  48480
     cctccccatgagaatgttgttgatttaaaa   ttgcatctcaggccaggtgtggtggctcac  48540
     gcctgtaatcccaacactttcaagggcaga   ggtgggcagatcacctgaggtcaggcgttc  48600
           48610     48620     48630     48640     48650     48660
     |....|....|....|....|....|....|....|    |....|....|....|....|....|....|
     aagaccagcctggccaacacggcgaaaccc   catctctactaaaaatacaaaaaattagtc  48660
     aggagtgatggtggatgcctgtaaccccag   ctactggggaggctgaggcaggagaatcac  48720
     ttgaatccaagaggcagagattgcagtgag   ccgagatcatgccactgcactgcagcctgg  48780
     gtgacagagcaagactccatctcaaaaata   tatatatatataaaatttcatctcaccttc  48840
     ttcccaatagtacccaccctccctatcacc   cttccttctctgtggcacctacaacatcta  48900
           48910     48920     48930     48940     48950     48960
     |....|....|....|....|....|....|....|    |....|....|....|....|....|....|
     actgaacacaccatttatttatctattgtt   tattcattcattcactcattcattcattga  48960
     ctcattcattcattcatttacttgtatgac   tctcatctctagaatgcaagctttacaaag  49020
     gcagctgctgggactacaacacctaggaca   gtgtctagtacatagaagatgttcggtaaa  49080
     tacctgtgccaagttgcataatatcatttg   cccactgtctttctcaagaggattttttaa  49140
     aaactataaagcaaattcttcttttattct   ttgagtgatgttctgtgtgtgtagtaccag  49200
```

FIGURE 11-GG

```
           49210     49220     49230     49240     49250     49260
      ┴┴┴┴┴┴┴┴┴┴┴┴┴┴┴┴┴┴┴┴┴┴┴┴┴┴┴┴┴┴┴┴┴┴┴ ┴┴┴┴┴┴┴┴┴┴┴┴┴┴┴┴┴┴┴┴┴┴┴┴┴┴┴┴┴┴┴┴┴┴┴
      agaaaaagagctggaaccacatcctctaat ctcttaattctgaagtctgggcctgttgct 49260
      ctaaagatcattttttccttaataccactga gatcctcaatttactatgaggatcatgagt 49320
      ttacaactgcattgtcctgtgagggctacc tctagaagggcttgtcgccctattgtgaa 49380
      caaagtggactgaagctgctgcagctgaga tacacctgcactgaaagaggatttgtctaa 49440
      gtctaacccatgttactgtgatacaaacaa gctactgaccaaaagaggtagacgcttcct 49500
           49510     49520     49530     49540     49550     49560
      ┴┴┴┴┴┴┴┴┴┴┴┴┴┴┴┴┴┴┴┴┴┴┴┴┴┴┴┴┴┴┴┴┴┴┴ ┴┴┴┴┴┴┴┴┴┴┴┴┴┴┴┴┴┴┴┴┴┴┴┴┴┴┴┴┴┴┴┴┴┴┴
      cctcagattctgaatgaatatgctaataca tggatcctatctcaagctacttcttacaca 49560
      gcattggctgactctgaacagatgccttta cccatttccttttttttttttaatccaaaa 49620
      tgtgtttattgagatggtttcccactcatc ttgattcagagtgctttgggtgctgcttcc 49680
      tcctgaaggaacatccttctgtagccttcc ttttcctcctgtaggctggcagagaacagt 49740
      ggagcaggcaacacacaaaactaccgtttg tgcatggctacagaccatggtgatttata 49800
           49810     49820     49830     49840     49850     49860
      ┴┴┴┴┴┴┴┴┴┴┴┴┴┴┴┴┴┴┴┴┴┴┴┴┴┴┴┴┴┴┴┴┴┴┴ ┴┴┴┴┴┴┴┴┴┴┴┴┴┴┴┴┴┴┴┴┴┴┴┴┴┴┴┴┴┴┴┴┴┴┴
      gcatcctgggcatgtcatatccatgaagta ggaatcgggactctgcaccaggcgtttctt 49860
      cttctgtttcctcttctcttctggagaagg atgaaggagatccctgtcgagaggcatgtt 49920
      ctcgtgggtaggtcgccactgccggaaagg acccatttcctatccttcaagctcatctgc 49980
      ccagcagcaccagcacacaaaccaaagtcc aggaacactggaagatccctactccccgca 50040
      cctctccaatgacccttttttaagttcagac ctaagaagagtcacctccctaataccgcag 50100
           50110     50120     50130     50140     50150     50160
      ┴┴┴┴┴┴┴┴┴┴┴┴┴┴┴┴┴┴┴┴┴┴┴┴┴┴┴┴┴┴┴┴┴┴┴ ┴┴┴┴┴┴┴┴┴┴┴┴┴┴┴┴┴┴┴┴┴┴┴┴┴┴┴┴┴┴┴┴┴┴┴
      aggctacctgctcaccctcatctgtgtctc tgctacaacacaaactggaatgcttttgtg 50160
      tcggaatggtaagaaatgccttgtgtgggt ggccctccagtccccagtccaggggatgct 50220
      gagaaactgtggggcagagtaggggacaca aacaggaaaaagcaagtttgtttctagtgt 50280
      tatgctcacagggtggcaggatatacctgc tgagcattcccagaaggtccccaaggaaac 50340
      cattactgtaagtctctcactttcttctct gcctgatggttggggtggggagagggaagg 50400
           50410     50420     50430     50440     50450     50460
      ┴┴┴┴┴┴┴┴┴┴┴┴┴┴┴┴┴┴┴┴┴┴┴┴┴┴┴┴┴┴┴┴┴┴┴ ┴┴┴┴┴┴┴┴┴┴┴┴┴┴┴┴┴┴┴┴┴┴┴┴┴┴┴┴┴┴┴┴┴┴┴
      agggctatcaagagggggatgggcacccctt ccagaggtcagagttatgatgcccaggaat 50460
      aaaaggtgttgaattcaggatggaatgtga aggtgaacagcaaagggcttgtcaacatgg 50520
      gttgtcactggattacaccggatggattaa ggtagggatgggggaaggagtagaaggtga 50580
      gttgggagggaggggcttgtgtggcactga gaccccagcagggatggggagaagggtg 50640
      ttggccacctaagcttcctggtttgatcct ttttggctggtttcagctggggaagtgaa 50700
```

FIGURE 11-HH

```
           50710     50720     50730     50740     50750     50760
         ....|....|....|....|....|....|  ....|....|....|....|....|....|
         gggtcctaaggcttggatatggagaggtgg   gaatatggagaggtggggatatggagaggc  50760
         ggggataaggagaggtggggataaggagag   tggccccgcagctccctggtgaaccagaa  50820
         tactttctcagggttgttcccaggctggag   ggagggaattttaggggtacgtaaggtgac  50880
         tccaaggagccttgggtgcaagtactgggg   gatcccagagacccagaagatgggggtaga  50940
         aaggaaggtgtttgccttcacggggagtag   cctcaaaataagagggactgagggaagtca  51000
           51010     51020     51030     51040     51050     51060
         ....|....|....|....|....|....|  ....|....|....|....|....|....|
         ttccaaatgcagtgggtaggtagtttaggc   tcttccaatgggatggggtggagcttagac  51060
         ctctgcaaaagaaggggggtcattcggaggg  gacggtgcacagctgaggcgttgggctcct  51120
         aaactggaaacaggaggctctaagaggcac   tgccttttcctccagcctcggtgtggtggg  51180
         ggtggtgagtgtctggaaccgggtttcccg   aatcaggacaggagtctgaatggatctcac  51240
         aaaaaccggccagggagggagagaaccagg   ggagactcctcacaccgggaggtggggtg   51300
           51310     51320     51330     51340     51350     51360
         ....|....|....|....|....|....|  ....|....|....|....|....|....|
         gcggcaaactgagaacccgggcttggggcg   cgggattttctcaacagaccatagggtcca  51360
         ctaatgtggacggcagggatttggggaaac   taaggggactctcactttggacaccaagg   51420
         gctgaggacggattggggaagaggatacgg   tttctactggggtgctgatggaggttcccc  51480
         actcgggacgcgaggcactgagtgggtccc   ccaaactggatatgggatcctgggaacgga  51540
         gcgagggctctaaattagagccctggggtg   ggggtgggggctgtaaattaggttgggag   51600
           51610     51620     51630     51640     51650     51660
         ....|....|....|....|....|....|  ....|....|....|....|....|....|
         gaaactgggggctctgagggcggcttctcg   ctccgactggggaaatggagcatgtgggga  51660
         ctggggagcactagggctatctcccgcccg   acccgaggagattggggttctcttcaattc  51720
         tggacagcagggacctgagagggaagaccg   gggggttcccgatccggaaccgagctacc   51780
         ttgaaggcaccgggaagcgcttcattccgg   gagggcgttcccgcggccggccccgcgc    51840
         cggggtgggtgggggtgcggccgcgccct    ggtccggccgcacgggattcggggtc      51900
           51910     51920     51930     51940     51950     51960
         ....|....|....|....|....|....|  ....|....|....|....|....|....|
         tcgctcggcccggagacccaggagccccg    cgggaaggggtcccggcgccgccgcctcc   51960
         gcgggcgcccgggctcgcggcgagcgcgg    ggctttatgcgcgcagggcggcggggggag  52020
         gagccggcaggtcggccccggcgggccct    cccctcggccgtcccgccgccgccga      52080
         gcggggtcggggaggggggcagcatggcct   gtccgtcggccccttcgccgcgctcctc    52140
         atctgccccgcgccgagcgccgccgcgcc    gccgccgccgctccgctgcccgcgccg     52200
```

FIGURE 11-II

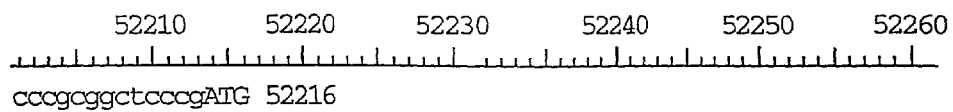
FIGURE 11-JJ

```
   1 gatcctggaa ggtgggcagc aactggcaca cctcaagatg tcccttagtc tggaggtggc
  61 tacatacagg tacacagtgc tgactgtcct cggcttcttc tgcggcccag aaacttggct
 121 ttgtactttc tgtgactgtc agctatcgct ttgtaaaact gtcctattta tgtgtatttg
 181 tgtatgtacc acatgtgtac aggtgtccta agagcccaga ggaaggcaat gggttgtgtg
 241 cagctccaca ctggtgctgt gaaccaaacc cctgttctca gcaaaaagca gcaagcattc
 301 ttaaccactg agccgtctgt ccagccctcg gagtcactta aaacgtttta taacatttac
 361 ttatgtaatg tatttgtctg ggatggaggc ttatgagtcc cagaggtgga acaggtctgg
 421 cttggcagct tggcccaccc aggttcagga ccagaagaga cggtgatgct taaaaagaca
 481 gctcagtctt cagggaggag accagacaga tgagttcttt ggaaggcagg caatctccag
 541 tgtctatgcc aacatcctgg ggacacctgg gcagtctcag aagagaggcc ttgcaggttt
 601 gcctgatcat gctaacctgc cacctcgcct gggcctcagg tgttttgggt aagagctggc
 661 ctcctagctt ttttgcttcc tttcaagccc tcatgtcact ggtcctgccc cagttctctg
 721 ccctttttctt ggctgcctca ggacggctga gtggaacggc tctggtggta tgttcacagc
 781 ctctgtctgt gtctcttgtg ggaaaaggcc ccagttggag tcccacggtt gagggctgag
 841 gatatcactc cagagtatgg ggctaggaca ggatgccccc cttttccaga atccagcggt
 901 aaagaggaaa gacagagaca ggtctaggag aggagctgga gggcccagag aaggacagcc
 961 agtgagtgtc taggaaagac tgaatgcata aggcaggatg ccgcatgagg acagaggaaa
1021 gggtactttg agaaccagat gtgctcagag gccatgaatg gaaacagact agttccgaat
1081 cccatgtgaa ctgatttccc tcatctcctt caatcagctc cataggccac tgaggcaggg
1141 ccatgaacgt taagacctct gccctgaaga gtttgtgatc ctgagatgag ggctttagcc
1201 ccagtcagtc ctctgagggg aagggtccag gcagctctga ggaatgtaac cactggcgtt
1261 tgaggtctga aaaggatttg agaagggga gctgaattca tttgctttg tctgttacca
1321 gctctggggg cagagagaga gccatcccct gggaacagcc tgagaattcc cacttcccct
1381 gaggagccct cccttcttag gccctccaga tggtagtgtg acaaaaggc aataattagc
1441 atgagaatcg gcctccctcc cagaggatga ggtcatcggc cttggccttg ggtggggagg
1501 cggagactga tctgaggagt ctgatataag tgttagcaat tcatttggcc ctgcctccga
1561 ctgtgggaat ctgcatgtgg ggtctccctg tgtctcaaat atgggttggc taagtatata
1621 tctgtgggta tatgactgtg tggctttat atgacaatgg tcacaataga gattgatcct
1681 gcagtggcag gacatgctac ctcagctgga gctgaccctä tctccccact ccccaccagg
1741 actctgctgg aggctgagaa ctctcggttg cagacacctg gacgaggttc ccaggcttct
1801 cttggctttc tgggtaagag gcggagccaa ctgctctcct tggaagatcc
```

FIGURE 12

ENRICHED PREPARATION OF HUMAN FETAL MULTIPOTENTIAL NEURAL STEM CELLS

This application claims the benefit of U.S. Provisional Patent Application Ser. No. 60/173,003, filed Dec. 23, 1999, which is hereby incorporated by reference.

The invention was made with government support under grant numbers RO1 NS29813 and RO1 NS33106 awarded by the National Institutes of Health. The government has certain rights in this invention.

FIELD OF THE INVENTION

The present invention relates generally to a method of separating cells of interest, in particular multipotential neural progenitor cells.

BACKGROUND OF THE INVENTION

Throughout this application various publications are referenced, many in parenthesis. Full citations for these publications are provided at the end of the Detailed Description. The disclosures of these publications in their entireties are hereby incorporated by reference in this application.

The damaged brain is largely incapable of functionally significant structural self-repair. This is due in part to the apparent failure of the mature brain to generate new neurons (Korr, 1980; Sturrock, 1982). However, the absence of neuronal production in the adult vertebrate forebrain appears to reflect not a lack of appropriate neuronal precursors, but rather their tonic inhibition and/or lack of post-mitotic trophic and migratory support. Converging lines of evidence now support the contention that neuronal and glial precursor cells are distributed widely throughout the ventricular subependymal of the adult vertebrate forebrain, persisting across a wide range of species groups (Goldman and Nottebohm, 1983; Reynolds and Weiss, 1992; Richards et al., 1992; Kirschenbaum et al., 1994; Kirschenbaum and Goldman, 1995a; reviewed in Goldman, 1995; Goldman, 1997; Goldman, 1998; Goldman and Luskin, 1998; and Gage et al., 1995). Most studies have found that the principal source of these precursors is the ventricular zone (Goldman and Nottebohm, 1983; Goldman, 1990; Goldman et al., 1992; Lois and Alvarez-Buylla, 1993; Morshead et al., 1994; Kirschenbaum et al., 1994; Kirschenbaum and Goldman, 1995), though competent neural precursors have been obtained from parenchymal sites as well (Richards et al., 1992; Palmer et al., 1995; Pincus et al., 1998). In general, adult progenitors respond to epidermal growth factor (EGF) and basic fibroblast growth factor (bFGF) with proliferative expansion (Reynolds and Weiss, 1992; Kilpatrick and Bartlett, 1995; Kuhn et al., 1997), may be multipotential (Vescovi et al., 1993; Goldman et al., 1996), and persist throughout life (Goldman et al., 1996). In rodents and humans, their neuronal daughter cells can be supported by brain-derived neurotrophic factor (BDNF) (Kirschenbaum and Goldman, 1995a), and become fully functional in vitro (Kirschenbaum et al., 1994, Pincus et al., 1998a, and Pincus et al. 1998b), like their avian counterparts (Goldman and Nedergaard, 1992).

A major impediment to both the analysis of the biology of adult neural precursors, and to their use in engraftment and transplantation studies, has been their relative scarcity in adult brain tissue, and their consequent low yield when harvested by enzymatic dissociation and purification techniques. As a result, attempts at either manipulating single adult-derived precursors or enriching them for therapeutic replacement have been difficult. The few reported successes at harvesting these cells from dissociates of adult brain, whether using avian (Goldman et al., 1992; 1996c), murine (Reynolds and Weiss, 1992), or human (Kirschenbaum et al., 1994) tissue, have all reported <1% cell survival. Thus, several groups have taken the approach of raising lines derived from single isolated precursors, continuously exposed to mitogens in serum-free suspension culture (Reynolds and Weiss, 1992; Morshead et al., 1994; Palmer et al., 1995). As a result, however, many of the basic studies of differentiation and growth control in the neural precursor population have been based upon small numbers of founder cells, passaged greatly over prolonged periods of time, under constant mitogenic stimulation. The phenotypic potential, transformation state and karyotype of these cells are all uncertain; after repetitive passage, it is unclear whether such precursor lines remain biologically representative of their parental precursors, or instead become transformants with perturbed growth and lineage control.

In order to devise a more efficient means of isolating native, unpassaged and untransformed progenitor cells from brain tissue, a strategy by which brain cells could be freely dissociated from brain tissue, then transduced in vitro with plasmid DNA bearing a fluorescent reporter gene under the control of neural progenitor cell-type specific promoters was developed (Wang et al., 1998). This permitted isolation of the elusive neuronal progenitor cell of the CNS, using the T$\alpha$1 tubulin promoter, a regulatory sequence expressed only in neuronal progenitor cells and young neurons.

However, T$\alpha$1 tubulin-based separations are limited in that they yield committed neuronal progenitors, and not the more multipotential neural progenitors, such as neural stem cells, of the adult brain, which can give rise to neurons, oligodendrocytes, and astrocytes. The existence of these neural stem cells has been reported in a number of studies of rodents (reviewed in Weiss et al., 1996), and precursors competent to generate both neurons and oligodendrocytes have been demonstrated in adult humans (Kirschenbaum et al., 1994; reviewed in Goldman, 1997). In rodents, these cells have been clonally expanded using repetitive passage and mitogenic stimulation, as described above. Nonetheless, native adult neural stem cells have never been separated and purified as such, in rodents or humans.

A strong need therefore exists for a new strategy for identifying, separating, isolating, and purifying native multipotential neural progenitor cells from brain tissue.

SUMMARY OF THE INVENTION

To this end, the subject invention provides a method of separating multipotential neural progenitor cells from a mixed population of cell types, based upon cell-type selective expression of cell-specific promoters. This method includes selecting a promoter which functions selectively in the neural progenitor cells and introducing a nucleic acid molecule encoding a fluorescent protein under control of said promoter into all cell types of the mixed population of cell types. Only the neural progenitor cells, but not other cell types, within the mixed population are allowed to express the fluorescent protein. Cells of the mixed population of cell types that are fluorescent, which are restricted to the neural progenitor cells, are identified and the fluorescent cells are separated from the mixed population of cell types. As a result, the separated cells are restricted to the neural progenitor cells.

The present invention also relates to an isolated human musashi promoter.

Another aspect of the present invention is an enriched or purified preparation of isolated multipotential neural progenitor cells.

A promoter is chosen which specifically drives expression in multipotential neural progenitor cells but not in other cells of the nervous system. The fluorescent protein will therefore only be expressed and detectable in cells in which the promoter operates, i.e. those cells for which the promoter is specific.

The method involves the introduction of a nucleic acid encoding the fluorescent protein, under the control of the cell specific promoter, into a plurality of cells. Various methods of introduction known to those of ordinary skill in the art can be utilized, including (but not limited to) viral mediated transformation (e.g., adenovirus mediated transformation), electroporation, and liposomal mediated transformation.

After cell specific expression of the fluorescent protein, such as green fluorescent protein (GFP), the cells expressing the fluorescent protein are separated by an appropriate means. In particular, the cells can be separated by fluorescence activated cell sorting. The method of the subject invention thus provides for the enrichment and separation of the multipotential neural progenitor cells.

Contemporary approaches toward the use of neural precursor cells have focused upon preparing clonal lines derived from single progenitors. However, such propagated lines can become progressively less representative of their parental precursors with time and passage in vitro. To circumvent these difficulties, the method of the subject invention provides a strategy for the live cell identification, isolation and enrichment of native multipotential neural progenitor cells, by fluorescence-activated cell sorting of human ventricular zone cells transfected with fluorescent protein, driven by the multipotential neural progenitor cell-specific musashi promoter or nestin enhancer. Using this approach, multipotential neural progenitor cells can be identified and selectively harvested from a wide variety of samples, including embryonic and adult brain of avian, mammalian, and human origin. This approach allows for the enrichment of neural precursors from both adults and embryos, with a yield substantially higher than that achievable through standard techniques of selective dissection and differential centrifugation. The musashi protein is a RNA-binding protein expressed by neural progenitors, including cycling cells of both the ventricular and subventricular zones (Sakakibara et al., 1996). During development, it is expressed by neural and neuronal progenitor cells of the ventricular zone, such that musashi expression falls sharply to undetectable levels when a cell commits to neuronal phenotype, at which point expression of the related Hu proteins rise (Sakakibara et al., 1997). Nestin is an intermediate filament expressed by neural stem and progenitor cells; the second intronic enhancer of nestin directs its transcription to neural progenitor cells of the fetal neuroepithelium. As a result, the musashi promoter and the nestin enhancer were chosen for this study for their ability to target transgene expression to multipotential neural progenitor cells.

Extension of this approach to include fluorescent transgenes under the control of stage- and phenotype-specific promoters (both of which are intended to be covered by reference to "cell-specific" promoters herein) allows even more specific separations to be performed, for example, of multipotential neural progenitors over a range of developmental stages. This strategy permits sufficient enrichment for in vivo implantation of the defined and separated progenitor pools, as well as for in vitro analyses of phenotypic specification and growth control.

By providing a means of identifying multipotential neural progenitor cells while alive, even when present in small numbers in mixed populations, the use of fluorescent transgenes driven by cell type-selective promoters such as the musashi promoter and the nestin enhancer will allow the specification of phenotype to be studied and perturbed on the single cell level, an approach that had previously only been feasible on larger populations. Indeed, when used in conjunction with post-transfection fluorescence-activated cell sorting (FACS), this strategy may permit the enrichment of any cell type for which stage- or phenotype-specific promoters are available. For instance, similar GFP constructs based upon early neuronal promoters, such as T$\alpha$1 tubulin (Wang et al., 1998), might similarly permit the enrichment of neuronal and oligodendrocytic precursors as well as multipotential neural progenitors from adult brain tissue. As a result, spectrally distinct GFP variants with non-overlapping emission spectra (Heim and Tsien, 1996), each driven by a different cell-specific promoter, will allow concurrent identification of neuronal precursors, oligodendrocytic precursors, and multipotential neural progenitors in vitro. Multi-channel cell sorting based upon the concurrent use of several lasers with non-overlapping excitation lines, such as Ar—K and He—Ne, should then allow the separation and simultaneous isolation of several distinct precursor phenotypes from a given brain sample.

The method of the present invention provides a new strategy for the isolation and purification of multipotential neural progenitor cells, especially neural stem cells, from the adult brain. These cells may be used in both basic analyses of precursor and stem cell growth control, as well as in more applied studies of their transplantability and engraftment characteristics. Generally, by providing a means to identify and enrich neural precursor cells from adult brain, this strategy may allow a significant acceleration in the study of precursor and stem cell biology, as well as providing native unpassaged adult precursor cells in sufficient number for implantation studies. As such, this approach may spur the development of induced adult neurogenesis as a viable therapeutic modality for the structural repair of the damaged central nervous system, whether in the brain or spinal cord.

BRIEF DESCRIPTION OF THE DRAWINGS

The file of this patent contains at least one drawing executed in color. Copies of this patent with color drawings will be provided by the Office upon request and payment of the necessary fees.

These and other features and advantages of this invention will be evident from the following detailed description of preferred embodiments when read in conjunction with the accompanying drawings in which:

FIGS. 2A-E show fetal human 21 week gestational age brain sections with neural progenitor cells labeled by anti-human nestin (red) and musashi-1 (green) antibodies. FIGS. 2D-E are a 40× magnification of the ventricular zone and the border of the subventricular zone and intermediate zones, respectively. In FIGS. 2D and E, the arrowheads show the frequent musashi$^+$/nestin-cells, particularly at the adluminal surface of the ventricular zone, whereas the arrows show double-labeled cells, more common in the deeper layers of the ventricular zone and nascent subventricular zone. At this gestational timepoint, musashi-1 immunoreactivity was expressed by virtually all cells of the ventricular zone, while nestin was less ubiquitously expressed. In contrast, nestin expression was most predominant within the basal aspect of the ventricular zone, and throughout the subventricular zone. A preponderance of musashi+/nestin+ double labeled cells was noted at the interface of these two layers, with many apparent migrants. These double-labeled cells became increasing scarce with greater distances from the ventricular wall, as nestin+/musashi-cells began to predominate.

FIGS. 3A-F show AdP/Musashi.hGFP+ cells which are mitotically competent and phenotypically uncommitted. FIG. 3A shows that at 8 DIV, 96.1% of AdP/Msi:hGFP+ (green) cells are co-labeled with nestin antibody (red). FIG. 3B shows that none of the AdP/Msi:hGFP+ (green) cells express early neuronal marker of TUJ-1 protein (red). FIG. 3C shows that approximately 39% of AdP/Msi:hGFP+ (green) cells co-express GFAP (red) and 93.25% of cells are mitotically active, as indicated by incorporation of BrdU (blue). FIGS. 3D-F are the corresponding phase contrast views for FIGS. 3A-C, respectively.

FIG. 4A shows that at 4 DIV, 98.95% of Ad.E/Nestin:EGFP+(green) cells are co-labeled with nestin antibody (red). FIG. 4B shows that approximately 8.93% of Ad.E/Nestin:EGFP+ (green) cells are co-labeled with GFAP (blue) and 3.12% with TUJ-1 antibody (red). FIG. 4C shows that approximately 61.6% of Ad.E/Nestin:EGFP+ (green) cells incorporated BrdU (blue). FIGS. 4D-F are the corresponding phase contrast views for FIGS. 4A-C, respectively.

FIGS. 5A-B show sort profiles of cell size (FSC) vs. GFP fluorescence intensity (FL1) of AdCMV.LacZ infected, non-fluorescent control cells and AdP/Msi.hGFP infected cells, respectively. Approximately 3.95% of the sorted population achieved an arbitrary threshold of fluorescence intensity for AdP/Msi.hGFP+ cells. FIGS. 5C-D show the sort profiles of AdCMV.lacZ infected, non-fluorescent control cells and AdE/Nestin.EGFP infected cells, respectively. Approximately 8.1% of the cells in this representative sample achieved the control-calibrated threshold of fluorescence intensity for AdE/Nestin.EGFP+.

FIG. 6A shows GFAP+ astrocytes (green) with TuJ1+ neurons (red) generated from AdP/Msi.hGFP+ cells, 5 days after FACS. By this time, AdP/Msi.hGFP+ sorted cells no longer express musashi-driven GFP. FIG. 5B shows the presence of GFAP+ (blue) and TuJ1+(red) cells generated from AdE/Nest.EGFP+ cells after 5 days post sort. In contrast to the relatively rapid transcriptional inactivation of musashi promoter-driven GFP, these AdE/Nest.EGFP+ sorted cells still expressed GFP, and continued to do so for almost 2 weeks in vitro.

In FIG. 9A, in the plasmid separation cassette, EGFP was placed 3' to the heat shock protein-68 basal promoter, and this was placed under the regulatory control of the nestin second intronic enhancer. In FIG. 9B, adenoviral E/nestin:EGFP was constructed to include E/nestin:hsp68:EGFP in a ΔE1 adenovirus. In FIG. 9C, in the plasmid separation cassette P/musashi:hGFP, hGFP was placed 3' under the regulatory control of the nestin second intronic enhancer. In FIG. 9D, adenoviral AdP/musashi:hGFP was constructed to include P/musashi:hGFP in a ΔE1 adenovirus.

FIGS. 10A-F show human AdE/Nest.EGFP+ and AdP/Musashi.hGFP+ cells engrafted into the fetal rat brain differentiate as neurons, astrocytes, and oligodendrocytes. FIGS. 10A-C show human AdE/Nest.EGFP+ transplanted cells that are identified by the anti-human antibody (ANA) (green). The arrowheads indicated double-labeled cells. In FIG. 10A, neurons are labeled with anti-Hu antibody (red), while the human AdE/Nest.EGFP-derived cells are labeled with ANA (green). Double-labeling (yellow) indicates AdE/Nest.EGFP-derived human neurons in the rat neocortical parenchyma. In FIG. 10B, oligodendrocytes are labeled with CNPase (red), permitting the identification of AdE/Nest.EGFP-derived human oligodendrocytes (yellow). In FIG. 10C, astrocytes are GFAP labeled (red). In FIGS. 10D-F, human AdP/Msi.hGFP+ transplanted cells are identified by the anti-human antibody or BrdU (green). The arrowheads indicate double-labeled cells. In FIG. 10D, neurons are labeled with anti-Hu antibody (red) and the human AdP/Msi.hGFP+ generated neurons are co-labeled with ANA (arrowheads). In FIG. 10E, oligodendrocytes are labeled with CNPase (red).In FIG. 10F, astrocytes are GFAP labeled (red).

FIG. 11 shows a nucleotide sequence of a human musashi promoter (SEQ. ID. No. 1).

FIG. 12 shows a nucleotide sequence of a human nestin enhancer (SEQ. ID. No. 2).

DETAILED DESCRIPTION OF THE INVENTION

Figure 1:
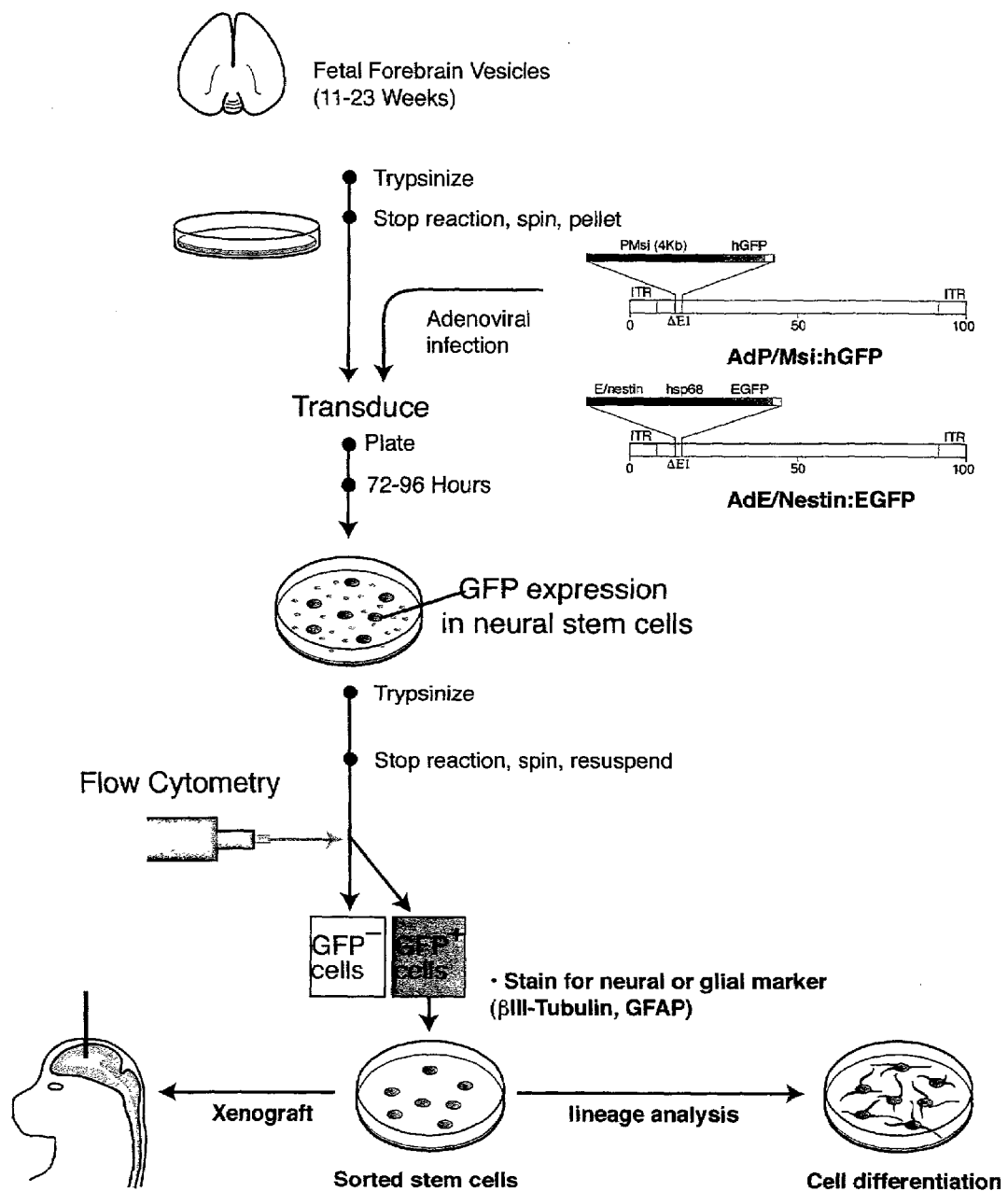
FIG. 1 shows a schematic outlining the strategy by which AdE/Nest:EGFP and AdP/Msi:hGFP-based fluorescence activated cell sorting (FACS) was used to extract neural stem cells from the fetal human forebrain. The isolated cells were characterized for their lineage potential in vitro. In addition, their phenotypic potential was also assessed upon in vivo xenograft into telencephalic vesicles of E17 and P2 rats.
Figure 4:
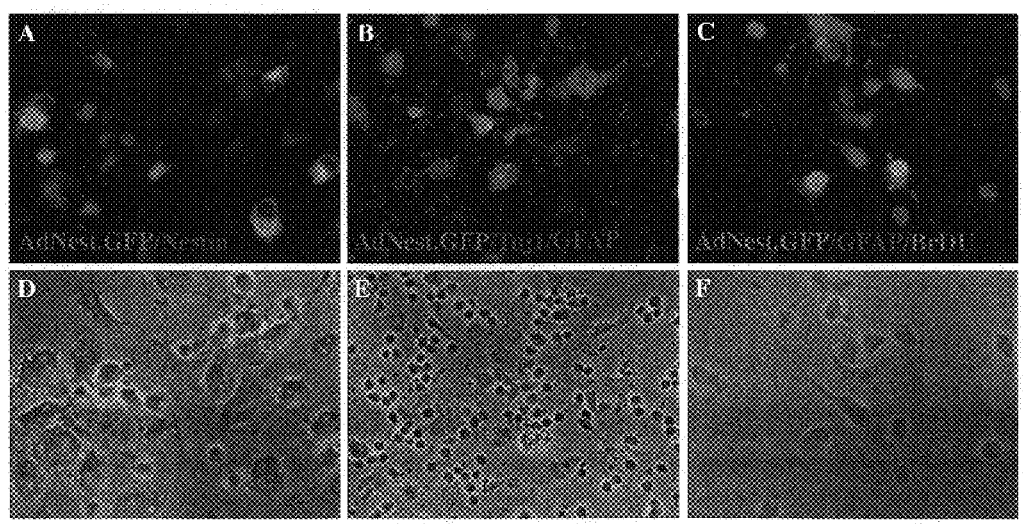
FIGS. 4A-F show AdE/Nest.EGFP+ cells which are mitotically competent and phenotypically uncommitted.
Figure 5:
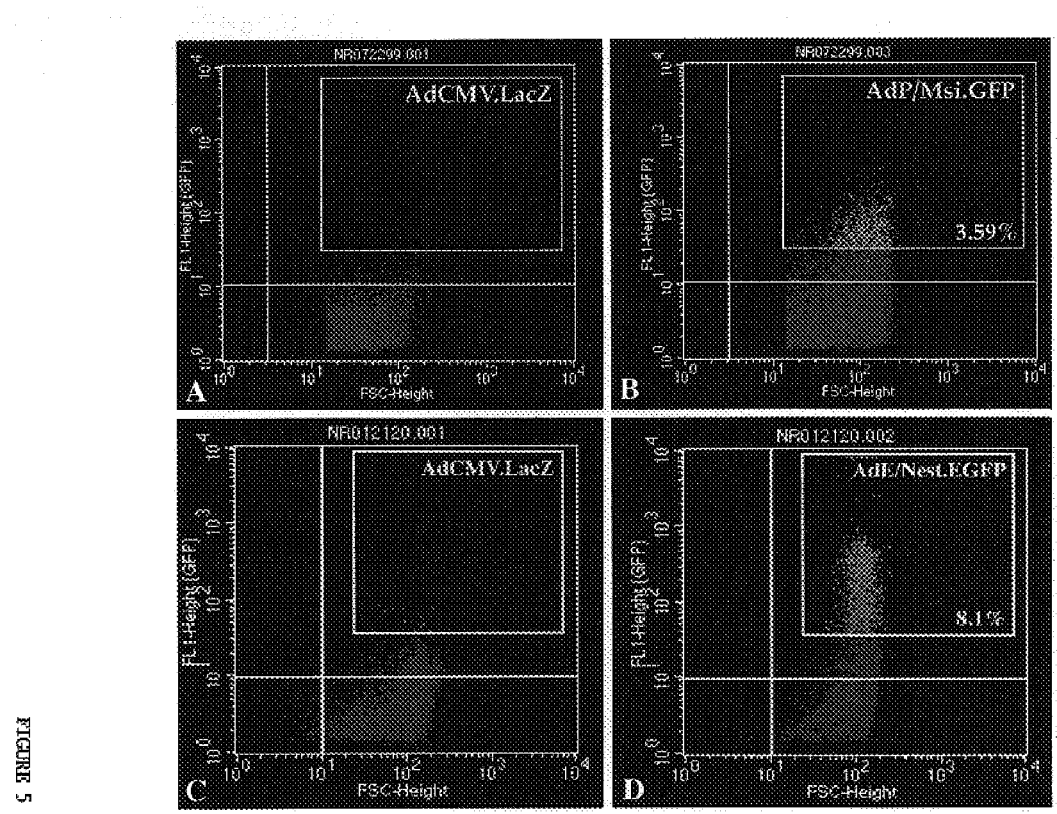
FIGS. 5A-D are graphs showing that AdP/Msi.hGFP+ and AdE/Nest.EGFP+ stem cells are enriched by FACS.

A plasmid designated pMsi:hGFP has been deposited pursuant to, and in satisfaction of, the requirements of the Budapest Treaty on the International Recognition of the Deposit of Microorganisms for the Purposes of Patent Procedure, with the American Type Culture Collection (ATCC), 10801 University Boulevard, Manassas, Va. 20110-2209 under ATCC Accession No. PTA-2852 on Dec. 26, 2000.

A plasmid designated pNestin:hsp68:EGFP has been deposited pursuant to, and in satisfaction of, the requirements of the Budapest Treaty on the International Recognition of the Deposit of Microorganisms for the Purposes of Patent Procedure, with the American Type Culture Collection (ATCC), 10801 University Boulevard, Manassas, Va. 20110-2209 under ATCC Accession No. PTA-2853 on Dec. 26, 2000.

As used herein, the term "isolated" when used in conjunction with a nucleic acid molecule refers to: 1) a nucleic acid molecule which has been separated from an organism in a substantially purified form (i.e. substantially free of other substances originating from that organism), or 2) a nucleic acid molecule having the same nucleotide sequence but not necessarily separated from the organism (i.e. synthesized or recombinantly produced nucleic acid molecules).

The subject invention provides a method of separating multipotential neural progenitor cells from a mixed population of cell types, based upon cell type-selective expression of cell specific promoters. This method includes selecting a promoter which functions selectively in the neural progenitor cells, introducing a nucleic acid molecule encoding a fluorescent protein under control of said promoter into all cell types of the mixed population of cell types, allowing only the neural progenitor cells, but not other cell types, within the mixed population to express said fluorescent protein, identifying cells of the mixed population of cell types that are fluorescent, which are restricted to the neural progenitor cells, and separating the fluorescent cells from the mixed population of cell types, wherein the separated cells are restricted to the neural progenitor cells.

The cells of particular interest according to the subject invention are multipotential neural progenitor cells. "Specific", as used herein to describe a promoter, means that the promoter functions only in the chosen cell type. A chosen cell type can refer to different stages in the developmental cycle of a cell.

The mixed population of cell types may be derived from, for example, a ventricular zone, a hippocampus, a spinal cord, bone marrow, e.g., bone marrow stroma or mesenchyma, or embryonic stem cells. The mixed population of cell types may be in tissue, e.g., brain tissue or spinal cord tissue, or in cell culture Illustrative promoters for multipotential neural progenitor cells include a musashi promoter and a nestin enhancer.

In accordance with one embodiment of the present invention, a human musashi promoter has a nucleotide sequence as shown in FIG. 11 (SEQ. ID. No. 1).

In accordance with another embodiment of the present invention, a human nestin enhancer has a nucleotide sequence as shown in FIG. 12 (SEQ. ID. No. 2).

Having determined the cell of interest and selected a promoter specific for the cell of interest, a nucleic acid molecule encoding a fluorescent protein, preferably a green fluorescent protein, under the control of the promoter is introduced into a plurality of cells to be sorted.

The isolated nucleic acid molecule encoding a green fluorescent protein can be deoxyribonucleic acid (DNA) or ribonucleic acid (RNA, including messenger RNA or mRNA), genomic or recombinant, biologically isolated or synthetic. The DNA molecule can be a cDNA molecule, which is a DNA copy of a messenger RNA (mRNA) encoding the GFP. In one embodiment, the GFP can be from *Aequorea victoria* (U.S. Pat. No. 5,491,084). A plasmid encoding the GFP of *Aequorea victoria* is available from the ATCC as Accession No. 75547. A mutated form of this GFP (a red-shifted mutant form) designated pRSGFP-C 1 is commercially available from Clontech Laboratories, Inc. (Palo Alto, Calif.).

Mutated forms of GFP that emit more strongly than the native protein, as well as forms of GFP amenable to stable translation in higher vertebrates, are now available and can be used for the same purpose. The plasmid designated pTα1-GFPh (ATCC Accession No. 98299) includes a humanized form of GFP. Indeed, any nucleic acid molecule encoding a fluorescent form of GFP can be used in accordance with the subject invention. Furthermore, any nucleic acid molecule encoding an enzyme that can catalyze the conversion of a fluorgenic substrate to a fluorophone can be used in accordance with the subject invention. An example is the use of a cell-specific promoter to drive lacZ expression, with the detection and sorting of lacZ-expressing cells being by means of incubation with the fluorgenic substrates FDG (fluorescein-β-D-galactopyranoside) or CMFDG (chloromethyl-FDG).

Standard techniques are then used to place the nucleic acid molecule encoding GFP under the control of the chosen cell specific promoter. Generally, this involves the use of restriction enzymes and ligation (see below).

The resulting construct, which comprises the nucleic acid molecule encoding the GFP under the control of the selected promoter (itself a nucleic acid molecule) (with other suitable regulatory elements if desired), is then introduced into a plurality of cells which are to be sorted. Techniques for introducing the nucleic acid molecules of the construct into the plurality of cells may involve the use of expression vectors which comprise the nucleic acid molecules. These expression vectors (such as plasmids and viruses) can then be used to introduce the nucleic acid molecules into the plurality of cells.

Various methods are known in the art for introducing nucleic acid molecules into host cells. These include: 1) microinjection, in which DNA is injected directly into the nucleus of cells through fine glass needles; 2) dextran incubation, in which DNA is incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. Some of the DNA evades destruction in the cytoplasm of the cell and escapes to the nucleus, where it can be transcribed into RNA like any other gene in the cell; 3) calcium phosphate coprecipitation, in which cells efficiently take in DNA in the form of a precipitate with calcium phosphate; 4) electroporation, in which cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures (passage through these vesicles may sometimes destroy or damage DNA); 5) liposomal mediated transformation, in which DNA is incorporated into artificial lipid vesicles, liposomes, which fuse with the cell membrane, delivering their contents directly into the cytoplasm; 6) biolistic transformation, in which DNA is absorbed to the surface of gold particles and fired into cells under high pressure using a ballistic device; and 7) viral-mediated transformation, in which nucleic acid molecules are introduced into cells using viral vectors. Since viral growth depends on the ability to get the viral genome into cells, viruses have devised efficient methods for doing so. These viruses include retroviruses and lentivirus, adenovirus, herpesvirus, and adeno-associated virus.

As indicated, some of these methods of transforming a cell require the use of an intermediate plasmid vector. U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture. The DNA sequences are cloned into the plasmid vector using standard cloning procedures known in the art, as described by Sambrook et al. (1989).

In accordance with one of the above-described methods, the nucleic acid molecule encoding the GFP is thus introduced into a plurality of cells. The promoter which controls expression of the GFP, however, only functions in the cell type of interest (i.e., multipotential neural progenitor cells). Therefore, the GFP is only expressed in the cell type of interest. Since GFP is a fluorescent protein, the cells of interest can therefore be identified from among the plurality of cells by the fluorescence of the GFP.

Any suitable means of detecting the fluorescent cells can be used. The cells may be identified using epifluorescence optics, and can be physically picked up and brought together by Laser Tweezers (Cell Robotics Inc., Albuquerque, N.

Mex.). They can be separated in bulk through fluorescence activated cell sorting, a method that effectively separates the fluorescent cells from the non-fluorescent cells (e.g., Wang et al., 1998).

The method of the subject invention thus provides for the isolation and enrichment of multipotential neural progenitor cells from embryonic and adult brain of both fetal and adult, rodent and human derivation. Specifically, fluorescence-activated cell sorting of adult human ventricular zone, adult hippocampus, and fetal human ventricular epithelium cells transfected with green fluorescent protein driven by the musashi promoter or the nestin enhancer is provided. In particular, tissue samples from fetuses of 14-23 weeks gestational age were obtained. Histological sections across several gestational ages were immunostained for musashi and nestin protein. Dissociates of ventricular zone were transduced with either a ΔE1 adenovirus bearing hGFP under the control of the musashi promoter (AdP/Musashi), or with an adenovirus encoding EGFP placed 3' to the heat shock protein-68 basal promoter under the regulatory control of the nestin second intronic enhancer (AdE/Nestin). Adenoviral vectors were used instead of plasmids for both P/Musashi.hGFP and E/Nestin.EGFP in order to increase transfection efficiency. The phenotypic specificity of each selection construct, E/Nestin.EGFP and P/Musashi.hGFP, was verified in the adenoviruses as well as in the plasmids. Following GFP expression, the GFP$^+$ cells were extracted by FACS. The resulting native prospectively-identified and directly-harvested, non-transformed multipotential neural progenitor cells are self-renewing, generate neurons, astrocytes, and oligodendrocytes, both in vitro and upon transplantation to recipient brains. Unlike other putative neural stem lines, these have been extracted directly from the human fetal ventricular epithelium, without the need for either initial epidermal growth factor-expansion or oncogenic immortalization; each of which can perturb the phenotypic stability and functional competence of neuronal and glial progeny so derived.

The cells separated by the method of the present invention may be used in both basic analyses of precursor and stem cell growth control, as well as in directly applied studies of their transplantability and engraftment characteristics. The cells similarly can be used in support of the structural repair of the damaged central nervous system, such as in the traumatized brain, or the contoured, traumatized, or transected spinal cord.

EXAMPLES

Example 1

Materials and Methods

Human Fetal Culture

Human fetal brain was taken at second trimester therapeutic abortion, typically performed for either placenta previa, premature rupture, sonographically-demonstrated isolated splanchnic or cardiac developmental abnormalities, or karyotypically-identified trisomies 18 or 21. These brains were collected into Ca/Mg-free Hanks' Balanced Salt Solution (HBSS), then dissected to separate first the telencephalon from the brainstem, and then the telencephalic ventricular epithelium from non-ventricular parenchyma. The telencephalic ventricular zone was then cut into small pieces in PIPES solution (120 mM NaCl, 5 mM KCl, 25 mM glucose, 20 mM PIPES), then digested with papain (11.4 units/ml papain, Worthington Biochemical Corporation) and DNase I (10 units/ml, Sigma, St. Louis, Mich.) in PIPES solution, with gentle shaking for 1 hour at 37° C. in 5% $CO_2$. Following incubation, the tissue was collected by centrifuging at 200 g for 5 minutes in an IEC Centra-4B centrifuge, resuspended in DMEM/F12/N2 with DNase I (10 units/ml) and incubated for 15 minutes at 37° C/5% $CO_2$. The samples were spun and the pellets resuspended in 2 ml of DMEM/F12/N2, then dissociated by sequentially triturating for 20, 10, and 5 times, through three serially-narrowed glass Pasteur pipettes. The dissociated cells were purified by passing through a 40 μm Cell Strainer (Becton Dickinson), rinsed with DMEM/F12/N2 containing 20% fetal bovine serum FBS, Cocalico), and resuspended at $4\times10^6$ cells/ml in DMEM/F12/N2 containing 5% FBS. The cells were plated at 0.5 ml/dish into 35 mm Falcon Primaria plates, precoated with murine laminin (2 μg/cm$^2$, Gibco) and incubated at 37° C. in 5% $CO_2$. After 1 day, an additional 0.5 ml of DMEM/F12/N2 with 2% platelet-depleted FBS (PD-FBS) was added to each plate. For some cultures, 30 μM bromodeoxyuridine (BrdU; Luskin et al., 1997) was added to the medium in order to label dividing cells.

Construction of E/nestin:EGFP and AdE/nestin:EGFP

To identify neural progenitor cells, a green fluorescent protein expression vector was constructed, with EGFP placed under the control of the nestin enhancer (Zimmerman et al., 1994; GeneBank Accession No. AF004334). The latter, a 637 bp-region between bases 1162 and 1798 of rat nestin gene, is evolutionarily conserved between human and rat, and is sufficient to target gene expression to CNS neuroepithelial progenitor cells (Lothian, 1997). The nestin enhancer was placed upstream of the minimum promoter of heat shock protein 68 (hsp68) (Rossant, 1991), yielding E/nestin:hsp68 (Lothian, 1997). This was in turn fused to EGFP polyA (Clontech, Palo Alto, Calif.), yielding E/nestin:EGFP, as previously described (Roy et al., 2000a). The neuroepithelial cell-specific expression of this transgene was confirmed by transgenic mouse studies.

Construction of P/musashi:hGFP and AdP/musashi:GFP

An adenoviral vector bearing the mouse musashi promoter to drive hGFP was constructed. The shuttle vector pAdCMV-H( )SgD (Courtesy of Dr. Neil Hackett/Gene Therapy Core Facility of Weill Medical College) was digested with Not I blunt and XhoI to remove the existing immediate-early cytomegalovirus (CMVie) promoter. The expression cassette CMVie-SD/SA-hGFP-polyA was then removed from pCMV-hGFP using BstXI/blunt and SalI. The resulting expression cassette was ligated to the shuttle vector. This was referred to as pAdCMV-hGFP, in which CMVie was flanked by XbaI. pAdCMV-hGFP was digested with XbaI, dephosphorylated, and ligated to the 4.5 Kb XbaI-XbaI fragment corresponding to the mouse musashi promoter. The orientation of the promoter was determined by SacII, which cuts both once at the 3' end of the promoter and within hGFP. Established methods were then used to construct a replication-defective recombinant adenovirus, via homologous recombination using the plasmid pJM17, which contains the E1A-deleted type 5 adenovirus. pAdMsi-hGFP was co-transfected with pJM17 into HEK293 cells, and viral plaques developed for 2 weeks. The virus was purified using double centrifugation in CsCl. The titer of the purified virus was between $10^{11}$-$10^{12}$ pfu/ml.

Transfection

Two E/nestin-bearing plasmids, that included pE/nestin:EGFP and pE/nestin:lacZ, were used. A cationic liposome, Effectene (Qiagen, Germany), was used to transfect these plasmids into cultured adult VZ/SVZ cells, as follows. After the first day in vitro, 1 ml of DMEM/F12/N2 with 5% FBS was added to each culture. A total of 0.4 µg of plasmid DNA was diluted with 100 µl of Effectene DNA-condensation buffer, and mixed with 3.2 µl of Enhancer, following the manufacturer's instructions. The liposome:DNA complex was then incubated at room temperature for 5 minutes. 10 µl of Effectene was then added to the DNA/Enhancer solution, and the mixture incubated at 25° C. for 10 minutes. 0.6 ml of DMEM/F12/N2 with 5% FBS was added to this solution, which was then mixed and applied to the culture. After a 6 hour transfection, the cells were collected and spun. The resultant pellet was resuspended into DMEM/F12/N2 with 5% FBS, and plated onto a laminin-coated 35 mm Primaria plate. GFP was typically expressed by appropriate target cells within 2 days of transfection.

Flow Cytometry and Sorting

Flow cytometry and sorting of hGFP$^+$ cells was performed on a FACS Vantage (Becton-Dickinson). Cells were washed twice with Ca$^{++}$, Mg$^{++}$-free HBSS, then dissociated by 0.05% trypsin-EDTA for 5 minutes at 37° C. The dissociation reaction was terminated by DMEM/F12/N2 containing 10% FBS. The cells (2×10$^6$/ml) were analyzed by light forward and right-angle (side) scatter, and for GFP fluorescence through a 510±20 nm bandpass filter, as they traversed the beam of a Coherent INNOVA Enterprise II Ion Laser (488 nm, 100 mW). Sorting was done using a purification-mode algorithm. The E/nestin:lacZ transfected cells were used as a control to set the background fluorescence; a false positive rate of 0.1-0.3% was accepted so as to ensure an adequate yield. For those samples transfected with E/nestin:EGFP, cells detected as being more fluorescent than background were sorted at 1000-3000 cells/second. Sorted GFP$^+$ cells were plated on laminin-coated 24-well plates, in DMEM/F12/N2 with 5% FBS and BrdU. At 2 and 7 days post-FACS, the sorted cultures were fixed and immunostained for BrdU together with either TuJ1/βIII tubulin, Hu, MAP2, O4, or GFA.

Transuterine Fetal Xenograft

Transuterine injection for chimeric brain construction has been previously described (Brustle et al., 1998). Six pregnant females were anesthetized with ketamine and xylazine, and the peritoneum incised and the amnion exposed and displayed. The individual rat fetuses were trans-illuminated by a cool fiber-optic, and the cerebral ventricles outlined visually. A 30 g needle was then inserted through the amnion and calvarium directly into the ventricle, and 5×10$^4$ cells/µl were injected, as a 1 µl injection. After all embryos were injected, their amniotic sacs were replaced, and the peritoneum and skin closed as 2 layers with 2-0 and 3-0 silk, respectively. The females awoke to ad-lib food and water, and were allowed to deliver their litters normally, 4-5 days later. The pups were fed ad-lib by their mothers, and were sacrificed by pentobarbital overdose on either day 17 or day 35 after birth. They were perfusion-fixed by cold PBS followed by 4% paraformaldehyde, and their brains subsequently cut on a Hacker cryostat, as serial 12 µm sections in the coronal plane.

Immunostaining and Imaging

In vitro

After 2, 7, or 14 DIV, the cultures were fixed for immunocytochemistry. They were first rinsed with HBSS, then fixed with 4% paraformaldehyde for 5 minutes at room temperature. The plates were stained for either βIII tubulin (MAb TuJ1, 1:500; courtesy of Dr. A. Frankfurter), Hu protein (Mab 16A11, 50 µg/ml; Dr. H. Furneaux), or nestin (MAb Rat-401, 1:500; Developmental Studies Hybridoma Bank); all are markers of neural (nestin) or neuronal (βIII tubulin and Hu protein) antigenic expression (Frederiksen, 1988; Menezes, 1994; Barami, 1995). Additional plates were stained for glial markers, with either anti-oligodendrocytic O4 IgM (1:100; Boehringer Mannheim) for oligodendrocytes, or anti-astrocytic glial fibrillary acidic protein (GFAP, clone GA-5, 1:100; Sigma, St. Louis, Mich.), using previously established protocols (Kirschenbaum, 1994). Additional plates were fixed after 14 DIV and stained for MAP-2 protein to detect more mature neurons (1:500, rabbit anti-MAP2; Dr. S. Halpain). Immunocytochemistry for BrdU was then performed as described (Wang, 1998).

In vivo

Rat pups that had been injected with cells on either day E17 or P1 were sacrificed, perfusion fixed, and their brains removed on either the 14$^{th}$ or 21$^{st}$ day after birth. Fixation was accomplished using 4% paraformaldehyde in 0.1M phosphate buffer (PB; pH 7.4), with a 90 minute post-fix followed by immersion and sinking in 30% sucrose in PB. All brains were cut as 15 µm coronal sections. Some were then denatured in 2N HCl for an hour, and stained for BrdU, using rat anti-BrdU antibody at 1:200 (Harlan), followed serially by fluorescein-conjugated anti-rat IgG at 1:150 (Jackson Labs). Other sections were stained with an anti-human nucleoprotein antibody (Chemicon; 1:100; Vescovi et al., 1999). Other sections were instead subjected to in situ hybridization for human Alu DNA, using a digoxigenin-labeled Alu probe, which was then detected using biotinylated anti-digoxigenin IgG and fluorescein-conjugated avidin, as described.

The sections were then washed and stained for either neuronal or glial markers. Neuronal markers included βIII-tubulin, detected by monoclonal antibody TuJ1 (Menezes and Luskin, 1994; Roy et al., 2000) (a gift of Dr. A. Frankfurter); NeuN (Eriksson et al., 1998) (Chemicon); or Hu (Marusich et al., 1994; Barami et al., 1995), each as described. Glia were localized using antibodies directed against either oligodendrocytic CNP protein (Roy et al., 1999), or astrocytic GFAP. All anti-mouse secondary antibodies were pre-absorbed against rat IgG to avoid nonspecific staining.

Confocal Imaging

In sections double-stained for either BrdU or anti-human nucleoprotein together with either βIII-tubulin, NeuN, GFAP, or CNP, single BrdU$^+$ cells that appeared to be co-labeled for both human- and cell-specific markers were further evaluated by confocal imaging. Using a Zeiss LSM510 confocal microscope, images were acquired in both red and green emission channels using an argon-krypton laser. The images were then viewed as stacked z-dimension images, both as series of single 0.9 µm optical sections, and as merged images thereof. The z-dimension reconstructions were all observed in profile, as every BrdU$^+$ or ANA$^+$ human cell double-labeled with a neuronal or glial marker was then observed orthogonally in both the vertical and horizontal planes. To be deemed double-labeled, cells were required to have central BrdU or ANA immunoreactivity surrounded by neuronal or glial immunoreactivity at all observation angles, in every optical section, and in each merged composite.

Retroviral Preparation and EGFP Tagging

The NIT retrovirus (courtesy of T. Palmer and F. Gage) was prepared as previously described (Sakurada et al., 1999). Briefly, HEK 293gag/pol cells were stably transduced to express NIT.EGFP retrovirus, a derivative of the LINX retrovirus (Hoshimaru et al., 1996). These cells were then transfected with pMD.G, encoding vesicular stomatitis virus coat protein (VSV-G), so as to allow high-efficiency amphotropic infection of human cells. Viral supernatants were harvested 2 days later and aliquots stored at 80° C. until the time of use. Sorted cells subjected to retroviral infection were exposed to viral supernatant for a total of 12 hours in the presence of polybrene (8 μg/ml), beginning the morning after FACS. Three increments of 250 μl of viral supernatant were successively added 4 hours apart to an initial sample of 10,000 sorted cells in 250 μl medium. After a total of 12 hours in viral supernatant, the cells in each well were washed in fresh media and respun and redistributed to fresh 24-well plates at 10,000 cells/300 μl/well. This protocol of repetitive viral exposure was used to maximize the yield of virally-transduced neural progenitors available to clonal analysis.

Propagation and Genetic Tagging of Human Neural Stem Cells

AdE/nestin:EGFP$^+$ and AdP/msi:hGFP$^+$ cells were each extracted as noted by FACS. At that point, the GFP$^+$ cells were distributed into 24-well plates at 10,000/well, and raised in serum-free media supplemented with 20 ng/ml FGF2. The following day, the cells were infected with the NIT.EGFP retrovirus (see above), by which means the sorted cells were stably transduced to express EGFP. After 4 weeks, adenoviral-associated GFP expression fell to undetectable levels, in that sorted cultures not exposed to retroviral NIT.EGFP lost all nestin and musashi-driven GFP expression. Some sorted cultures were then re-sorted on the basis of GFP expression, resulting in the specific extraction of retroviral GFP-tagged neural stem cells. Other plates were supplemented with neomycin, which selected for the retrovirally-transduced lines by virtue of a selectable neo resistance gene in the retroviral construct. Each strategy yielded uniform cultures of GFP$^+$ cells at 6 weeks in vitro. Spheres were noted in these cultures, often as early as 2 weeks in vitro, and at 6 weeks these sphere were transferred to new wells within 24-well plates, at 2-3 spheres/well. These spheres were in turn raised for another 2 weeks, then dissociated by mild trypsinization and passaged into new wells. These cells were maintained for another 2 weeks, by which point secondary spheres were observed to arise from many of the single cells derived from the initially-dissociated primary sphere. This procedure of mitotic sphere expansion in FGF2-containing suspension culture, followed by gentle dissociation of the spheres, passage of the dissociated cells, and replating with sphere regeneration and re-expansion, was repeated at monthly intervals thereafter. Aliquots of neural stem cells are removed at roughly biweeekly intervals, both for experimental transplantation, and for phenotypic analyses of their differentiated progeny. Stable GFP-tagged AdE/nestin and AdP/musashi-defined neural stem cells have been thereby continuously propagated for over 8 months; separate lines have been established from both forebrain and spinal cord, and from each at several different gestational ages spanning the second trimester.

Example 2

Musashi and Nestin Protein Expression Characterize Distinct but Overlapping Domains within the Fetal Human Ventricular Zone Immunostaining for nestin and musashi proteins at several stages in mid-gestation revealed that these early neural proteins occupied distinct but overlapping domains within the fetal human telencephalic wall. At gestational ages spanning from 12-21 weeks of second trimester development, musashi protein was expressed ubiquitously within the densely packed ventricular neuroepithelium, with diminished expression within the nascent subventricular zone, and virtually none within the intermediate zone and cortical parenchyma (FIG. 2A-E). Nestin expression was similarly noted within the ventricular zone, and many double-labeled cells were noted therein. However, the density of nestin$^+$ cells within the VZ was notably lower than that of musashi$^+$ cells, and many musashi$^+$ VZ cells did not express detectable nestin. In contrast, within the subventricular zone, many nestin$^+$ cells were noted to not express musashi. Within the intermediate zone, a dense array of nestin$^+$ radial guide cells was noted, which did not express musashi, but upon which both musashi and nestin$^+$ migrants were frequently noted.

Using high-magnification confocal microscopy of double-immunostained 14 week rostrolateral telencephalic ventricular zone, it was noted that 72% of VZ cells expressing musashi protein co-expressed nestin protein. In contrast, at 21 weeks, 93% of the musashi expressing cells co-expressed nestin. Thus, the incidence of musashi$^+$/nestin-cells within the rostrolateral telencephalic VZ decreased from 27% to 5% between the 14th and 21st weeks of gestational development. IR cells.

Thus, a substantial degree of overlap was observed among musashi and nestin-immunoreactive cells, in that a large proportion of VZ cells expressed both proteins. Interestingly though, the observations also indicate the existence of a musashi$^+$/nestin- phenotype within the ventricular neuroepithelium. By virtue of its relative prevalence at the adluminal surface of the ventricular neuroepithelium, this musashi$^+$/nestin-phenotype may constitute an ontogenetically earlier cell population than that defined by nestin (FIG. 2A-E).

Example 3

The Nestin Enhancer Targeted GFP Expression to Neural Progenitor Cells In Vitro

In order to label live neural progenitor cells in which nestin and musashi regulatory elements were transcriptionally active, cells derived from fetal VZ samples spanning 14-23 weeks of gestational age were infected with adenoviruses bearing EGFP under the regulatory control of either the nestin enhancer (E/nestin:EGFP) or musashi promoter (P/musashi:hGFP) (FIG. 9A-D). To this end, papain dissociates of the dissected ventricular walls were obtained from 25 fetuses; these included 9 of 14-19 weeks gestational age, and 16 of 20-23 weeks gestation. These dissociates were then prepared as suspension cultures in DMEM/F12/N2, supplemented with 20 ng/ml FGF2; some were also supplemented with 2% PD-FBS.

To both improve the efficiency with which the E/nestin:EGFP selection cassette could be introduced into these ventricular zone cells, and to increase the transgene copy number in transfectants, an adenovirus bearing E/nestin:EGFP was constructed. Using this AdE/nestin:EGFP virus, human fetal VZ suspension cultures were infected on their first day in vitro, over a range of 1-25 moi. Within 4 days of infection, nestin-driven GFP expression was noted in a relatively primitive population of flat cells. Among these E/nestin:EGFP$^+$ cells, 98.9±1.2% expressed nestin protein. 61.6±7.6% incorporated BrdU, indicating their mitogenesis in vitro. Yet only 3.1±0.6% expressed βIII-tubulin-immunoreactivity, and 8.9±1.6% expressed astrocytic GFAP (FIG. 3A-F). Thus, the nestin enhancer directed GFP expression to a relatively undifferentiated population of mitotically-active cells in mixed dissociates of the fetal human VZ.

Example 4

The Musashi Promoter Targets GFP Expression to an Overlapping Population of Neural Progenitor Cells Given musashi's robust and relatively selective expression by uncommitted progenitor cells in both the rodent (Sakakibara et al., 1997) and human VZ (Pincus et al., 1998), it was reasoned that a GFP transgene placed under musashi promoter control might, like nestin enhancer-driven GFP, specifically recognize neural progenitor cells. To that end, the 4.6 kb promoter for human musashi promoter was coupled to hGFP, thereby establishing the P/musashi:hGFP selection cassette. A type 5 ΔE1 adenovirus was then constructed bearing P/musashi:hGFP selection cassette, which was designated AdP/msi:hGFP. Using this vector, it was found that the transduction efficiency in cultures of human VZ cells rose substantially, relative to cultures transfected with P/musashi: GFP plasmid DNA (data not shown), with no evident effect on cell viability in the 10-25 pfu/cell range at which this virus was used. No βIII-tubulin+ neurons were noted among the AdP/musashi:GFP-sorted cells, whereas 96.1±2.0% expressed nestin protein (FIG. 4A-F). 93.3±3.4% of AdP/ musashi:GFP+ cells incorporated BrdU, indicating their persistent division in vitro.

Thus, both the AdE/nestin:EGFP and AdP/musashi:hGFP viruses retained the phenotypic expression patterns of their incorporated promoter-driven GFPs; both were expressed by uncommitted progenitor cells, but not by more differentiated neurons. Together, these data suggest that adenoviruses bearing GFP under the regulatory control of the nestin enhancer and musashi promoter may be used to specifically and selectively identify neural progenitor cells, before neuronal commitment.

Example 5

FACS Based on Nestin and Musashi-Driven GFP Permits the Isolation and Selection of Human Neural Progenitor Cells After infection of the fetal VZ/SVZ with AdE/nestin:EGFP and AdP/musashi:hGFP, the neural precursors and their daughters were isolated and extracted by FACS (FIG. 1). By high-stringency FACS criteria, intended for cell-type purification, (Wang, 1998), it was found that 10.6±2.6% of cells (mean±SE; n=3 sorts) prepared from 17-19 week gestational age ventricular zone expressed nestin-driven GFP. A small but statistically significant fall to 7.4±1.5% (n=11 sorts) was noted in the proportion of AdE/nestin:EGFP+ cells in dissociates derived from 20-23 week VZ ($p<0.05$ by 1-way ANOVA with post hoc Boneferroni t-test). Using the same sort acceptance criteria, only 0.05% of cells infected with non-fluorescent AdCMV:lacZ. were similarly recognized.

The frequency of AdP/musashi:hGFP-defined VZ cells was consistently lower than that of E/nestin-defined cells, at both 17-19 weeks (2.4±0.6%; n=6 sorts) and 20-23 weeks. (3.2±0.4%; n=11). Using forward and side-scatter endpoints, the AdE/nestin- and AdP/musashi-defined progenitors appeared to constitute largely overlapping pools (FIG. 5A-D).

Figure 6:
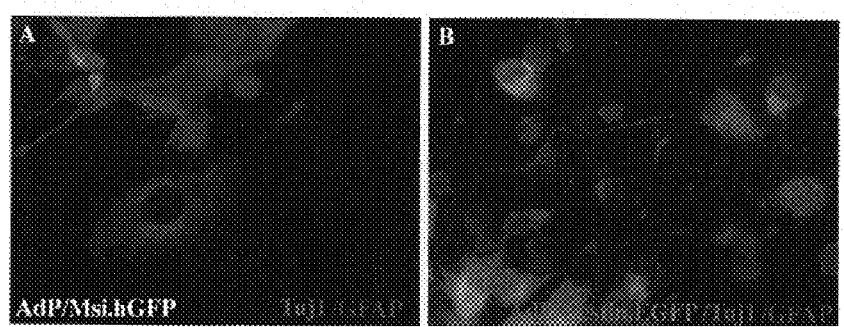
FIGS. 6A-B show early post-sort characterization of AdP/Msi.hGFP+ and AdE/Nest.EGFP+ cells. Purified AdP/Msi.hGFP+ and AdE/Nest.EGFP+ cells each generated neurons and astrocytes when plated on fibronectin with medium containing 2% fetal bovine serum.
Figure 7:
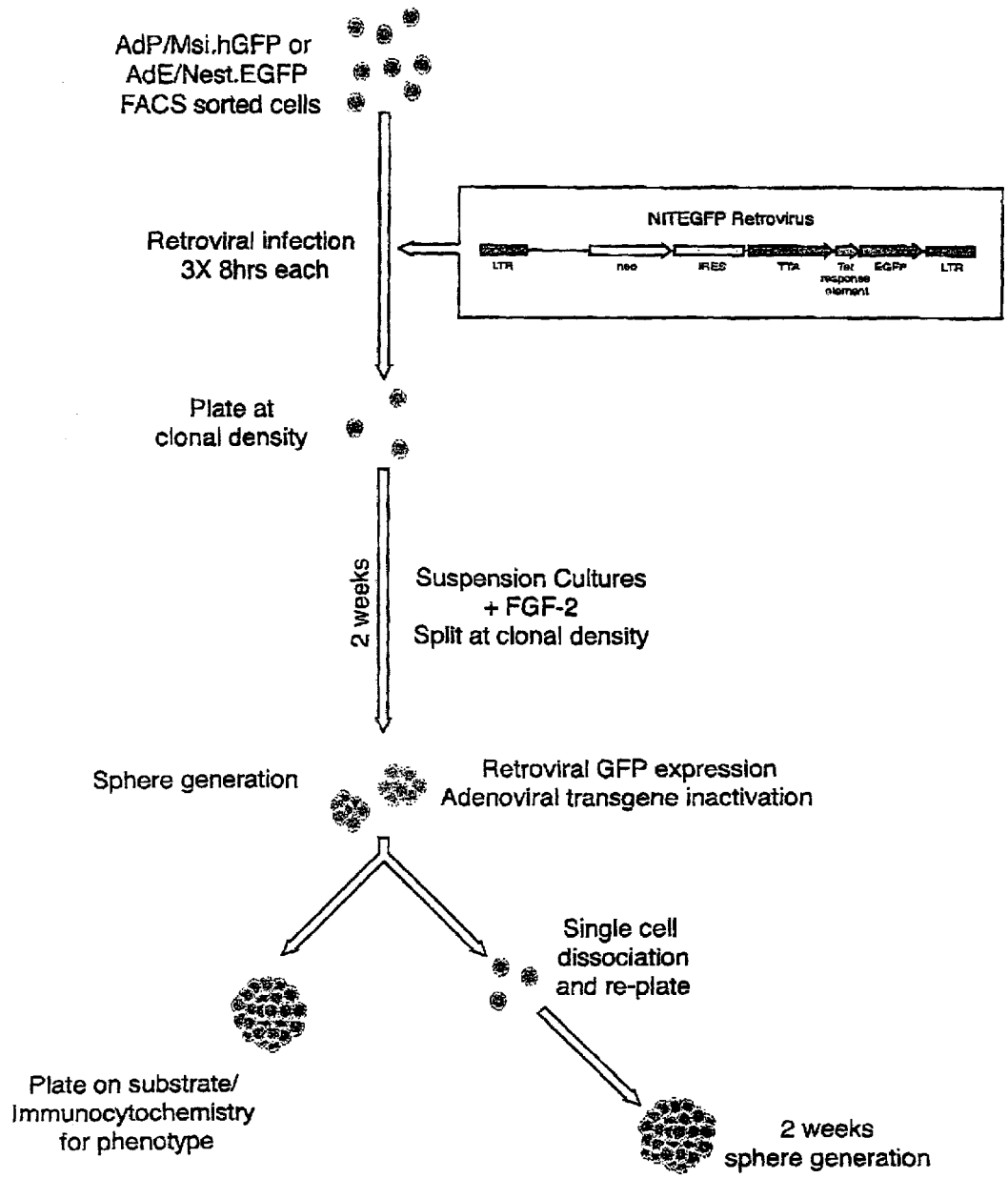
FIG. 7 is a schematic showing a strategy for propagation and genetic tagging of human neural stem cells.
Figure 8:
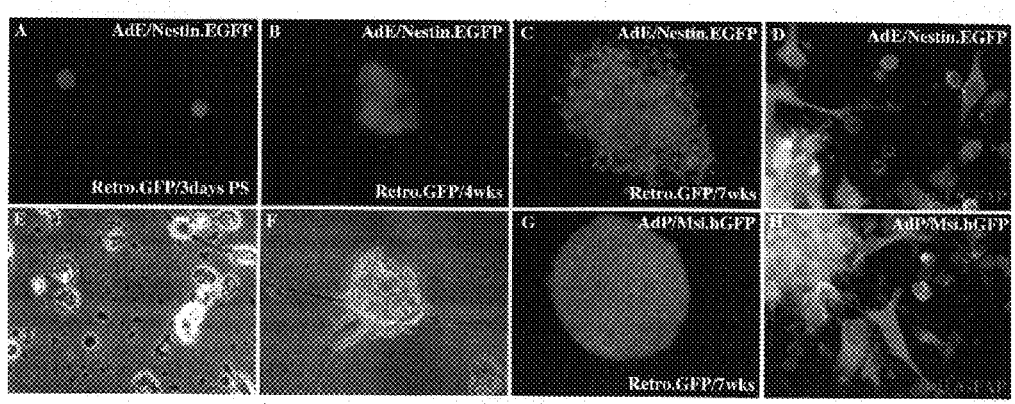
FIGS. 8A-H show AdE/Nest.EGFP and AdP/Musashi.hGFP-sorted cells tagged with retroviral EGFP generated clonally-derived secondary spheres, that in turn give rise to neurons and glia.
Figure 9:
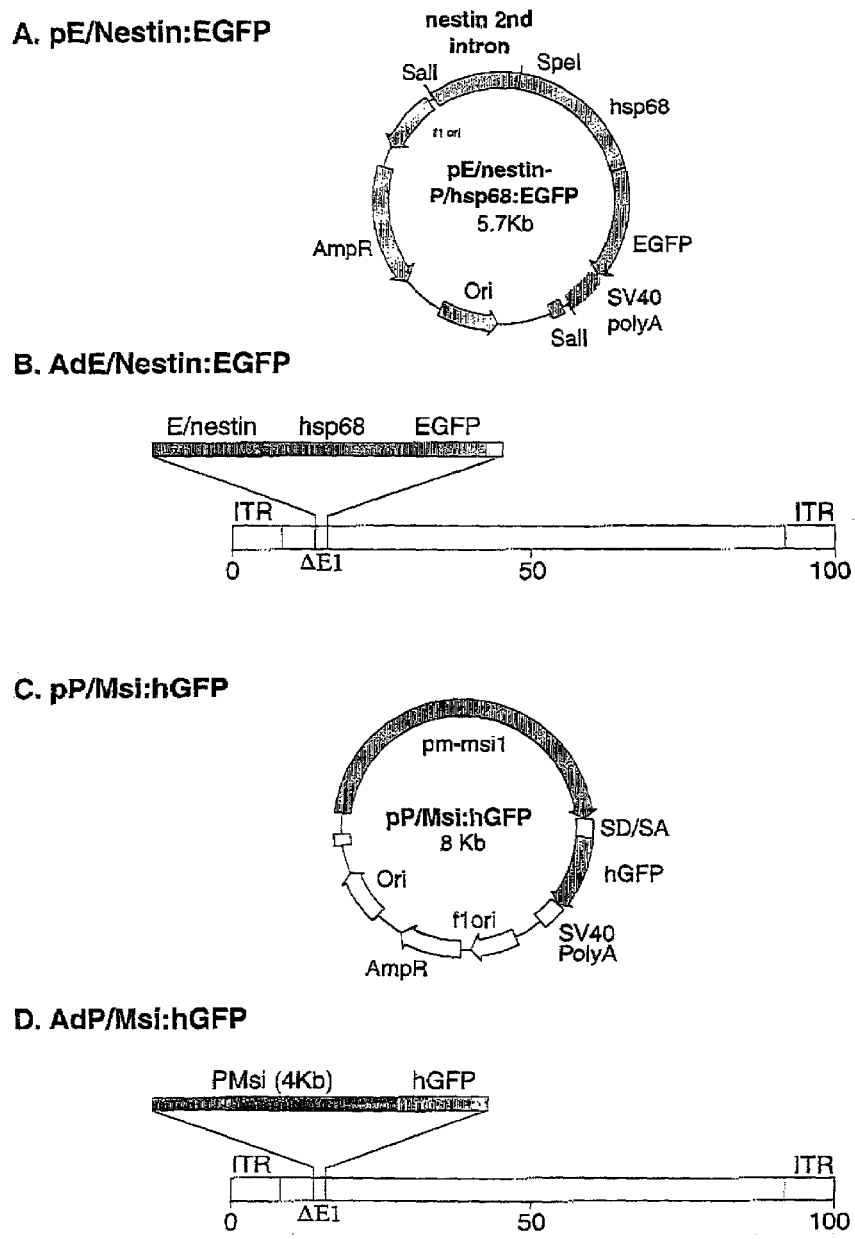
FIGS. 9A-D are schematics showing AdE/nestin:EGFP and AdP/musashi vectors.

Virtually all of the E/nestin:EGFP-sorted cells expressed nestin protein immediately after FACS; 83.7±7.7% (n=3 sorts) did so after 1 week in serum-free media. Cells expressing the early neuronal proteins Hu and TuJ1/βIII-tubulin were rarely detected in these cultures, even at a week after E/nestin: EGFP-based FACS. Interestingly though, only 36.3±8.2% (n=3) expressed nestin protein in 2% PD-FBS, suggesting the rapid differentiation of E/nestin:EGFP+ cells upon exposure to serum-associated maturation factors. Accordingly, a majority of the sorted progenitors raised in PD-FBS matured as βIII-tubulin+ neurons and GFAP+ glia within the week after FACS (FIG. 6A-B).

Example 6

E/nestin:EGFP- and P/musashi-Identified Cells Were Both Mitotically Competent and Multipotential To establish the in vitro lineage potential of these cells, both population-based and single cell clonogenic strategies were employed, both independently and in parallel with concurrent retroviral lineage analysis. First, low density cultures of purified E/nestin:EGFP and P/musashi:hGFP-sorted cells were prepared to allow the emergence of neurospheres. This was followed by the dissociation of these spheres and the limiting dilution propagation of their progeny as secondary spheres, whose clonally-related constituents were then phenotyped after plating and immunolabeling. In addition, retroviral tagging of single E/nestin- and P/musashi-sorted cells in primary spheres, followed by the re-dissociation and dispersion of these tagged cells with clonal expansion as secondary spheres, allowed the antigenic phenotypes of clonally-related daughters to be established. This approach revealed that individual secondary and tertiary spheres, each clonally-derived from single, E/nestin- and P/musashi-sorted cells tagged with retroviral GFP, indeed gave rise to both neuronal and glial daughters (FIGS. 7 and 8A-H). Thus, both E/nestin:EGFP and P/musashi:hGFP-sorted cells continued to divide in vitro, and each phenotype gave rise individually to both neurons and glia.

Example 7

Both E/nestin:GFP and P/musashi:GFP-Sorted Progenitors Generated Neurospheres

Limiting dilution analysis of both AdP/Msi:hGFP and E/nestin:EGFP-sorted cells was also performed, with propagation of sorted GFP+ cells in suspension culture. These sorted cells were initially raised in a serum-free base medium of DMEM/F12/N2 with 10 ng/ml FGF2, according to established protocols for neurosphere suspension culture (Gritti, 1996, Vescovi, 1999). This was followed two weeks later by preparation of secondary spheres, raised under conditions appropriate for clonal expansion. Single aggregates were removed to single wells in a 24-well plate, then gently dissociated, and their E/nestin:EGFP+ progeny were then plated at low density (1000 cells/ml) into 24 well plates, at 300 μl/well. In addition, some cells were distributed at 10/ml into 35 mm plates containing base media supplemented with 1.4% methylcellulose. This more viscous preparation, in tandem with the very low plating density, permitted the clonal expansion of single cells while diminishing the possibility of aggregation among potentially non-clonally-derived neighbors. In each case, initial dispersion of single cells within the media was verified by high-power phase microscopy of each plate, and undissociated aggregates were removed by micropipette. The positions of expanding clusters were marked, and these were followed daily thereafter, to ensure the autologous expansion and co-derivation of single clusters.

In forebrain ventricular zone samples derived from 4 fetuses of 20-22 weeks gestation, an average of 13.4±1.0 spheres/well for AdP/msi:hGFP-sorted cells was observed, and 11.5±1.2 spheres/well for AdE/nestin:EGFP-sorted cells (FIG. 8A-H). The relative proportion of sphere-generating cells within each well was dependent upon both gestational age and plating density, in that both earlier ages and higher plating densities yielded disproportionately higher proportions of sphere-generating clones (data not shown). Thus, this approach may not be used as a basis for estimating the incidence of stem cells in either the E/nestin or P/musashi-sorted cell populations. Indeed, initial cell depositions at 1,000 sorted cells/well were maintained in order to titrate to roughly 10 clones/well, both for ease of handling and to ensure the clonal derivation of cells obtained from subsequent single-sphere dissociations. Given the predominance of nestin and musashi-expressing cells in the early ventricular neuroepithelium, their frequent multipotentiality and their high mitotic indices, the relative scarcity of sphere-generating cells within the P/musashi- and E/nestin-sorted pools argue that clonogenic stem cells may represent only a minority of the cycling, multipotential neural progenitor cells within the sorted samples.

Example 8

Retroviral Lineage Analysis Confirmed the Multipotentiality of Both E/nestin:GFP and P/musashi:GFP-Sorted Progenitor Cells Retroviral lineage analysis confirmed that individual E/nestin- and P/musashi-sorted cells each gave rise to both neuronal and glial lineages. Both populations of sorted cells were infected immediately after FACS with a VSV-pseudotyped amphotropic vector encoding EGFP under the control of the constitutive RSV promoter. Over the weeks after FACS, E/nestin- and P/musashi-sorted cells typically lost GFP expression, as their progeny diversified and both nestin and musashi transcription diminished, and as the episomal transgenes were down-regulated or abandoned. In contrast, the retrovirally-tagged cells and their progeny maintained high level GFP expression; within a week after E/nestin:EGFP-based sorting, the retrovirally-tagged cells could be readily distinguished from the untagged remainder. By infecting E/nestin:GFP-sorted cells at a relatively low density of 10-20 infectants/well, it was possible to follow the clonal progeny of single cells over the weeks after FACS.

After expansion of the retrovirally-tagged clonal progeny, individual spheres were dissociated and their constituents removed to a laminin substrate, to which base media supplemented with 10% PD-FBS and 20 ng/ml BDNF was added. Under these differentiation-promoting conditions, the cells were allowed to adhere and mature for an additional 1-2 weeks. They were then fixed with 4% paraformaldehyde, and immunostained either for neuronal (TuJ1), astrocytic (GFAP), or oligodendrocytic (O4) antigens. Using this strategy, it was found that individual E/nestin- and P/musashi-sorted cells were each competent to give rise to both neurons and glia.

Example 9

Both E/nestin:GFP and P/musashi:GFP-Sorted Progenitors Could Generate All Neural Phenotypes Upon Xenograft to Fetal and Perinatal Rat Brain To assess the responsiveness of E/nestin:EGFP-defined cells to differentiation cues in a parenchymal environment, fetal VZ cells were xenografted into E17 rat forebrain ventricles, using an adaptation of a previously reported technique (Brustle et al., 1998). Briefly, E17 pregnant female rats were anesthetized and laparotomized, and the uterus trans-illuminated to allow direct visualization through the placental sac of each fetuses' forebrain and ventricular lumen. An average of $1 \times 10^5$ E/nestin:EGFP-FACSed fetal human VZ cells were injected into the lateral ventricular lumen of each embryo, and the mother sutured and allowed to deliver 4-5 days later. Three weeks later, the pups were sacrificed, and their brains fixed and cut as 12 µm cryostat sections, that were then immunolabeled for anti-human nuclear antigen to identify the grafted human fetal cells, together with neuronal βIII-tubulin and either oligodendrocytic cyclic nucleotide phosphodiesterase (CNP), or astrocytic GFAP.

It was found that human-derived cells were abundant in the grafted pups, and readily identified as such. Indeed, when xenografted to the fetal rat forebrain, most of the human E/nestin:EGFP$^+$ cells integrated as neurons, resulting in the formation of chimeric human-rat neocortices. Upon xenograft at E17—a period characterized by predominantly cortical neurogenesis by the ventricular neuroepithelium—most human cells were noted to have migrated to the cortical laminae, and to have differentiated as neurons rather than glia (FIG. 10A-F).

In contrast, when xenografted as intraventricular injections to P1 neonatal hosts, most human cells were noted to enter only the subcortex, wherein most differentiated as glia. Within the subcortical white matter, when assessed at 28 days of age, both human oligodendrocytes and astrocytes, as defined by GFAP, were noted to be abundantly represented (FIG. 10A-F), whereas human neurons were rarely noted, and then only in the rostral telencephalon, migratory stream, and olfactory bulb.

Example 10

Prospective Identification and Phenotype-Specific Purification of Multipotential Neural Progenitor Cells from the Fetal Human Forebrain Human neural progenitor cells have previously been obtained and propagated from the first trimester telencephalic vesicles of aborted fetuses (Fricker, 1999). These cells may be both raised in neurosphere culture (Svendsen, 1997, Fricker, 1999, Vescovi, 1999), and immortalized (Flax 1998), permitting the in vitro expansion of neural precursor cell populations. Nonetheless, the relatively small number of cells in the small tissue samples of first trimester brain, coupled with the lack of specific selection of neural stem or progenitor cells, has limited the number of native progenitor cells that may be harvested through this approach. As a result, prolonged expansion under conditions of unremitting mitotic stimulation, often leading to karyotypic abnormalities and perturbed growth control, or frank immortalization with transforming oncogenes (Flax, 1998), have been required for expansion of these cells to numbers necessary for engraftment. As described above, a promoter-based GFP selection was used to achieve the specific selection, acquisition, and purification of multipotential progenitors in high-yield. These cells divide, apparently in a self-renewing fashion, and give rise to both neurons and glia under the culture conditions, fulfilling the basic criteria for neural stem cells. By combining promoter-based selection with a particularly abundant source of neural progenitor cells, that of the second trimester VZ, the need for extended expansion or immortalization was obviated.

Thus, the prospective identification and phenotype-specific purification of multipotential neural progenitor cells from the fetal human forebrain, using a promoter-driven GFP-based separation strategy is reported. By transfecting dissociates of the human VZ with plasmid vectors encoding hGFP, placed under the regulatory control of the nestin enhancer, a distinct progenitor cell type was selected. These cells were both mitotically competent and multipotential, though biased to neuronal development under the test conditions. By subjecting these cells to FACS, they were enriched in high yield and relative purity. Virtually all of the E/nestin: EGFP-sorted cells expressed either early neural or neuronal phenotypic markers at the time of their separation, and still incorporated BrdU in vitro. When xenografted to the fetal rat forebrain, most of the cells integrated as neurons in the resultant chimeric brains. In vitro, they retained multipotentiality under the culture conditions, with single cells generating neurons, astrocytes, and less frequently, oligodendrocytes. These cells could be propagated in serum-free media with FGF2, from which mitotic cells giving rise to neurons could be recovered after as long as 10 weeks in vitro. Thus, mitotic neural progenitor cells may be specifically identified, isolated, and enriched as such from the ventricular zone of the second trimester fetal human forebrain. These cells may be propagated as such after their virtual purification, and are competent to generate neurons in vivo as well as in vitro, as long as several months after the initial harvest of their parental founders.

Although preferred embodiments have been depicted and described in detail herein, it will be apparent to those skilled in the relevant art that various modifications, additions, substitutions and the like can be made without departing from the spirit of the invention and these are therefore considered to be within the cope of the invention as defined in the claims which follow.

LIST OF REFERENCES CITED

The following is a list of references cited in this application. All of these citations are hereby incorporated by reference.

Barami, K., et al., *J Neurobiol* 28:82-101 (1995).
Brustle, O., et al., *Nature Biotech* 16:1040-1044 (1998).
Eriksson et al., *Nature Med* 4:1313-1317 (1998).
Flax, J., et al., *Nature Biotech* 16:1033-1039 (1998).
Frederiksen, K., et al., *J Neurosci* 8: 1144-51 (1988).
Fricker, R., et al., *J Neurosci* 19:5990-6005 (1999).
Gage, F., et al., *Ann Rev Neurosci* 18:159-192 (1995a).
Gage, F., et al., *Proc Natl Acad Sci USA* 92:11879-11883 (1995b).
Goldman and Luskin, *Trends in Neurosci.* 21(3): 107-14 (1998).
Goldman, *J. Neurobiol.* 36: 267-86 (1998).
Goldman, et al., *J. Neurobiol.* 30(4): 505-20 (1996).
Goldman, S., *J. Neurosci* 10:2931-2939 (1990).
Goldman, S., *The Neuroscientist* 1:338-350 (1995).
Goldman, S., In: *Isolation, characterization and utilization of CNS stem cells.* F. Gage, Y. Christen, eds., Foundation IPSEN Symposia. Springer-Verland, Berlin, p. 43-65 (1997).
Goldman, S., and Nedergaard, M., *Dev Brain Res* 68:217-223 (1992).
Goldman, S., and Nottebohm, F., *Proc Natl Acad Sci USA* 80:2390-2394 (1983).
Gritti, A., et al., *J Neurosci* 16:1091-1100 (1996).
Heim, R., and Tsien, R., *Current biology* 6:178-183 (1996).
Hoshimaru, M., et al., *Proc. Natl. Acad. Sci.* 93:1518-1523 (1996).
Kilpatrick, T., and Bartlett, P., *J Neurosci* 15:3563-3661 (1995).
Kirschenbaum, B., et al., *Cerebral Cortex* 4:576-589 (1994).
Kirschenbaum, B., and Goldman, S., *Soc Neurosci Abstr* 317.8 (1995b).
Kirschenbaum, B., and Goldman, S., *Proc Natl Acad Sci USA* 92:210-214 (1995a).
Korr, H., *Adv Anat Embryol Cell Biol* 61:1-72 (1980).
Kuhn, et al., *J. Neurosci.* 17(15):5820-29 (1997).
Lois, C., and Alvarez-Buylla, A., *Proc Natl Acad Sci USA* 90:2074-2077 (1993).
Lothian C., et al., *Eur J Neurosci* 9:452-462 (1997).
Luskin, et al., *Molec. & Cell. Neurosci.* 8:351-66 (1997).
Marusich, M., et al., *J Neurobiol* 25:143-155 (1994).
Menezes, et al., *J. Neurosci.* 14(9):5399-416 (1994).
Morshead, C., et al., *Neuron* 13:1071-1082 (1994).
Palmer, T., et al., *Mol Cell Neurosci* 6:474-486 (1995).
Pincus, et al., *Neurosurgery* 42:858-68 (1998a).
Pincus, et al., *Ann Neurol.* 43:576-85 (1998b).
Reynolds, B., and Weiss, S., *Science* 255:1707-1710 (1992).
Richards, L., et al., *Proc Natl Acad Sci USA* 89:8591-8595 (1992).
Rossant, J., et al., *Genes Dev* 5:1333-44 (1991).
Roy, N., et al., *J Neurosci* 19:9986-9995 (1999).
Roy, N., et al., *J Neurosci Research* 59:321-331 (2000a).
Roy, N., et al., *Nature Medicine* 6:271-277 (2000b).
Sakakibara, S., et al., *Developmental Biology* 176:230-242 (1996).
Sakakibara, S., et al., *J Neurosci* 17:8300-8312 (1997).
Sakurada et al., *Development* 126:4017-4026 (1999).
Sambrook et al., *Molecular Cloning: A Laboratory Manual,* 2d Edition, Cold Spring Harbor Laboratory Press, Cold Spring Harbor, N.Y. (1989).
Sturrock, R., *Adv Cell Neurobiol, vol.* 3, Academic Press, New York, p. 1-33 (1982).
Svendsen, C., et al., *Exp Neurol* 148:135-146 (1997).
Vescovi, A., et al., *Neuron* 11:951-966 (1993).
Vescovi, A., et al., *Exp Neurol* 156:71-83 (1999).
Wang, et al., *Ann. Neurol.* 44:438 (1998).
Wang, S., et al., *Nature Biotechnology* 16:196-201 (1998).
Weiss, et al., *Trends Neurosci.* 19:387-393 (1996).
Zimmerman, et al., *Neuron* 12:11-24 (1994).

What is claimed:

1. An enriched preparation of human fetal multipotential neural stem cells extracted directly from the brain of a human fetus without initial epidermal growth factor expansion, wherein the enriched preparation is capable of: (1) generating neurons, astrocytes, and oligodendrocytes and (2) being propagated for at least 7 weeks, and wherein the enriched preparation comprises a transcriptionally active nestin enhancer or musashi promoter.

2. The enriched preparation of human multipotential neural stem cells according to claim 1, wherein the multipotential neural stem cells are from the ventricular zone.

3. The enriched preparation of human multipotential neural stem cells according to claim 1, wherein the multipotential neural stem cells are from the hippocampus.

4. The enriched preparation of human multipotential stem cells according to claim 1, wherein a musashi promoter, if present, is capable of functioning in all cells of the enriched preparation.

5. The enriched preparation of human multipotential neural stem cells according to claim 1, wherein the enriched or purified preparation of isolated human multipotential neural stem cells is capable of being propagated for at least 10 weeks.

6. The enriched preparation of human multipotential neural stem cells according to claim 1, wherein the preparation is a purified preparation of isolated human multipotential neural stem cells.

7. The enriched preparation of human multipotential neural stem cells according to claim 1, wherein the nestin enhancer, if present, is capable of functioning in all cells of the enriched or purified preparation.

8. The enriched preparation of human multipotential neural stem cells according to claim 1, wherein the multipotential neural stem cells are self-renewing.

* * * * *

SEQUENCE LISTING

<160> NUMBER OF SEQ ID NOS: 2

<210> SEQ ID NO 1
<211> LENGTH: 52216
<212> TYPE: DNA
<213> ORGANISM: Homo sapiens

<400> SEQUENCE: 1

```
gatccgcccg cctcagcctc ccaaagtgct gggattacag gcatgagtca cggctcccag        60
tagtttattt tttgagacag agtctcactg tgttgcccag gctggagagc agtggcagat       120
```

```
cttggctcac tgcaacctcc gcctcccagg ttcaagcaat tctcctgtct cagcatcccg    180
agtagctggg attacaggca cccgccacca tgcccggcca agttttgtat ttttagtaga    240
gatgaggttt cactatgttg gccaggctgg tctcaaactc ctgacctcag gtgatgcacc    300
cacctcagcc tcccaaagtg ctgggattac aggcaggaac caccgcacct ggcttctttt    360
ctttttaatt aagctttatt ggccaggcat ggtggctcat gcctgtaatc ctagcacttt    420
gggaggccaa ggcaggagga ttgcttgagc ccggaggtc aagatcagcc tgggcaacat     480
agtgagaccc acgtctctac aaaaaataca aaagttagcc aggcatggtg gtgcacacct    540
gtagtctcag ctactcggaa ggtggaggca ggaggatcac aggagctcag gaggtcaatg    600
ctgaataagc catgattgcg tcactgcact ccagcctgga caacagagtg agaccctgtc    660
tttttttttt tttttttttt ttgagacgga gtctcgctct gttgccgagg cttgagtgca    720
gtggcgcgat ctcggctcac tgcaagctcc gccttccggg ttcacaccat tctcctgcct    780
cagcctcccg agtagctggg actacaggcg cccgccacca cgcctgacta atttgtttt     840 tgtattttta gtagagatgg gtttcaccg tgttagccag gatggtctcc atctcctgac     900
cttgggatcc gcccacctca gtctcccaaa gtactgggat tacaggcgtg agccaccatg    960
cccagccgag accctgtctt aataaacaaa caagcaaaca aaaactttat ttttggagc    1020 agttttaggt tcacagcaat attaagcaga aggtacagag atttcctata tatctctctc    1080
ctctccagac acaggcacag cttccccat tatcaacgta ccctacatga gtggtgtttt    1140
gtttgtttgt tgtttttga ggcagagttc tgctcctgtt gcccaggctg gagtgcagtg    1200
gcgtgatctc ggctcaccgc aacctccgac tcccgggttt aagcgcttct cctgcctcag   1260
cctcacaagt agctgggact acaggcacgt gccaccacac tcagctaatt tttatatttt    1320 ttctttttt gttttttgag acagagtttc gctcttgtct cccaggctag agtgcaacgg     1380
tgcgatctca gctccctgaa acctctgcct cccaggttca agcaattctc ctgcctcagc    1440
ctcccgagta gctgggatta caggcacttg aacttctgac ctcaggtgat ccacctgcct    1500
cgacctccta aagtgctggg attatacgca tgagccaccg cgcccagcct gtatttttag    1560
tagagacaga gtttcaccat tttggccagg atggtctcta tcttctgacc tcatgatccg    1620
ccctccttgg cctctcagag tgttgggatt acaggcgtga gccaccgcac ccagcttgta    1680
tttttagtag agacggggtt tcaccatttt ggccaggatg gtctctatct tctgatgtca    1740
tgatgcgccc gcctcggcct ctcaaaatgt tgggattaca ggcgtgagcc accgcgccca    1800
gctatggctc actcttgatg ctgcacattc tgtgggtttg gacagatgta taatgatatg    1860
taccaactaa cttttggag tctttccaaa gcattcaact gcattcatag aaacatccgt     1920
cttcttttcc gactcatatt ttatcagttt gtcctatata attataagat ttaattacaa    1980
gagtaactga tggccgggcg cagcggctca tgcctgtaat cccagcgctt gggaggccg     2040 aggcaggcag attacttgaa gtcaggagtt cgagaccagc ctggccaaca tggtgaaaca    2100
ttgtctctac taaaaataca aaaattagcc aggcatggtg gtatgtgccc gtaatcccag    2160
ctactccgga ggctgaggca caagaatcgc ttgaagctgg gaggtgaagg ttgcagtgag    2220
ccgagattat gccactgtac tccacccttg gcaacggagt gagactccgt ctcaaaaaaa    2280
ggagtaactg atgggagaac caaccccct gactcttgat aaccacatgg tcacatcttc     2340
actcaacagg agttagtggc ttgtcacact agaaatgaac ccaccagctg ctgtgggcct    2400
cacattgttc tagattttat agcaggcaaa gcgagcattt gttaagctag tgagccaatt    2460
ccagggattt tttttttttt tttttggta gagacggggt cttgccaagt tgcccaggct    2520
```

-continued

```
gcttctgaac tcttggcctc aagcaatcct cctaccttgg cctctcaagt cgctgggatt    2580
acaggaatga gccaccacgt ctggcctccc atgaattttt aatccagtga gttggtttat    2640
ccagaaagct ttccctatac aaccataaac aaaaagtata acaaaaagtg atctcactgg    2700
agtaattgaa gtgaccaggg ttgattctgt ccttttttact catttatatt ttccagcttt    2760
ttgtaccttt aatgtagatg aaagttggga tgtgtgtgtg tgtgtgtgtt ttgaagactt    2820
aattaagact atagggtcat atatgccctag ggctgaatga actatactag acttcaaatt    2880
ccttgaatcg agcgtattgt aaaaggctgg acttgacata acatgcctaa ttgggataat    2940
gacagtggaa aaatcttggt attaggccat gtttctcaaa gtgtgcccca ggactggcag    3000
cagcaacatc gcctgggaac ttgctagaaa tgtaaattct tgggagccgc cccagaactg    3060
ctgcatcaga tactttggga tggggttcag aaatctgtgt ttgaacaagc cctcaaagg    3120 attctggtgt tccctcaaat taacagatgg ctcacctcac aggtttacca ctcagaggct    3180
gtgtgatctc agacaagtca ctgcacctct ctgaacctat ttcttctctg ataagaataa    3240
tagcagacct accttacaga atgattgtga aggttaaatt aaataatatg tgtaggcaca    3300
gtgcctgaca cacagaagac actcactaaa tgttaggaaa gctaatatta tttttaggaa    3360
ttcatgagtg gcagctctaa ttagggtgaa aaacatggga gtagggtgtg gtagctcaca    3420
cctgtaatcc cagcactttg ggagactgag gtgggagcat cacttgagtc caggagttgg    3480
agaccagtct ggggaatata gtgaaactcc tgtctccaca aaaaatttta aattagctgc    3540
atgtggtagt atgtgcctgt agttccagct actcaggagg ctgagctggg aggatggctt    3600
gagctcagga gattgaagcc gtagtgagcc gtgattgtgc cactgtactc cagcttgggc    3660
aactgagtga gactttgtct caaaggaaaa aaaaaggaa gaaagaaaaa catttgggag    3720
aaaagaggaa aagatgttat ggagtttaaa atatttctgg tggggaacag tggctcatgc    3780
ctgtaatcac agcactctgg gaggcctgag gcaggaggat tgcttgagtc caggagttca    3840
agaccagcct gggcaacata gtaggacccc atctctataa aaataaataa gtacctataa    3900
tcccagtact ttgggaggct gaggtgggcg aatcacttga ggtcaggagt tcaagtccag    3960
cctggccaac attgtgaaac cccgtctcta ctaaaaatat aaaaattacc cgggtgtggt    4020
ggtgggcacc tgtaatccca gctactcggg aggctgagac aggagaatca cttgaaccca    4080
ggaggtggag tctgcagtga gcagagatcg caccactgca ctccagcctg gcaacagaa    4140 tgagactcag tctctaaata aataaattac aaactatttc tgactaggca ctttgacctt    4200
attatgtacc ttcaccctcc gaataaacat gttaaagtag aagcaggtat cattatattc    4260
cctgcccatt tcacagatat ggagactgag ggttggtggg gctgaatgat agctaagaag    4320
tagcagagct gggacctaac catatccatg tgccccacct cactctcagc ctcaaacaga    4380
tgcaggcaga ttcccactc accagagcct ccccccttcc ccaaaccatc tgcccctctg    4440
attgttttct tggggctcta gaagtcaggc ctttcagctc atctttactg cacagggatt    4500
tctccattgg ccggtttctg ctgcctgaga cccttgccca gccccagcca acaccagcat    4560
gattcacttt ctgtttttt gagatggagt ttccctctcg ttgcccaggc tggagtgcag    4620
tgacgtaatc tcggctcact gcaacctctg cctcccagat tcaagcaatt ctcctacctc    4680
agcctcccaa atagctggga ctacaggagt gcaccaccac acctggctaa ttttggtact    4740
tttagtagag acagggtttc gccatgttgt ccaggctggt ctccaactcc tgacctcagg    4800
tgatgcaccc tcctcggtct cccaaagtgc tgggattaca ggtgtgagcc accgcgccca    4860
gccatgattc acatttgaac ctgagaccag agctcataaa tgcattaatt cattaatttc    4920
```

```
tcaaacattc tacatgctat gggataggta cttggggtac agagaggagc aaaatggaca   4980
ttggccctac tgcaaagaac ctgaatattc acgtggagta tttcccatca ctttctaggc   5040
ctagccttga tttttgctga acccgggcca aggcagaggc acaggtgcct ccacagagca   5100
gaaccagaca aatattgtac actatagtca gtgcagggat gggaacacaa cctggctctg   5160
taagaggcca gaagaggccc ttgatcaatc tgcgggtgga agggaatcca tgaagacttc   5220
ctgcaggtgg tgacctctga ggctgattag gaggtgtttg ccatagtgtt tcatcattt   5280 ctcattttat agatggcaaa atgagtccag agagaatgac ttagcccatg tattcaatca   5340
attgagcaaa catttcccta atatctacat tccccattat tgagccctga gcctggggat   5400
acagaggtga ataaggttaa caggcctgct agagggaatg gtatagagag gcctcaagta   5460
tccaggatac ctcaccaatc actgcccatt ggcctctgtt ttttttgtatg tattttattt   5520 tattattatt attttgtaaa ttttgagaca tggtctcact ccgttgtcca ggctggagtg   5580
cagtggtgga aatataactc actgcagcct caattcccta gcctcaagca atcctcccat   5640
ctcagcctcc ccactagcaa ggactacagg catgtgccac tgtgcccagt aatttttt   5700 ttttttttttg gtagagatag gatcttgcca tgttgcccag gctggtcttg aactcctgag   5760
atcaagagct cctcccacct cggcttccaa agtgctggga ttacagacgt gagccaccac   5820
acctggccta ttttatttta cctttttaaa agtcaggatt ggccgggcac ggtggctcac   5880
acctgtaatc ccagtactct gggaggccga ggcaggtgaa tcacctgagg tcaggagatt   5940
gagaccagcc tgcccaatat ggcaaaaccc catctctact aaaaaataca aaaattagct   6000
gggcatggtg gtgcacacct gtagtcccag ctactcagga ggctgaggta ggagaattgc   6060
ttgaacctgg gaggtggagg ttgtagtgag ctcagaccgt gccactgtag tctagcctgg   6120
gcaacagagc gagactcttt tcaaaaaata aatacataaa taaaattaaa aatgataaaa   6180
gtcatggtta ttgcagtata catacagtaa aattctcccct ttttagtaca tatgtggcaa   6240
atgcatagtc ctgtaatcat catcacaatc aagacacaaa gacacaggtc atcatttgaa   6300
tctttttttt tttttttgag tcggaaccct gccccttttac cgaggctgga gtgcagtggc   6360
gtgatcttgg ctcactgcaa cctctgcttc ccaggttcaa gcaattatcc tgcctcagcc   6420
tccggagtag cagggaccac aggcacgcac caccacgctc agctaatttt tgtatttta   6480 gtggagacag ggttttcacca tgttggacag actggtcttg aactcctgac ctcaggtgat   6540
ccacccacct cagcctccca agtgctgggg attataggtg taagccaccg cgccggccc   6600 atcatttgaa tcttatgttc atcccacttc ctgagtccaa gccttcccct taattcactg   6660
tgttatcttg ggcaactctt gccctcttttg aacctcagtt tcttcatctt taaaatggga   6720
accataaaac caccttaca ggattgctgt gaggatggtt gcctggcaca cagtaagcgc   6780
tcaattaaca ccagctttta ttcacactcc ttcccttttc tagccctttc aaactccccc   6840
tctccctctg gtctctctcc ttctgggtct gtctctccct ctcacagaca cacacacaaa   6900
cacactccct ctgggacaca cacacacact ctgggacaca cagggaca cacacacaca   6960 cacactccct ctggggaca gacacacaca cacacacaca cacacatttt gaagcctctt   7020
gtttcccaga gaggttttat ttataggctg tgcctcattg tgaatgtgaa aaggagaaag   7080
cccaggccct ccgtagacct ttcatgtgta aatcagcccg ggcctggagc acgggtcac   7140 caggaggagg atttcactct taattactcc tagagaaagc gggcgggaag gaggcctctc   7200
tgggagccca gggcctcgcc tggcgccggg ccctcgctc ccaggctgg ggagcgctgg   7260 ctctccaggg ccgggatcag gctagagctg gggccaacac ttcctgggtc tggccttgat   7320
```

```
ttctgctgaa cctgagccaa ggcagaggcg caggtgcctc cagggagcag ggccccaagt   7380
aggtttcttt gagggcaagt tgtttggaca cagaaagagg gcacacagct tgacagggtt   7440
ggagatagca agggtgatct gctgaagtgc caggcagggg taattaaaca aaattttaa    7500
ggttttaaaa ttcatttctg atgtaaaaat cacacactct attatagaaa aatgtttgaa   7560
aagattccta tccaggccgt taacattgtt tatttcgagg ggtaagtttg tttgtttatt   7620
tattttgag acggagtctc actctgtcat ccaggctgga gtgcagtggg caatttcag    7680
cttcctgcaa cctctgcctc ccgggttcaa gtgattctcg tgtcctcagc ctcccgagta   7740
ggtgggataa caggtgcgcg ccaccatgcc tggctaattt ttgtattttt agtagagagg   7800
gggtttcacc ctgttggcca ggctggtctc acctcaggtg ttccgcccac ctcggcctcc   7860
caagtgctgg gattacaggt gtgagctact gtgcctggcc agcgggtaaa tttagaggta   7920
aagaaaggga cattattaac attttttatac atttttttatt tttaaactta ttacaatgac  7980
tatgtattgc ttttttaatta aaaagcacaa cgttattttt catagtatcc atggtactgt   8040
tttctgatta cagaaaagaa attaatattt gatataagac attgagaaaa taaagtataa   8100
aaactatctg tggctccatg aaagaatatc attttttttc ttccttgatt ctgcattaaa   8160
ggaaatcaaa gaaaacact tttaatattt aagtatatgg ccatagatga tttatttctt   8220
ggctaagtag ttcattttta ttttatgttc attttgcata cttatactgc acaaacactt   8280
tgggtacaac ttaacacact gaggttttct ttttttttct tttattcttt ttatttattt   8340
atttattttg agtcggggtg cagtggtgtg accttggctc actgcctcct ctgcctcctg   8400
ggttcaagcg attctcctgc ctcaacctcc tgagtagctg ggattacaag cacgcgccac   8460
cacacctggc taattttgt atttttagta gagaccgggt ttcaccatgt tggccacgct    8520
ggtctcgaac tcctgacctg gtgatccacc cgccttagcc tcccaaagtg ctgctgggat   8580
cacaggcgtg agccatggca tctggcctca cactgaggtt ttttttcttcc attcatcttt  8640
tctcttcttg tgctttatat acagtcgtca ttcagtgtcc ctgggggatt agttctggca   8700
cctccctcag ataccaaaat ccacagatgt tcaagtccct gatataaaat ggcatagtat   8760
ttgcatatta tctatgcata ccctcctgta tactctaagt catttctaga ttacttatga   8820
tccctaatac aatgtcaatg cccggtaaat cattgttata ctgtgttttt tagggaataa   8880
tgataaggaa aaaagtctgt ctatgttcaa tacagatgca gggttttttc ccaaatattt   8940
tccatcaagg ttggtggagt ccagggatgt ggaatgaata aatacagagg accacctata   9000
tatatgtatg ttactggatg gcattatttt gaaatatgaa atacacaagc ccttgggtc    9060
cagcaattcc acatctaaaa ttctattcat gtgagtagga gtaggtaaat agtagaaaca   9120
aatttgttca ttttgaaggt gtttataaaa gcaaaggcta gcaacaaact tgatggtcat   9180
cagtaggaaa ttaagtaagt aaatcatcat gtaactttac agtgaaatgt tttgtagtca   9240
ttataagagt atatcggctg gcgtggtgg ctcaggcctg taatcccagc actttggaa     9300
gccgaggcgg gtggatcacg aggtcaggag ttcaggatca gcctagccaa tatggtgaaa   9360
ccctgcctct actaaaaata caaaaattag ccaggcgtgg tggtgcgcac ctgtaatccc   9420
agctactagg gaggctgagg caggagaatc actcgaaccc gggaggcaga ggttgcagtg   9480
agccaagatc gtgccactgc actccagcct gggcgacaga gcaaggctcc atctcaaaaa   9540
aaaaaaaaaa aagaaagaa agaaaaagaa aaaagagta tatcaggcca ggtgcagcga    9600
ctcacgcctg taatcccagc catttgggag gctgaggcgg gtgtatcact tgaggccagg   9660
agttggagac cagcctggcc aacatagtga aaccctgtct ctactaaaaa tacaaaaatt   9720
```

-continued

```
agccgggcat ggtggccctc acccataatc ccagttactc gggaggctga ggcatgagaa    9780
ttgcttgaat ctgggaggca gaggttgcag tgagccaaga tcacgtcact gcattccagc    9840
ctgggtgaca gtgagactcc gtctcaaaaa aaaaaaaaaa agagtatatc atacatgcaa    9900
agatatccaa aaatctgtac tatagtaaat aactaagcaa gttccaaaat catttggatt    9960
gtgtgattct atatctattt ttgttttgtt ttgtttgaga cggtctcact ctgttgccca   10020
gactagagtg caatggcgtg attataccte actgcagcct cgacctcttg ggctcaagtg   10080
atcctcccat ctcagcctcc caagtagcct atatctattt tttaaaatat aataatcata   10140
tctaagtata taggcatgga acatttttgg aaggatatac atgaaattgg taacagttac   10200
atttagggaa ggagtctaag gggtaaagaa cttttacttt ttcatcttat acctttgtgt   10260
actgacgcat ttttttcttt taatgtgagc acatgttaca tttgtaattt ttaaaaacta   10320
gctaatagaa atgtggttta gggctggatg cagtggctca tgcctgtaat ccctacacat   10380
tgggaggctg aggtgggtgg atcacctaag gtcaggagtt caggacaagc ctggccaaca   10440
tggtgaaact ctatctctac taaaaataca aaaattagcc ggggtggtg gcaggcgcct   10500
gtcatcccag ctgcttggga ggctgaggca ggagaattgt ttgaacccgg aaggcagagg   10560
ttgcagtgag cagagatcat gccactgcat atcagcctgg gtgacagagc aagactctgt   10620
ctcaaaaaca aaacaaaaca aagaaatgt ggttttgcta tatataattc taatatatat   10680
ttattaaaga aaatacaggc cgggcacgga ggctcacacc tgtaatccaa catggtgaaa   10740
ccctgtctct actaaaaata taaaaattag ctgggcatgg tgaggcgcac ctgtagtccc   10800
agctactcag gaggctgagg caggagaatc gcttgaactt tggaggcgga ggttgcagtg   10860
agcagagatc tcgccactgc actccagttt ggcaacagag caagactcca tctcaaaaaa   10920
aaaccaaaaa aacaaaaaat gtccattaaa taaacacagt ttcttaaaga aatagtgttg   10980
attaaataaa atataatccc ccatattatt caaggcaacc atattaacat tttaatttat   11040
ttccttctag ttttctctat atatatattt atacattttt aatattttac aaatttttt   11100
ttgagacaga gttttgccct gttgcccagg ctggagtgca gtggtgcagt cttagctcac   11160
tgcaacctct gcctcctggg ttcaagtgat tctcttacct cagcctctgg agcagctggg   11220
actacaggca cacgccacca tgcccaacta agttttgtgt tttagtaga gacggagttt   11280
cactatattg ggtaggctgg tcttgaactc ctgatctcat gatccaccca ccttggcctc   11340
tcaaagtgct gggattacgg gcgtcagcca ccgcaccagg acctttttt ttttttttt   11400
tttttttga gacaaagtct tgctctgtca cccaggctgg agtgcagtgg catgatcttg   11460
gctcaccaca acctcttcct cccgggttca gcaattctc ttgcctcagc ctcccaagta   11520
gctgggacta taggcacaca ccaccatgcc cagctaattt ttatattttt agtagagaca   11580
ggggtttcac catgttagcc aggatggtct cgatctcctg acctcgtgat ccacccgcct   11640
cggcctccca aagtgctggg attacaggca tgagacaccg tgcccggcga cacctacaa   11700
ttctttaaac tcccaacaac tcaaaggaac agatattatt attactccca tttgcagatg   11760
ggtaagtaga ggcacagaaa gatgagagga tttgcccaaa gacttggctg gtatttggca   11820
gaaccaggat tcaaacccaa caggcaagag cagagttgta cacttgacct agctattctg   11880
ctattctgcc taatgaggtt cttttttctt ttcttttctt tttttaaat ttttttttat   11940
tttttgagac agagtctcac tctgttgccc aggctggaat gcagtggtgc gatctcggct   12000
cactgcaacc tccagctcct gagttcaagc aattctcctg cctcagcctc ttgagtagct   12060
gggattacag gtgtgcacca ccacacccgg ctaatttttg tatttttagt agagatgggg   12120
```

```
tttcaccatg ttggccaggc tggtctcaaa ctcctgacct caagtgatct gcctgccttg   12180
gcctcccaaa gtgctgggat taccaggcgt gagccaccgc gcccggccct aatggggttc   12240
tgacaaaatc caggaattca gtgcaggbtg ggcggacctg tgagtgtgtg agtgagggat   12300
atgcgtactt gtggagccac agatatgcac atgtgtactc acgtgttcac cgtgagtctg   12360
acggcgtggg tgcatgcatg tgttaaccag tgctctgctg acatcatggt gcccaagcac   12420
gtagagatgt atgtgcccat ggattcccct gtccaggctc ccacaggacc tatctccttg   12480
gtttctccac cttccccttg gtacacagga ggcatgagtg tccaggaggg gccagggttt   12540
ggattccaaa gcccagctgc cacttcctta ttcccaccat gtctcccaag agtagttagg   12600
gtctggactc ttaaaacatc aagctgggtg ggaggcggtg gctcacaccc ttaatcccag   12660
cactttggga ggccgaggtg ggtggatcac ttaaggtcag gagttcggga ccaacctggc   12720
caacaaggca aaactccgtc tctactaaaa atacaaaaat tagctgggca tggtggcaca   12780
cgcctgtggt cccagctact tgggaggctg aggcaggaga attgcttgaa ccccggaggc   12840
ggaggttgca gtgagctgac atcatgccat tgcactctag tatgggcaac agagccagat   12900
tctgtctcaa acaaacaaaa aaacctcatc aagctggcca ggcacaatgg cttacacttg   12960
taatcccagc actttgagag gctgaggcag gaggatcact taagcccaaa gtttgaggc   13020 tgcagtgagc tatgatcaca ccactacact ctagccgggg tgacagagca agaccttgtc   13080
tctataaaaa ataacaaaat aaaacattag ctcttgcagg gcgcggtggc tcacgcctgt   13140
aatcccagca ctttgggagg ctgaggcagg cggatcacaa ggtcaggatt tggagaccag   13200
cattgccagc atggtgaaac cccgtctcta ctaaaattac aaaaaattag ccgggcatgg   13260
tggcacacct gtgatcccag ttactcagga ggctgaggca ggagaattgc ttgaacccag   13320
cagacagagg ttgcagtagg ccaagatcac gccattgcac tccagtctgg gtgacagagc   13380
gagattccat ctcaaaaaaa aaaaaaatca gctctttatg aagtagagtt ggcatatggg   13440
ccagggaagt cggagaacaa tgtggttttc cccaggaggc agcacccaca gcttttagcc   13500
ctatctggcc tccactgtgg gtggctgata tctactacca cagtggaggc catatggtcc   13560
tggttaagag taagctgtaa agtgaaactg ttgggttcaa atcccagctt tgccacttag   13620
ctgtgtgatt tcagcaactt actctcggat cctctacttc catccctgtg aagtgggagt   13680
attataatag caacaacttt gaagggtttg gtattttaaa tttattttta ttttttattt   13740
tatttatttt tttaatagag acagggtctc cctatgttgc ctaggctggt ctcgagcccc   13800
tgggctcaag tgatcctgcc acctcggcct cccaaagtat tgggattaca ggtgtgagcc   13860
acagtggctg gcccctgaa ggattgtcg taaggctgaa ataatgctga gctcaaactc   13920
agtgttcaat aaatgttagt tttattacta ttttgaaccc atactagaca agtaaagggc   13980
agagaaatgt gcttttccag aagacagtgc ctttgtcata cgggtaaatt atccaacctt   14040
gtgaaacagg tattattttc ttttcttttt tttgagacag agtttcactc ttgtcgccca   14100
ggctggagtg caatggcatg atcttgcctc actgcaacct acgcctccca ggttcaagcg   14160
agtctcctgc ctcagcctcc caagtagctg ggattacagg tgtgtgccac catgcccagt   14220
taatttttgt atttttagta gagacggaga ttcaccatgt tgtagacatg tttgtatgtt   14280
tagtagagac ggagtttcac tggtctcgaa ctcctgacct caggcaatcc acccacctca   14340
gcctcccaaa gtgctgggat tacaggcata agccaccacg cttggcccca ttttatttta   14400
ttttttgttt tgttttaaag aaatagagat gggatctcgc tatgttgccc aggctagtct   14460
caaagtcctg ggctcaagtg atcctcctgc ctcagcctcc caaagtgctg gaattacagg   14520
```

```
tgtgcaccac tgcacccagt ctgtgcccat tttatggatg aggagactga ggctcagcag      14580
tatgcagtaa cttgtcccag gtcacagagc aagtaagtaa caaaaccaga tttcacttgc      14640
tggtctgcct ccaattccag ggctctttct gccacccaac agctgccttg ttgtttggcc      14700
tagaagcttc atcctgtaag ctctgatttg cgcagattat ctgccaccta catgtctttc      14760
tctcatgttg cctactcaca agagaatatg tagggatttg caggtggtca gattttatgg      14820
gaaaaaaaat agacatttcc acacagaaaa gaaactccag ggagacagtt gagacagtta      14880
ggcagggagt tcttggagga aaatgggagg ttcaaaaggc aattaatgct actgtctgaa      14940
actgtaaaca gatagttact ggctctgaca ccaccagcac acagacaaaa ggcagacaga      15000
aacagcgcac cacaaggaag ctgggcatag actacgccca gggtggaaat taaatgtttt      15060
cctgaaagca gaaaggaaaa ccatagttaa agccaatcca tgactctaag tctatgactc      15120
catgacagca taagtccagt gagtaaaggc ccttcatttg cacctaggcg ttgttatgaa      15180
tcttaaggcc ttactccaca ttctctcttg acctaagttt gtaaaacaaa agtaataatt      15240
agaagtgact cttcagcata tactgttatt ttaatcaaag atagatatac acacacacta      15300
tatatgtgtg tgtatatatg tatatagagg atctatagta tatatcctct atatacatat      15360
atattataaa tatatatgta tatatattta tctatatata cgtatatgtg tatatatgta      15420
tatatgtata tagagtatat atatttatac tctatataca catatacata tatatacact      15480
atatatatgt gtgtgtgtgt gtgtgtgtgt atatatatat aacagacatg agccaccaca      15540
cctggcccca ttttgtttta tttcttgttt tattttcaat aaatagagat gggctctcac      15600
tatgttgccc aagctggcct caaactcctg ggctcaagtg atcctcctcc ctcagcctcc      15660
caaagtgctg aaattacagg tgtgcaccac catatatata tatggagaga gagaaagatg      15720
tgtggctggg cacagtggct cacatctgta ctttgggagg ccgaggtggg aggatcgctt      15780
gaggtcaggt gttgaagatc agcctgggca acatagcgag accctgtctc tacaaaacaa      15840
aacaaaacaa atatacatat attgtttgtt ttgtttcgta gatacggagt ctcactatgt      15900
cactcaggct ggagtgcggt ggcgtgatct tggctcactg caacctccac cttccgggtt      15960
caagcgattc tcttgcctca gcctcctgag tagctgggac tacaggctca cgccaccgca      16020
cctagctaat ttttgtattt ttagtagagt cagggtttca ccatattggc caggctggtc      16080
tcgaactact gacctcatga tccacccatc tcagcctccc aaagtgctgg gattacagac      16140
gtgagccacc gcgtctggcc catatatagc acacgcctgt aatcctataa tcccagcact      16200
ccgggaggct gaggcaggta gatcacctga ggtcaggtgt tcgagaccag cctgaccaat      16260
atggtgaaac cccatctcta ctagaaatac aaaaattagc tgggcgtgat gctgtgccct      16320
gtagtctcag ctactcagga ggctggacgg agaattgct gaacccagg agatggaggt      16380 ttcagtgagc tgagatcggc cactgaactg tggcctgggc aacagagcaa gactccgtct      16440
caaaaaaaaa aaaaaatat atatatat atatatatgt acatatat agacagagag      16500 agagagagag agcacacaca ttggcacatt gttggcaagt ttcctcagca ttcctagttg      16560
taaatgacag aaaactcact gatgcaaaca aagcaaagaa tcataataat tattattatt      16620
tactgattta caactggatc aaggagttca aagattccaa ttcatgtcct gccatgtct      16680 tgactctgct ttcttctgtg gtttcaatct cagcagaca cgctcctccc cagggtgaca      16740
agaaggctct caggagctcc acccatgctt tttcctgttg gttaaaaaac agtgcctctc      16800
tccagcaaaa atctcaagtc tcccactgat tggctcccat tggtcatat gcctgttctt      16860 caaccaatcc tgtggccagg ctggatccca gggccaaccc tggaggcaca ggtgggcaga      16920
```

```
gtaagttcca tccaagatac aggaactgat attgggagag ggagagttcc ccagggaaaa    16980
ctgggggggct gtttccagaa gacacatgtt caccatctgg tagttgctgc ctctctgtta   17040
accaaattta atgagaagct gtcatcagga gtaattttct tgtatttta ctagagctgg     17100
ggcttcacca tgttgcccag gctggtctcc aactcctaag ctgaggcaac tgcccacctc    17160
ggcttcctaa agtgctggga ttacaggcat ggccaccacg cctggccatg tttatttctt    17220
atcttcatct cacttcatca atgggcaaat tgacagagag gttaaggaat tggcccaagt    17280
ttatacagag agtaaggagt ggagccaggg catccttccc aaattctgtg ctttagtttc    17340
tccaggaact acagttagag ctgatctatc tctcagaatt gccagctccg tgccaatgag    17400
gaagccctga gccttctaaa ggaccaccctt gcaaggttaa ccaatgtggg atggcagata   17460
tcatccacac actcatgagg gtttatcctg agcagtgcc tggacactga gaggtgtgac     17520
aacaaggcaa gtctgatcca aggaccattg tggactcagg agctgagatt cctcggtagc    17580
cctgcttccc tacccacagg agtggaggag aaagagtgca acgcacagag aagtgccaag    17640
attgagcccc taacctgccg ctaaccagct gttatgtgtc ttgaataaac tcctttaaga    17700
tctctgtggc caggcacggt ggctcacgcc tgtaatccca gcactttggg aggccaaagt    17760
gggcggatca cctgaggtca ggagtttgag accagcctgg ccaacatggc aaaacctcgt    17820
ctctactaga aatacaaaaa ttagccaggt gtggtggtgc ttgcctgtaa tcccagctac    17880
ttgggaggct gaggcaagag aatcgcttga acccaggagg tggaggttgc agtgagccaa    17940
gattgcgcca ttgcactcca gcctgggcaa caagagcgaa actccatctc aaaaaaacaa    18000
acaagatctt tgtttctaca tccataaaat gggcataata acaccttcct cagaggttag    18060
cgaggattct attaaatact gcaggcaaaa taatacctgc ttggctgggt gcggtggctc    18120
atgcctgtaa tcccagcact cgggaggct gaggcaggag gatcgcttga gctcaggagt     18180
tcaagatcaa cctgggcaac atagaaagac ctcatctcta caaaaatat gaaaaattag     18240
ctgggtgtgg tggcgtgcac ctgtagtccc aggtactcag gaggccgaga tgggaggatc    18300
tcttgagcca gggaagtcaa ggctgcattg agccgagatc acgccagccc gggcaacaga    18360
gcaagatcct gtctgtaata gtaacaataa caataataat tcttgcttgt cacccagctg    18420
gtctccatga ggttagttgt ctccttcca tattatcccc cttctccatc ccccagactt     18480
agcaagagca aggcaagcgg agaaaggaaa gcatctttta tcttctccta gccggcctgg    18540
tgggggtctcc tccctcctc ctctgcccag catctgtaat agcaccaaat gagcacggaa    18600
cctcgcatca tgttcctggg tttgactccc agctcagccg tcctcttcct aggcttgtga    18660
ccttggataa gtccctgtca cccctctcag ctgaagaaca tgctccctca tcgagtctga    18720
tgaaaacgcc ctccataaac gtgcctgcca catggtttgt ttattctctg gatctgaaac    18780
ggtgaaagag gcagagctga gtaggtcggg ctgccttggg catggctttg gtcagcagag    18840
gggccggctt cacgccactt cccatctcct gaataattca tgacgaacaa aatgactggg    18900
ccagacctgg gccctccctc ctcctgtcgt gaaggcagaa aagtttctaa ttacagatca    18960
gccggccagc ctcccggggg cccctgggcg ctgcacacag ggggcattta tgggaagaga    19020
ccatggaggg gaggggttcg gtcccagctc cttccagaa gaaactcaac tccttttgaa     19080
attgtaacct tggcctgcta aggcccagga agggactggg gaaagaaact tagaagagga    19140
agagaaaacc ctgccgaggg gtcagagaga agcgcccaga aaaaaatgtc aggtcaaaga    19200
agggggctctg gggacgtcct ggcaagagga atacacaagc tgtcagggga ggagatttgc   19260
tcgagtcccg tggaaagcat gacaaagccg ggcttcaaaa ggaagctgtc cttcgaaaat    19320
```

```
acattgagaa agaataagat ctagcgttct accatacagt agggagacta gagttaataa   19380
tttgtcatag agttcaaaat tgcttggctg ggagcggtgg ctcacgcctg taatcccaac   19440
actttgggag gccgaggcag gcagatcacc tgaggtcagg agttcgagac cagcctgtcc   19500
aacatggcga agaacccgt ctctactaaa aaaatacaaa aattagctgg atgttgtagc    19560
gggtgcctgt aatcccagct acttgggagg ctgaggcagg agaatcacat gaacctggga   19620
ggcggaggtt gccgtaagcc gagatcacgc cactgcactc tggcctgggc cacagaatga   19680
gattccgtct caaaaaaaaa aaaaaaaaa aaaaatttg ctggaggaga ggaacggaga     19740
tgtttcccaa catgaagaag gggtgaatat ttgggttgat ggatgtccca gttatcctga   19800
tttgatcatc acacattgca tgtatgtatc aaaataccac atgtgccccc aaaatatgta   19860
ccattattat gtataacttt tttttttttt gagatggagt atcgctctgt cgcccagtcc   19920
tgagtgcagt ggcgccatct cagctcactg caagctccgc cccccgggtt cacgccattc   19980
tcctgcctca gcctccccag tagctgggac tacaggcgcc cgccatcacg cccggctgat   20040
gttttgtatt tttagtagag acggggtttc accatgttag ccaggatggt ctcaatctcc   20100
tgacctcgtg atccgcctgc cttggcctcc caaagtgctg ggattgcagg catgagccac   20160
cgcgcccggc ccatgtgtca ctttttttaaa aaaggaagat ttcttgactc caacaccaca   20220
gcctctcagt tacactacaa tttactcatt catctgtaaa atggggagat gcccaataat   20280
gctaccttac agcattattg aggagttaca caagtaaata aatgtcaagt gcttagaata   20340
ctgcctcaca cataaactaa aaatatatat tagtagttgt agagtttttt tttttatatt   20400
atgctccctc catagagtgg tcagtaaagg gtgaaggtga caagaagaga agatttgggg   20460
agattgttag agagaacaat gattgtgagg tagtttagta tagtgattaa gatgaggacc   20520
ccatacataa taccgtaata ataataataa aagaggtcag ctgcggtggc tcatgaccgt   20580
aatcccagca ctttgggagg ctgaggtggg cagatcgctt gagttcagga gttcaagacc   20640
agcctgggca acatggtgaa accctgtctc tactaaaact acaaaaatta gccaggcatg   20700
gtggagggtg cctgtagtcc cagctacttg ggaaagtgag gcatgagaat tgcttgaacc   20760
caggaggtga aagtttcagt gagccaagat gggcaacaga gcgtgactct gtccaaaaaa   20820
aataaataaa taaaataaaa aagaggccag gtgtggtgtg gtggctcacg cctataatcc   20880
agcactttgg gaagctgagg ggagtggatt gcttgagttc aggagttcaa gaccagcctg   20940
ggcaacatag tgagaccctg tctctacaaa aagtacaaaa attagctggg cgtggtggtg   21000
ggtacatgta gtcccaacta cttgggaggc tgaggtggga ggatcacttg agcctgggag   21060
gtggaggctg cagtgagcca agatcgtgct gctgctctcc agtctgggcg acacagtgag   21120
accctgtttc aaaaaaattt aaaaagtaag gactccagca ctagtttgcc tgggttcaaa   21180
tcccagctct gcctcttact agttgtgtga tcttggacag gtttgctgta ggtctccgag   21240
ctcctattca ctgtctgtaa taaacggtag ccactgcagt tagtggagag tggtgaacaa   21300
aatgaccaag gtccctgtcc tcatggagct tacagtctag caggaaggtt atactaatca   21360
agagcgttta ttgcatgcca actgtgtgca ggtcctgtgc acttggcaga cattctctta   21420
acgaaatttc acagaatcca cccctgtctt acagatgaag agggtgaaac tcaaagaggt   21480
cacaagcaga gagaggattt agaactgaaa ggtcactcca cagtatggat gaatcaccac   21540
attagcatgg tgagcgaaaa aagccagatg caaacgagta cacattgtat gatttcattt   21600
atatgaaact ctgaaaaatg caaactaact tatagtgaca gaaagcagat caggggttgc   21660
gtgggacagg gtgggcgggg cattcactgc aaagagcctg aggaacctat ttgagaagat   21720
```

```
ggaaatgttt tacatctgac attgatacta gttacatggg tgtatgcatt tgtcaatgtt    21780
catcgaactg gacacttaaa atgggtgtat tttcctgcat gtaaattata cctcaatgaa    21840
gctgatcttt tcaagggggt ggggaaggta taccagactc cagagctctg caacccttcc    21900
tatattattt gagtgtctga tttcaagctc atttgtgggc agagactgta atagattcat    21960
ctttaggtcc tcccctcact tcccagcctg agggcctagc aaaattcttt tttttgtttt    22020 tttttttga gatggactct gactatgttg cccaggttgg agtgtggcag cacaatgttg    22080
gctcactgca acctctgcct cccgggttca agagattctc ttgcctcagc ctcccaagta    22140
gctgggatta caggcgactg ccaccacatc tggctaattt ttgtattttt agtaaagacg    22200
gggtttcacc atgttggcca ggctggtctt gaactcctga cctcaggtga tctgcccgcc    22260
ttggcctccc aaagtgttgg gatgacaggc gtgagccatc gcgcccaacc aaaattctta    22320
aacccaatag ttcagattag caaatatacc ctgggcacct tctctgtgct gggtgctgcg    22380
gtcacagacc aatcagtcta gtggggaaca cagacggaaa aggccaaata gacacagtac    22440
agtgggtaaa tgtgctgatg gagtaaacag ttcattactg gccacagca atgaatcctg    22500 catagagtct ggaacttggg atgtgaagat ctcaaactgc aattcatcac ctgcattcaa    22560
atctccactc taccgcttgc tgtatgactt tgggtgacca ttttagcatg ccaaacctca    22620
gtttccacct ctggaaaatg gagatcatag tagctccaat ctagaggggt gttatgagaa    22680
ttaaaggaga cagcaataaa atgtttagca tggcaggcat agtaagtact tcataattgt    22740
tagtcatttt tatcatgaat gaagagcagg gaggtgggga gaggcacacg gggtgtgtgt    22800
atgtgtagtg gggtttcact acccaacctg aggtgagaga ggactgagag gtgctttccc    22860
agagaggtga tgcttggagg aggaattggc tagtttaagt ggccatgggg gcaggaggga    22920
gtgggaacag cttggaacaa acgctcaata aatatttgct caataaataa aaaaacagag    22980
actgtgcaaa acctgcctgt aaccaagggg acagagaggg cccgccagag gagactgggg    23040
ggtcctcagg aggcggggggc tgggtggctg gccccacag gcaggctcca gaccttccta    23100
gcctggtccg accccaccct gtgccctgcc cagttcccct gataggtttg gacagcccca    23160
gacctgaggc ctggagccca cgggaggagg aacggtgggg agggctggcg ggacggggt    23220 gctcacaggc cttctccctc taatgagaaa cggccaagtc cccgcaaggc gcctcccgcg    23280
cccccgttgt ccgagccaca aaggaccagg atcaatggaa ggcgggagcg accgagggc    23340 ctcctctttg tgcggctgtc tcaggcctgt ttgcgccgcc gtctccgcgc ccccattgat    23400
caggcatgtg gaaagattcc gcctcccggg ctccctttgt ggccgcgttg ccaggctgcg    23460
cccggagtga ctgcaccgcg cagggtgtac ccgcctgcgg tgggcaccgg gctgcgagac    23520
ggggtgggat cccaggaggg cagggtggcc agatttagca aataaaaata caggacttcc    23580
agttaaatgt gaatttctga taaataacaa aagcagacaa aaaacaaagt ataagtatgt    23640
cccaaatatt gcatgggaca tacttacact caaaaagtat tggttgatta tctgaaattt    23700
caacttaact aggcgtcctg tattttgtct ggcacccttt gaagggggaag ctgaatacat    23760 ctgcattgcc tagcacttat attacccccca acttcagtgg ttgaagtttt gtttgtttgc    23820
ttgctttttg tttttttattt ttattttttg gccatatctg cacacccga actgctattt    23880 agatagaatt tttctttaaa taatttatt ttttaaaaat cttaacctgg ccgagctccg    23940
tggctcaagc ctgtaatccc agcactttgg gaggctgagg gggggaggat cacttgaagc    24000
caggagttca agatcagctt gagcaacaaa gtgagatccc atctctacaa aacaaaacaa    24060
aaaactccct taacctatta accgtgattt attgatgcat agtgcaaata cattaacttg    24120
```

```
aacaaatatg aaatgtacct gttgatgcat ttttgcctac aagaacactc atgtgaccgc    24180
acccacatca agatatagaa tattcccggc cagcagtggt ggctgacgcc tgtaatctca    24240
gcactttggg aggccgaggt gggcgaatca cttgaagtca ggagttcgag accagcctgg    24300
ccaacaaggt gaaatcccct ctctactaaa aatacaaaaa ttagccaggg gtggtggtgc    24360
acgcctgtaa ttccagctac tcaggaggct gaggcaggag aattacttga acccgagaag    24420
cggaggttgc agtgaaccga agtggtgcca ctgcactctg gcctgggcga cagagcgaga    24480
ctccatctca aaaaaaaaaa aaaaagata tagaatattc ccatcacccc agaaggttcc    24540
ctggcgtccc tgagcagttg agcagtatcc acctccccat tggcagccat agatttgctt    24600
tagctattct tgaacttcgt atcagtggaa tcgtatagta taatgtgtac actcaagtct    24660
agcttctttc gctcagtatt atgtttgtga ggatgggcat ggtggctcac gcctgtaatc    24720
ccagcacttt gagaggccca ggtgggtgga tcagtatcac ctgaggtcag gagttcgaga    24780
ccagctggcc aacacagcga aaccccatct ctacaaaaat gcaaaaatta gctgggcatg    24840
gtggcaggtg actgtaatcc cagctacttg ggaggctgag ataggagaat cacttgaatc    24900
cgggaggcgg aggttgcagt gagccaaaat tgcaccactg cactccagcc tgggctacag    24960
agtgagattt catttcaaaa aaacaaaaaa caaaacaaac aaacaaaaaa agtctgtgac    25020
atttgtcccc attgtagatt gaccagttgt ttgttccctt tcgctgctgg ctgagtattc    25080
cattatatgg ctgttccacg gtttgttcct ctattttctt gttgatgggt gtcttgattg    25140
tttccagttt ttgctattat gaataaagcc gctatgacca tacttgcact ggtcactgta    25200
tgaacttaaa tatatttaac ctaagcaata ctatttgtga actcacaggc ttaaaatgct    25260
actttaattt tttttctcct gcacattaaa tatataacga tgcacatgt ttctgggaac    25320 atctttgtat tgaccaagct cactgtgaat ggtcacatat caaactgcag aatagacgtt    25380
aagagaacag actggcttgg ggtaggtctc gagcaagtgc gtcagtccct ctgggcctcg    25440
gtttcttcat ctgtgcaatg gggggtgata atgttaatta tctcacagag tggttgaaaa    25500
ggcaaaatgg gccgggcacg gtggctcaca cctgtaatcc cagcacttt ggaggctgag    25560 gtgggtggat catgaggtca ggagttcaag actagcctgg ccaagatgac aaaaccctgt    25620
ctctgctcaa accacaaaaa ttagccaggc acggtggcag gcaccttaat cccagctact    25680
tgggaggctg aggcaggaga attgcttgaa cccgggcagc agaggttgca gtgagccgag    25740
atggtgccac tgcactccag cctgggcaag aaagtgagac tgtctcaaaa aagaaagaaa    25800
ggaaagaagg aggaaggaag aaaggaagga aggcaggcag gcaggcggc aggcaaggca    25860 aaatggggta acaccttata aaagggccag ccatggtggc acacaggaga gttgcttgag    25920
cccaggagtt caagatcagc ctgggcaaca tagtgagacc ccgtctcaaa aaaaaaaaa    25980 aaaaggatac agcatagggc tgacacatag tgggtgctct acacagggag ctattatcca    26040
gtgctggatg ggcagtagca attgaactgg ctatgttaga tgcctgttct cattctattc    26100
tcatttcaac cctttgaggt agctactgtt attatcaacc tattttacag attaggaaac    26160
tgaggctctg agaggcagtc acttgcccaa aatggtatag ttagtaagcg gcaaaggcac    26220
cacctagtgt gttttccaga gcccaagggg gcaggaggga ccaatgaggc tctcatgcct    26280
ggagatgaga atgggttata caggaggagg agctgggtac cttctccttc ctgcctctgc    26340
atccccaatt agcgcccagc ttgaaggcaa gcaggtttct ctttggaggg tgggaggagc    26400
tggcctggac atttctagga gacgccaagc cttccagcca acgggcaggt gggaggacag    26460
gcagggcaag tctgacgggg taaggagggg aacagaggaa gccggaagct ggaggaaaag    26520
```

```
cctggcctcc tgtagccaca gccgctgggc agagcccggc ctcgctacct gccatctgaa   26580
gggcacggga actgctgatc tcaggcgatt agcataacaa tccccgatcc ggcgtcctcg   26640
ggtcccaaag ctgggtctgc acaatcccat ttcaagccag ctctttcttt agctggttaa   26700
ttagggaggg cacagactac ttaaagggcc ctgtacacac ggccttggct gcagctggga   26760
gcaggagagg gcccgacaat accttcagtc ctggcaggtg tgggtgctgc catagtgctt   26820
cacggcaggc cacggcgaaa aggctgctct caccggggat ttcaccgggc ctcctgttgc   26880
caccctccaa agccccatta gtgcacatct aggatagata tggcctgttc acagctcatg   26940
ccagggctcg gcacagaata ggtgctcaaa tataacttct aaaataagta actgggccag   27000
gcgcagtggc tcatgcctgt aatcctagca ctttgggagg ccaaggcagg aggatcactt   27060
gagtttcaga ccagcctggc caacatggca aaaccttgtc tctactaaca atacaaaaat   27120
gagctgggcg tggtggcaca cgcctgtaat cccagcaact caggaggctg aggcatgaga   27180
atcgcttgaa ctcgggaggt ggaggttgca gtgagccaag attgccccac cgcattccat   27240
cccgggcaac agagcaagac tctgtctcaa acataaaaa taaaataaaa taaattatcc   27300
aggtgtggtg gtgcgtgcct gtggtcccag ctacttggga ggttgaggtg ggaagatcgc   27360
ttgagcctgg gaggctgagg cttcagtaag ctgcgatcct gccaccgcat tccaccctgg   27420
gtgacagagc aaaaacttgt cacgaaaata aataaaataa gataactcac tgaagcatgg   27480
agcccatagt ccagaactca ggactctacc tactcatata atgagggccc aggctgaatg   27540
ctaatggagg gtacagggc agccccagcc ttgcaggtcc ctcagggtcc taagcccttc   27600
cttccccttc ccacagcctc cttgcactgg aagtccaaga gggcacttgg atcagagtag   27660
gcagaacata gtctttggga tgagatagag ggtagagctg ggttcgaatc ctggctctgc   27720
tgcttactag ctgtgtgatc cagaggaagt ctcttaacct ctctgaggct gttttctctt   27780
ctgtaaatgg ggatgatcaa aacctgcttc aaaagttgtt tacaggtatt tcttaaaata   27840
tcatatgaga gcgtctgcca cagagttggg gctcagggaa tgggagtcct tcctcttctg   27900
tagaaatacc cactgccttt ctaccgcgt ggctaatgtt ccccaggtcc ccatcatgca   27960
cccgctcagt gcttgttctc tctgccatcc tgtcaatgcc cttgtgaggt aagttctgtg   28020
cttctttttt tttttttga gatggagtct cactctgtcg cccaggctgg agtgcagcgg   28080
tgcgatctcg gctcactgca agctccacct cccgggttca tgccattctc ctgcctcagc   28140
ctcccaagta gctgggacta caggcacctg ccatcacaca cagctaattt tttgtatttt   28200
tttagtagag acagcatttc actgtgttag ccaggatggt cttgatctcc tgacctcgtg   28260
atccacccgc ctcggcttcc caaagtgctg ggattacggg gtgagccacc gctccctgcc   28320
agttctgtgc tttttaaaga aaaggggccc ggtggtgcag tggctcatgc ctataatccc   28380 agcactttt tgtttgtttg tttgtttgtt tgtttgaggc agagtcttgt tctgtcgccc   28440
aggctggagt gcagtggcac aatctcggct cactgcaacc tctgcctccc gggttcaagt   28500
gattctccta tctcagcctc ccaagtagct gggattacag gcacctgcca ccacgcccag   28560 ctaattttg taatttgta gagatggggt ttcgccacgt tggccagact ggtcttgaac   28620
tcctgacctc aggtcatctg cccacctcgg cctcccaaag tgctgggatt acaggtgtga   28680
gtcactgcgc ctggccaata atcctagcac ttggaagac ctaggcagga ggatcacttg   28740
aggccaggag tttgagatca gcctgagcaa tgtagcaaga ccctgtttct tcaacaaaat   28800
tatatattca aaatgttaag gctgagcgtg tggcttgcg gctctaatac caacactttg   28860
ggaggctgag gtgggaggat ggcttaagcc caggagtgca agatcagcct gggcaacatg   28920
```

```
gtgagacatc atctctacaa acaaaatttt ttaaaataaa aataatgat ttttaggcca   28980
gatttggtgg ctcatgactg taatcacaga actttgggag ggcaaggcaa gctgatctct   29040
tgaggtcagg agttcaagac cagcctggcc aacatggtga aacccatct ctactaaaaa   29100
tattaaaaaa ttagagccag gcacagtggc tcacacctgt aaccccagaa ctttgggagg   29160
ccgaggcggg ccgatcacaa ggtcaggaga tcgagaccat cctggtcaac atggtgaaac   29220
cccgtctcta ctaaaaatac aaaaattagc tgggcgtggt ggcacatgcc tgtaatccta   29280
gctactcggg aggctgaggc aggagaatcg cttgaaccgg gaagtcagaa gttgcagtga   29340
gccaagatcg tgccactgca ctccagcctg gcgacagagc gagactctgt ttaaaaaaaa   29400
aaaaggccgg gcgcagtgac tcacacctgc ctgtaatccc agcactttgg gaggctgagg   29460
caggcagatc acctgaggta aggagttcga gaccagcctg accaacatgg agaaacccca   29520
tctctactaa acatacaaaa aaaaaaatta gccaagcgtg gtggtgcatg cctgtaatcc   29580
cagctgctca ggaggctgag gcaggagcat cactggaacc caggaggcag aggttgccgt   29640
gagccaagat cacaccattg ccctctagct ggggcaacaa tagcgaaatg ccatctcaaa   29700
aaaaaaaaaa ttagttaggt gtgatgacac acgcctgtaa tcccagctag ttgggaggct   29760
gaggcaggag aatctcttga acctgggaag cccactgcac tcagagtgaa tgagactggg   29820
ccacagagtg aatgagactc tgtctcaaaa taaataaata aataaatata ataataattt   29880
tttaaaaagg aaaatgaagt cagagacaaa gtgacttgcc caaggccaca cggctagaaa   29940
gtttcaaagg gaggcttgag ctcagctaac cctaagaaca atggctctgg agccaggaaa   30000
ggatgggcat tattgcagcc actgctccct ttccactcag ccagccagat agtctcaggt   30060
atcttttgat cttctgctgt gtgttaagca ttgtgctgag ggcaggggat agagctgagc   30120
acaatcgcca ttttccatca atgtctgtga gtgttaaggg cttgaggaca gtaaaacagg   30180
gtgataggct agaggcctgg gggtctagga agacttcttc tgtataggtg atacttgaac   30240
tgcaggattg ccatgggaag aggggggcag gtaagtggga agcattccag gtaggcggga   30300
gagcaggtgc aaaggtcctg aggtaggact tagtttgggg tatctcagga actgaaaggc   30360
agccagtgtg gctggagcac tgggagggag agtgagagtg ggatgggcca ggctggagag   30420
ggaggaaggg ccttaaggga catcctaaga actccttcct tcccttcctc cctcttcctt   30480
tccttcttct ctccctccct tccttccttc ccttcctcct cctccttcct ttcttccctc   30540
cctcccttcc tgccttcctt ctcttttttc ttcccttcct tcctttcctt ctccttccct   30600
cccatccttt ttttcttact tcctccctca atctctctct ctcttcctac tttccttccc   30660
tccttccttc cttctcttgt tccttcctcc cccctctcct ttccttcctt ccctccttct   30720
tccctcttcc ctcccttttcc ttctctcctt cctctgtcct tttttttttt tttttttttt   30780
gagacagagt ctcagccagg catagtggct cacgcctgta ctcccagtac ttggggaggc   30840
cgaggcaagt ggatcacctg agatgaggtc aggagagttt gagaccaacc tggccaacat   30900
ggtgaaaccc tgtctctagt aaaaatacaa aaattagctg gtgtggtgg tgggtgcctg   30960
taatcccacc tacttgggag actgaagcag gagaatcact tgaacctggg aggcagcagt   31020
tgcagtgagc caagatcatg ccactgcact ccagcctggg cgacagagcg agactccgcc   31080
tcaaaaaaaa aaaaaaaaaa aaaaagaga cagagtcttg ttctggcacc atctcagctc   31140
actctaacct ctgcctcccg ggttcaagca attctcctgc ctcagtctcc taagtagctg   31200
ggattacaag cacctaccac cacatctggc taattttgt gttttagta gagacggggt   31260
ttcaccatgt tggccaggct ggtctcgaac tcctgacctc aagtgatctg cccacctcag   31320
```

```
cctcccaaag tgctgggatt acaggtgtga gccaccgcgc caggctcctt ccttccttcc   31380
ttctttcctt cctcttttc ttcctcccctt ccctcccctcc gttcctcccct tccttctttt   31440 ctctctctcc ttcctttctt ccttccccccc ttcctccccct ttttccctgc cttcctacct   31500
tccttccttc tttctctcct tccttcctcc cctcctccct ctcttccttc cttcctcctc   31560
tccttccctc cctccctcct tcctctctcc cttccttcct cctctccttc cctccctccc   31620
tccttcctct ctcccttcct accttccttc cttccctccc ctccttcctt cctccccctcc   31680 ttcctctctt ccttccttcc ctccgtcctt ccttctttcc ctccgtccat gctactgtt   31740 tctcaagcac tggcccaggg ggctgcaggc ctctgagtct ctctgtgctt ctctccctct   31800
tcccttctcc cttcctctcc cctcccccctc ctcttctaac agccgcccca cccccactgg   31860
tccagctctt cccctcccct ctaccccatc ccctcccctc cacgccaccc cctcccactg   31920
acaatgggga ggaaccctgg gctcagctcc ccacagtatt gtcccttaa ggaatcccta   31980 aatccggaca cccctctcct cccccacctg agaaccaatt agggttcccg aattcaagta   32040
gaggcttttg tgtgtcacgt gtttgtggaa caaagccctc tccggcagga ataaaagctt   32100
ctattcagga gccagtttgc tctcattcta atcgtttcca ctccagcctc gcctccttcc   32160
cgggttccca gggccgccca gctcggcctc accttcccgc ttcagcaccc tgtattagtg   32220
ccctacccaa aagcaggtgg ccaccgaccc agggctctgc ccacctttc ttcccgaaag   32280 atcacgtgat gccgactggc tccgagctgg gccctgggct cagcgctgtg tgagcatcat   32340
tgtacgggac tgtgaatagc ctcaatgcaa cggaggaaac tgaggctcag agaggttagg   32400
gcacttgcct gaggtcatac ggctggtaag acagggagtc tacaccctcg ggcattattc   32460
tatggtaccc ccagctggcc ctagcatagc acagggtgca gaagaaggga gctgccattt   32520
ttataaagcc catggggcca ggcacctgct ggatattaga gactcctgac aatgccacgt   32580
gaaggagcaa cgattgaggt caaagtcact gacaagtccg aggcaggatg gcgttgggac   32640
tcagaacttg gagggaaaca gtggggccct caggtctgaa gatgaagaga cagggagtat   32700
gggaagccca tattacgaag ccattaagaa aactgtattg atatggaatg gtaattgaca   32760
cattgccaag agaaaaaggc agtacattga atggaatatg atctcatttg cataagagga   32820
aaaggaaata tctacacaca aacatgtata cacatatcgc acatttctat ctgtatggaa   32880
taaatttggg gaaaaaacat cataaattgt agtatccttt atttcctttg aagagtggaa   32940
atagagcatg gagagaagtc acttagtacc attctgtgct gtttgaaaaa agatatttc   33000 ttactatgat catgtattta ttttatgata attattttg ttcattgaa gttaactatt   33060 ttaaagcttg catttcagtt gcatttagta tatttacaac gttttcatca ccctaaaggc   33120
aaacttctaa catcatatcc agtaagcaat tacttctcct tccttattcc ccccgcccct   33180
ggcaatcact aacctgcttt ctgtctctac agatttacct attttagata tttcatagaa   33240
atggaattat agcatttcat agaaatggaa tcagtatgtg accttttca tctggcttttt   33300 ttcttttcct tctttttttt tttttttttt agatgagctc tcactctgtc acccaggttg   33360
gagtgcagtg gcgcgatctc agctcactgc aacctccacc tcccgggctc aagcgatcct   33420
cctgcctcag cctcccaagt agctgagacc acaggtgtcc gccaccacac ccaactaatt   33480 ttttttgtatt tttgatagag atagggtttc tccatgttgt ccaggctgat ctcaaactac   33540
tggattcaag cgatctatct ggcttggcct cccaaagtgc tgggattaag gccggcaaaa   33600
tgcacccctg agctcagcct ggttttttc atttaggatg atgtcccctca ggtttatcca   33660 tgttgtagca tgtgtcctat ttcattcctt ttaacggcta aatagtattc ccttgcatgg   33720
```

```
gtatactaca tcttgtttac ccattcatca cttgatggac atttgggttg tttcaatctt   33780
ttggcagtcg tgaatggtgc tgctatgatc atgcatgttt ttgtctgaat acctgttttt   33840
aattattttg ggtatatgcc taggatctgg gtcatatgat aattctgttt tacttttga   33900
gataccatcg aacggttttc cacagtgcca caccatttta cgctcacacc agcaacgtac   33960
agaaagctcc aatttctcca cattcttgcc aacacttgtc attttccatt tatttattta   34020
ttcatagctg tggtagtagg tgtggaatga tatctcattg tggctttgcc ttgcatttca   34080
ctaatggctc aagatgaata tcttttcacg agcttattgg ctatttatgt attttctttg   34140
aagaaatatc tattccaagtc ctttgcctat ttgtacttat ttattaattt attttttgag   34200
aaagagtcgc actttattgc ccaggctgga gtatagtggc ttgatcacag ctcactgtag   34260
cctcgacctc cctgggctca gtcctcctg cctcagcctc ccaagtagct gggactacag   34320
gcacacgcca ccatgcctgg ctaattttg tatttttttt ttttttgta gagatagggt   34380
ttcaccatgt tggccaggct gttctcaaac tcctgacctc aagtgatccg cccacctcag   34440
cctcccaaag tgctgagatt acaggtgtta caggtgtcag ccactgcacc agccctttt   34500
cactttttt tttttttttt ttgagacagt ctcgctctgt tgcccagact ggagtgcagt   34560
ggcacaatct tagctcacag caacctccac ttcccaggtt ccagcgattc tcccacctca   34620
gcctcccgag tagctgggac tacaggcgcc caccaccact ctaagctaat ttttttgtatt   34680
tttaatagag atggggtttt accatgttgg ccaggctggt ctcgaactcc tgacctcaag   34740
tgattcgcct gccttggcgt cccaaaatgt tgggattata ggcgtgagcc accacctg   34800
gcctcacttt cttgatagtg ccttttgatg cccaagtttt tattttatt tatctattca   34860
tttatttatt ttgagacagg gtctcgctct gtcacccatg ctggagtgca gtggcacaat   34920
catagctcac tacagcctcg aactcctgag ttcaagccat cctccagcct tagccttcca   34980
agtacctagg actccaggct cgtgccacca cccagctaaa ttttgttatt ttatgtagag   35040
acgaggtctt actatgttgc ccaggctggt ctcaaactcc tgagtttaag caaccctcct   35100
gcttagcctc acaaaatgct gggattacag gcatgagcca ctgcacccag ccaaaagttt   35160
taaatttaaa tgaagtccaa tatatctatt gttttcttgt gttgtttgtg catttggtga   35220
cataactaag aattgccaaa tttaaggtca taaagattta cccctgtgtt tcttttatcc   35280
attttgagtt cattttgttt ttacatggtg ccaggtccaa ctttattctt tcacatgtaa   35340
atatcctata ataattgttt ttaatctttg tctttgctgt cttaagaaat gatctccaaa   35400
tttttgtgat gatacatccc taagaggaaa caatctttga gctcatattt ctagcataca   35460
tacatttata tatttacaaa atatatacat actctactgt tataatatct atgttacaaa   35520
catctatgca aaagaaattt taaaagatg aaataggctg gcacagtgt ctcatgcctg   35580
taatcccagt actttgggag gctgaggtgg gtggatcact ggaggcgagg agttcaagcc   35640
cagcctggcc aatacggtga agcccagtct ctcctaaaaa tacaaaaatt aggccgggag   35700
cagtggcacg cacctgcaat ccaagcactt gggatgctg aggcaggcga atcacctgag   35760
gtcaggggatt cgagaccagc ctggccaaca tggcaaaacc ccatctctac taaaaataca   35820
aaaattagct gggcatggtg gcgtgtgcct gtaatcccag ctacttggga ggctggggca   35880
ggagaatctc ttgaacccag gaggcagagg ttgcagtgag ccgagattgc accactgccc   35940
tccaacctgg gccacagagt gagactccat ctcaaaaaaa aaaaaaaaaa aaaagctggg   36000
cgtggtggca catgcatata atcccagata ctcagtaggc tgaggcaaaa gaatcacttg   36060
agcctgggaa aaagagattg cattgcagtg agctaagatt gggccactgc actctagcct   36120
```

```
aggcgacaaa gtgagattct gtctaaataa ataaataaaa taagaaatta gccagatata   36180
gtggcacgca cctgttgtcc tagctactca ggaggctaaa gtgggaggaa ggcttgaacc   36240
caggagttca aggcttcggt gagttatgat tacatcactg ctgcactcca gcctgggcaa   36300
cagaggcaca ccctgtctta aaaaaaaaaa aaaaaaaaa agagcgggga aaagagatga   36360
aatagaaaaa aatactatag aaggcctgat cttttcttgg tggatgattt tgagtgctcc   36420
cagagacact cacccctctg gtgcttgctg gtgctgctga tgacagagtg aggtcagccc   36480
accctctaaa ggcacagctg ggacagctgc aggcaggcat gggagtgggc tctccaggtt   36540
gggtctgact tccctcttct gagtcacaaa atttcacatc agaaggacgg gtgtttgaat   36600
cctggttcca tctatttcct agttgtgtgt cactatatta agctgtattt ggccgcgtgt   36660
ggtggctcac acctataatt gcagcacttt gggaggctga gcaggtgga tcacctgagg    36720 ttagtagttc gagaccagcc tggccaacat gatgaaatcc cgtctgtact aaaaatacaa   36780
aaattagcca gatgtgctag caggggccta caatcccaga tacttgggag gctgagacag   36840
gagaatcgct tgaacctgga aggtggaggt tgcagtgagc caagatcaca ccactgcact   36900
ccagcctagg caacaaagtg agacaccgtc tcaaaataaa agccatatag ctatattaaa   36960
aagcaaagtc ttaacagcct ttttttttt tttagacagg gtattcttct ggtatccagg    37020
ctggaatgca gtggcacgat catagctcac cgcacccttg atctcccggg cccaagcgat   37080
cctcccacct caggtttccg ggtagctggg cctacaggca agtgccacca tgcctggcta   37140 attttttaaat ttttgtagag acagagtctc cctttgttgc tcaggctggt ctcgaactcc   37200
tggccttaag caatcctccc acctcggcct tccagagtgt tgggtttata ggtgtgagcc   37260
ttacacttag ccttttttt ttttttttt tttgagacgg agtttcactc ttgtccctca    37320
ggctggagtg caatggtgca atctctgctc actgcaacct ctgcctccca ggttcaagca   37380
atcctcctgc ttcagcctcc tgaacagctg agattacaag catccgcccc catgccaggc   37440
taattttttt ttttcccatg acagaatctt gctctgtcgc ccagaactgg agtacaatgg   37500
ctcgatcttg gctcactgca acctccacct cccaggttca agcaattctc ctgactcagc   37560
ctcccgagta gctgggatta caggcgcatg ccacctcgcc cggctaattt ttgtattttt   37620
agtagagaca ggatttcacc atattggcca ggctggtctc gaactcctga cctcgtgatc   37680
tgcccgcctc agcctcccaa agtgttggga ttacaggcgt gagccaccac gcccagctgg   37740
ttattatttc ttaaggctta aaggggccaa tgtgtcttcc ccacaattta cctatttgtt   37800
cattcagcca agatgtaaag aatgcctgct atgtgccagc cataatgggg aacaagaaga   37860
aagcagtcct tattatttat ttatttattt atttatttat ttattatttt atttatttt   37920 agaggtgaga gtcttgttat gttgcctagg tgtttgtaac ggtgcctggc taacagtcct   37980
ttcttttgag aagcatatga cctcgggata cacagacatt acaatataca cacacaaata   38040
cacattgtct gtatttatgc agtggagcaa tcataactca ctacagcctc taccttctgg   38100
actcaaggga tcctcccact tcagcctccc aagtggctgg gagccaccat actcaaggca   38160
tgagccacca tactctgcta atctttattt tttagtagag gtggggttct cagtcttttg   38220
cttaggctgc tctgtcttga actcctgacc tcaagtggtc ctcctatctt gggctcctgt   38280
ctagctagga ttacagggac atgcacacca ctctcagcta attttatctc tgcatttctg   38340
atgaatgagt tttttttt tttttttt ttttttttt agatggtatt tcactctgtc       38400
gcccaggctg gagtgcggtg gtgcaatctc agctcactgc aacctctgcc tcccagtttc   38460
aactgattct tgtggctcag cctcccgagc agctgagcag ctgggattac aggcatgtgc   38520
```

```
caccatgccc agtaattttg tatttctagt agagatgagg ttagccaggc tggtctcgaa  38580
ctcctgacct caggtgatcc gcccaccttg gcctcccgaa gtgctgagat tgcaggcgtg  38640
agccacctag cctggccaaa tgagtttttt aatttaattt tttttctgcc cccgaaacca  38700
ccctgaatga gttctattct gcatcagtta accaataatt taatgttgac tcaacatcat  38760
ggtggacact agaggcaata gttgggccgg tggtaaatac acagttcagc caacacaagt  38820
acccactggc tctcctttga ggagtgccca cttctctgtt tctgcttttc cgacccagct  38880
tagatgccag ccttcccttt cctctccaac ccactgtact ccctccctcc cttgagcttc  38940
caaagctctc ttaaggctct catactttgc tttgggatat aatttgtccc tttactggag  39000
cgtaaatgcc tcaagaactg tcagcaagcc ttattcaggt gtggatacct ccagagtacc  39060
tgacacggtg gaaaaggcac atttgattca ttcactgaga agagaagagg caaagatgta  39120
gccgctgagt actagctgtg tgaccttggg aaaaataatt cttctttttgg atctctaagt  39180
ttatccataa agcaagaggg gggcatcaga ggctctccaa ggcagccttt ctcaaccttt  39240
ttaaaattgg gacactcctg atgaatggca ttcccacgtg actcatgctt ccatggtgtt  39300
cagataagat agtctgaatt ctgcgtaacc ccagctcttc ctctctccct ctggagagct  39360
tgtccaaagg ccagggagca agagtgacgt tatttataga cataaccttg actccacttc  39420
tcctcatttg tttatttctt tttcttcttc atttatttat ttaaggcaaa gaaagcattc  39480
tcaagcttca gtagaggtag tggttaaaaa taccagacca gaaccagag acacttgcct  39540
ttgaatcccc tctttgccat ttctgagtgt agtatccttg ggtaagtttg ctgagcctca  39600
gtttccccat ctacaacatg ggaggatcat catagaacta actttagaag actgtagagg  39660
ggattaaatg cgatcagaca ggaaagctct tagcaccatg ctgtacatgg taagggctca  39720
gtaaagttgt caatatctac tttgttgtta ttagttacat gttacatgtg acacactaaa  39780
aaattgggat atgatgctga gaccaaaaag taaactcttg attagcttct gccaaatttg  39840
atcttttgtg attttctcac ccagtcttgg ggacgctgag ccgtggtgaa tttctctgct  39900
ggtggaaata gattcacgga tgtagctcaa tcctttctta ttttgtttta ttttattttt  39960
gagatacagt ctcactctgt tgcccaggct ggagtgcagt ggcgcgatct cggctcactg  40020
caagctccgc ctcccgggtt cacgccattc tcctgcctca gccttctgag tagctggaac  40080
tacaagcgcc cgccaccatg ctaattttt gtatttttag tagagacggg gtttcactgt  40140
gttagccagg atggtctcga tctcctgagc tagtgatcca cctgccttgg cctcccaaag  40200
tgctgggatt acaggtgtga gccaccgcac ccggccagat gtagctcaat ccttctttac  40260
ctttgttact ctatctccac tcgctcatcc tattcccctt ttaattttt ctgttttttt  40320
ttttttgtaa agtatcactc tcactctcac ttcttttttt ctttttttgac agggtcttgt  40380
tctgtcaccc aggctggaat gcagtggcac aatcatggtt cactgtttcc tcaaactccc  40440
gggctaaaga gatcctcctg ccttagcctc tcaagtagct gggactacag gctcatacca  40500
acatatctgg ctaattttct tatatttttg tagaggtggg gttttgttat gttgcccagg  40560
ctggtcttga actcctggcc tcaagtgatc ctcccacctt ggcctcacaa agtgctggga  40620
ttagaggtgt cagccactat gctcggcttg atgaatttc aaaaattgta ggttgaggcc  40680
gggcacagtg actcatgcct gtaatcctag cactttagga ggtggtggag ggcagatcac  40740
ttgagcctag gagtttgaga ccagcctgga caacatggca aaacccatc tctatgaaaa  40800
atacaaaaat tagccgggga tggtggtgca tgcctgtagt cccagctact caggaggctg  40860
aggcaggagg atcgcttgaa cttgcttgag gtcaaggctg ctgtgagccg agatcatgcc  40920
```

```
actgcactcc agcctgtgtg acaaagtgag accttgtttc aaaacaacaa caacaacaac    40980
aacaaactgt atgagcaaaa gaagccagat gcaaaaaaat acatacaaaa attccattta    41040
tatgaaatta tggaacaggc aaaactaatc tatgggaaga caggtcatag tcgcatttat    41100
ctttgggaag cagatattga cttggaagca ggagataact ttctggagga aggaaagctt    41160
caatatcagt gctgcccaat agaaataaaa tgccagctac actcacgcct gtaatcccag    41220
cactttggga ggccaaggca ggcggatcac gaggtcagga gattgagacc atcctgacta    41280
acactgtgaa accccatctc tactaaaaat gcaaaaaatt ggccgggcgt ggtggcgggc    41340
gcctgtggtc ccagctactt gggaggctga ggcaggagaa tggcatgaac ccaggaggcg    41400
gagcttgcag tgagacaaga tcgtgccact gcactccagc ttgggcaaca gagcaagact    41460
ccgtctcaaa aaaaaaaaa aaagccagct acagctgtaa accatatatg taatttaaaa    41520
attttctagg aaccacatta aaaagacata aaggccgggc gcggtggctc actcctgtaa    41580
tcccagcact ttgggaggcc gaggcaagtg gatcacctga ggtcaggagt tggagaccag    41640
cctggccaac agggtgaaac catgtctcta ctaaaaatac aaaaattagc tgggtgtggt    41700
ggtgggtgct tgtaatcgca gctactcggg aggctgaggc agaagaatca tttgaacgaa    41760
ggaggtggag gttgcaatga gccaagattg cgccactgca ctccagcctg ggtgaaagag    41820
taagactcca tctcaaaaaa ataaaaataa ataaataaat aaataaaaat aaaaagacat    41880
aaaatgaaac aggtgaaatt tattttaata atatattcaa aaattacgtt tcaacatgta    41940
atcaatgtaa aattattatc actgtatttt acattcattt tctgcattct ttgatatcca    42000
atgtatattt tgcacttaca gcactggtta gtttgggcca gctgcatctc aagtgctcag    42060
tagccacacg tggtgagtgg tcacttttat ggatctgtat cttaatctgg gttttagcta    42120
tatataaaaa tttatatata aaacttggga ggcactccag cctgggtgac agagcaagac    42180
tttgtttcaa aaaaaaaga aagaaagaaa ttcatttgta ttgttatatg tatctgtcat    42240
ttgtgtgttt tttttttttt tttttgagat ggagttttgt tctgttgccc aggctggagt    42300
gcagtggcac gatctcgatc ttggcttact ccaatctctg cttcctggat tcaggcaatt    42360
ctcctgcctc agcctcccca gtagctggga ccacaggctc acaccaccac acctggctaa    42420
tttttgtatt tttagtagag acagtctcac gatgttggcc aggctggtct tgaactcctg    42480
gcctcaagca atctgaccac ctcagcctcc caaagtgctg ggattacaag cgtgagccac    42540
caagcatggt cttttttctt ttttctttt tttttttctt tttttttgag atggaatctc    42600
tgtcacccag gctggagtgc agttgcgtga tcttggagtg atcttggcac actgcaacct    42660
ccacctcccg ggttcaagtg attctcctgt ctcagcctcc caagtagctg ggattacagg    42720
cctgtgccac tacacccagc taattttgt attttagta aagatggggt ttcaccatgt    42780
tggcaaggct ggtcctgaac tcctggcctc aagtgatcca cccgccttgg cctcccaaag    42840
tgttgggcgc ccggccttt tcattttaca tagtattcca ttgtacgaat atcatagt     42900 ttatccattc tcctgttgat ggacgtttgg attacttcca atttctgctt attatgaata    42960
atgctgctat cagtgttctt gaacagtctt taaatagact catttaaatt attttactg    43020 ttttctggtt gttaagataa atccatactc acagaaaaaa ttcatactca tactaacaca    43080
cacgcctccc caccagttaa cagtttttt actgttttct ggttgttaag ataaatctat    43140
actcacagaa aaaattcata ctcatactaa cacacacgcc tccccaccac attaatggtt    43200
tgatgcaaat ggcttatggt ttgatgtaaa ttcttttcct ccacatatag aatcatgtat    43260
tatcattatt aataaaattg tcactttgat ggttcctccc ttggttgtct gactcctggg    43320
```

```
ggtgctgcgt agctcttaat ccttgccctt cttgttgtaa ggtctctaga agaccaaaac   43380
tggaaaggat gtagtgatca tctagtccag agaaggcaac gctatagcac accttctact   43440
gttccatgac tacctgcacc aaggcagaca tcactaatca atcacccgat ttctatcctt   43500
gcccagccct agccactacc agtcattttg gaggtaattt gagaggccaa gtagaaaaac   43560
tgaaaccaat tttccatctc tggaataata tgccactttc cattttgcac atgaataaac   43620
tagcgctcag agaggggaag agcctgtttc aaggtcagag gtggagcccc aggctcctaa   43680
ctccctaata cttttttccac taagttcaca aactccaaaa actatttccc tggtccctga   43740
aaacctgggc tctagggagg gtgctttgtt ctccagatgg ggctcagaga tgagaacctc   43800
ccctctagcc agcccttcac ctttaggtct ggcctaagtg taagagaagc cctgcctgc   43860 agcctggcac cccttttccca ccgtcagcac tgacagacct gcggtttcac ttctccaggt   43920
ccacagtttc agtttcccaa aataaacatt aaaaacaata aaacataaag gaggcatcct   43980
cttaacatct ttgtctttgg cccctgaatt gtagaatgat tagttgagca gattaaatca   44040
cagagttaat tacagcagag aggtgacttc agatgctgaa accatagaac tctgaagcat   44100 ccccccttc accgacacat caaaccagcc ctggctgtca ttggaagcga cagtgagaaa   44160
gtgagaaagt gggagagtca gcaggtctgg acagactgtg ggtgttctca gctgggcaag   44220
cagaatagtt tatttaattc cctccctgcc agggcagtgg ggaaagtcgg ggggtgggga   44280
atggagacag agtgtagcat aatgtttggg tcaggtagag ctagattttt agactggcca   44340
gctgcatgac cttgggcatg tcacttcaga tgtttgagtt tcagcttcgt catctgtaag   44400
gcaagcacat taatagaacc tactacattt aattattgca gtgattcaaa tgacttggtt   44460
aaaaagatgt gtatcagcca ggcgtggtgg tgcatgcatg taatcccagc actctgggag   44520
gctgaggcgg gaatatcgct tgagctcagg agttcaagac cagcctaggc aaaaaagatg   44580
tatgtaaaac tactgtgtct ccagattgtc acatctgtga agtaggaat cactgtctgt   44640 ctcattcacc atctcatcct ccagccctag cacagtgatg gtttctaggc aagcacaact   44700
agtgaggccg ggcatggtga ctcatgcctg taatcccagc acctggggag gctgaggcag   44760
gcagatcact tgagctcagg aattcgagac cagcctgggc aacatagcaa aactctgtct   44820
ctataaaaaa tacaaaaact agctgagtgt ggtggcttga gcctgtagtc gcagctattt   44880 gggggggctga ggtgggagga tcctttgagc ccaggaggca gaggttgcag tgagccgaga   44940
tcatgccact gcattccagc ctgagtgaca gagtgagacc ctgtctcaaa acaaacaaa   45000 caaacaaaca aaaccaact attgagtact tagtgtaagg tatggtcctg aggataaggg   45060
gtggtggagg agaatgcaaa gaggtttaag ggacttccc ttagagagct cccattccag   45120
cataacagac attccagaac catctgtaat aataggtgca ttgtgtgtgc attaaatagg   45180
tagataacat aaaattatgt tcatgatgaa gtgcatgatg ggaattctgg tatcagactt   45240
gaattcaaat ctcagccccc tcacttacca cccgtcttat cttattagc aagttgacct   45300 ctcaatgctt tcatttcctg atctgtaaaa tagcgacctg cctcagagag ctgttgcaag   45360
gattgaatga gtttcccaac gcaaagtgcc tgagacacaa taattgctca gagtctgact   45420
ctgttgccca ggcgggagtg cagtggcagg atctcggctc gctgcagcct ctgcctcctg   45480
ggttcaagtg attctcccac ctcagcctcc ccagtagctg ggattacagg catgtgccac   45540
cacgcctggt caattttttgt attttttcgta gagacggggt tttgccatgt tggccaggct   45600
ggtctcaaac tcctaacctc aagtgatctg tccacctcag cctcccaaaa tgctaggatt   45660
acaggcgtga gtcagcacac ccggcacccc catagtgctt ttgatggact accttttactt   45720
```

```
tcccatagtg ctttagagtg tctaaggtgc tttcaaatac atgatctcac ttaagtcttg   45780
cagcaactcc gaaagtaaat ggaagctcag aaggctaagt ggtgtatccc tagaaccacc   45840
cgaccagaaa cagtggtagt cccaagacca gcatatggat ctttggactc tcagtcaagt   45900
gctttcatta ctccagctca tagccttctg gttgagtcca gaaatctgag agaaggaaaa   45960
aaaaagagag aaaaattagg acaaaaaagt gagggactga agacctatgt ccacacaaaa   46020
acctgagctt taatcataat tgccagaact tgaaggcaac caagatgtct ttcaggaggt   46080
gaagggatgc ataaaccgtg gtacatctag agcacagact attatgcagc actaaaaaca   46140
gacaagctat caagctatgg aaagacatag acggggtcag gcgaggtggc tcacacctgt   46200
aatcccagca ctttgagagg ctgaggcagg tggatcactt gaagctagga gttccagacc   46260
agcctgggca acatggtgca accctgtctc tacaaaaaat acaaaattta gccaggggcg   46320
gtggtgtgtg cctgtagtcc cagctattct gtagtcccag ctgttgggga ggctgaggtg   46380
ggaggattgc ttgagcctga gaggttgagg ctgcagtgag cctgaacatg ccactgcact   46440
ctagcctggg cgacagagtg aaaccttgtc tcaaacaaac aaacaaacaa acgaaacaaa   46500
cgagcaaaaa aacccaggaa acaaaaaaat aaaacccaca cacaaaaaaa gccaccatag   46560
aggaatctta actgtgtgtt actaagtgaa agaagccaat ctgaaacagc tactactgta   46620
tgattcaagc tatacgacgt tcttttttt ttgagacgaa gtcttgctct gttgcccagg   46680
ctggagcgca acggggcgat cttggctcac tgcaagctct gcctcctggg ttcacgccat   46740
tctcctgcct cagcctcccg agtagctgga actaaaagcg cccgctacca tgcccagcta   46800
attttttgta tttttagtag agacgggtt tcatcatgtt agccaggatg gctcgatct   46860 cctgacctcg tgatccgcct gcctcggcct cccaaagtac tgggattaca ggcgtgagcc   46920
accgcgtccg gcctatatga cattcttgaa aagagaaaac tatggagagt gaaagatcag   46980
gggttgtcag gggttggggg agggagaac aaataggtgg agcacagaga atgtttagga   47040
cagtgaaact actctgtatg acagtataat gggagataca tgtccttata catttgccca   47100
aacccataga atgtataaaa ccaagagtga actctaaact atggactctg ggtgataaca   47160
atgtgtcagt ataggttcac caattgtaac aaatgtacca ctctggtggg ggatgttgac   47220
agtgggaaag gttacacaca tgtgggtca ggcggtatgg ggaaatctct gtactttctc   47280
ctcaataaaa ataaagtcta cttttaggc tgggcatagt ggcttatatt tgtaatccca   47340
gcactttggg aggccgtggt ggcagaggat tgcttgagtg caggagcttg agaccagcct   47400
gggcaacata gttagacccc gttctgcaaa acaaaacgaa acaaaaatta gctgggcatg   47460
gtggcgtgca tgtgtagtcc cagctatttg ggaggctgca ttgggaagac tgcttgagcc   47520
caggaggttg aggctacagt gaaccctcat cgtgccaccg cgctccagcc tgggcaacag   47580
agtgagaccc tgcctcaaaa aaagaaagaa aaaataaagt atatatat aggtatatat   47640 atatattttt ttaagtgggg gaagtttgta aaatgggctg attataaatg catggctctt   47700
aatcagctta cagtaaattt tccttgtct tgcatggaca agaaatggga agttccaggt   47760
aattcagggc tttgcttgga tattgcattt tcttttgttc ttttttttc tgagacggag   47820 tctcattctg tcacccaggc tggagtgcag tggtgcaatc ttagctcact caacctccg   47880 tctcctgagt tcaagcaatt ctcctgcctc agtctccca gtagctggga ttacaggcgt   47940
gcgccaccac gccaggctaa ttttttgtatt tttagtagag accgggtttc accatgttgg   48000
ccaggtggtc tcgaactcct gacctcgtga tctacccacc tcggcctccc aaagtgctgg   48060
gattacaggc gtgaatcact gcgcccggcc aatattgcat tttcaaagaa tgagaacact   48120
```

```
gtgaaatact ctgcacgcta aaaccacatg gactataatt taatctttaa ttttgttgtt    48180
gtcattctca aaggctcttc aatatatctt aaagctgtgt ttctccaaga gtggccaagg    48240
aaaaccctca gctctcagcc ttctcatctg atagaggtgt ctgttcaaaa actgccattt    48300
tctgagcccc catccacccc tagtccactt gacctacagt tttagagtag tgaaagtcaa    48360
aatatgaacg ttaattatca ttgtacttaa gagatgcaga cattctgctt aaatgagagt    48420
tctgtatcat agagtagact catttacctc atctccttca agtctttgct aaaacgtctc    48480
cctccccatg agaatgttgt tgatttaaaa ttgcatctca ggccaggtgt ggtggctcac    48540
gcctgtaatc ccaacacttt caagggcaga ggtgggcaga tcacctgagg tcaggcgttc    48600
aagaccagcc tggccaacac ggcgaaaccc catctctact aaaaatacaa aaaattagtc    48660
aggagtgatg gtggatgcct gtaacccccag ctactgggga ggctgaggca ggagaatcac    48720
ttgaatccaa gaggcagaga ttgcagtgag ccgagatcat gccactgcac tgcagcctgg    48780
gtgacagagc aagactccat ctcaaaaata tatatatata taaaatttca tctcaccttc    48840
ttcccaatag tacccaccct ccctatcacc cttccttctc tgtggcacct acaacatcta    48900
actgaacaca ccatttattt atctattgtt tattcattca ttcactcatt cattcattga    48960
ctcattcatt cattcattta cttgtatgac tctcatctct agaatgcaag ctttacaaag    49020
gcagctgctg ggactacaac acctaggaca gtgtctagta catagaagat gttcggtaaa    49080
tacctgtgcc aagttgcata atatcatttg cccactgtct ttctcaagag gatttttttaa    49140 aaactataaa gcaaattctt cttttattct ttgagtgatg ttctgtgtgt gtagtaccag    49200
agaaaaagag ctggaaccac atcctctaat ctcttaattc tgaagtctgg gcctgttgct    49260
ctaaagatca ttttttcctta ataccactga gatcctcaat ttactatgag gatcatgagt    49320
ttacaactgc attgtcctgt gagggctacc tctagaaggg cttgtcgccc ctattgtgaa    49380
caaagtggac tgaagctgct gcagctgaga tacacctgca ctgaaagagg atttgtctaa    49440
gtctaaccca tgttactgtg atacaaacaa gctactgacc aaaagaggta gacgcttcct    49500
cctcagattc tgaatgaata tgctaataca tggatcctat ctcaagctac ttcttacaca    49560
gcattggctg actctgaaca gatgccttta cccatttcct ttttttttttt taatccaaaa    49620 tgtgtttatt gagatggttt cccactcatc ttgattcaga gtgctttggg tgctgcttcc    49680
tcctgaagga acatccttct gtagccttcc ttttcctcct gtaggctggc agagaacagt    49740
ggagcaggca acacacaaaa ctaccgtttg tgcatggcta cagaccatgg tgattttata    49800
gcatcctggg catgtcatat ccatgaagta ggaatcggga ctctgcacca ggcgtttctt    49860
cttctgtttc ctcttctctt ctggagaagg atgaaggaga tccctgtcga gaggcatgtt    49920
ctcgtgggta ggtcgccact gccggaaagg acccatttcc tatccttcaa gctcatctgc    49980
ccagcagcac cagcacacaa accaaagtcc aggaacactg gaagatccct actccccgca    50040
cctctccaat gaccctttt aagttcagac ctaagaagag tcacctccct aataccgcag    50100
aggctacctg ctcaccctca tctgtgtctc tgctacaaca caaactggaa tgcttttgtg    50160
tcggaatggt aagaaatgcc ttgtgtgggt ggccctccag tccccagtcc aggggatgct    50220
gagaaactgt ggggcagagt agggggacaca aacaggaaaa agcaagtttg tttctagtgt    50280
tatgctcaca gggtggcagg atatacctgc tgagcattcc cagaaggtcc ccaaggaaac    50340
cattactgta agtctctcac tttcttctct gcctgatggt tggggtgggg agagggaagg    50400
agggctatca agaggggat gggcaccctt ccagaggtca gagttatgat gcccaggaat    50460
aaaaggtgtt gaattcagga tggaatgtga aggtgaacag caaagggctt gtcaacatgg    50520
```

```
gttgtcactg gattacaccg gatggattaa ggtagggatg gggggaaggag tagaaggtga  50580
gttgggaggg aggggcttgt gtggcactga gaccccagc agggatgggg agaagggggtg  50640
ttggccacct aagcttcctg gtttgatcct tttttggctg gtttcagctg gggaagtgaa  50700
gggtcctaag gcttggatat ggagaggtgg gaatatggag aggtggggat atggagaggc  50760
ggggataagg agaggtgggg ataaggagag tggccccgca gctcccctgg tgaaccagaa  50820
tactttctca ggggttgttcc caggctggag ggagggaatt ttaggggtac gtaaggtgac  50880
tccaaggagc cttgggtgca agtactgggg gatcccagag acccagaaga tgggggtaga  50940
aaggaaggtg tttgccttca cggggagtag cctcaaaata agagggactg agggaagtca  51000
ttccaaatgc agtgggtagg tagtttaggc tcttccaatg ggatgggggtg gagcttagac  51060
ctctgcaaaa gaaggggggtc attcggaggg gacggtgcac agctgaggcg ttgggctcct  51120
aaactggaaa caggaggctc taagaggcac tgccttttcc tccagcctcg gtgtggtggg  51180
ggtggtgagt gtctggaacc gggtttcccg aatcaggaca ggagtctgaa tggatctcac  51240
aaaaaccggc cagggaggga gagaaccagg ggagactcct cacaccggga ggtgggggtg  51300
gcggcaaact gagaacccgg gcttgggggcg cgggattttc tcaacagacc ataggggtcca  51360
ctaatgtgga cggcagggat ttggggaaac taaggggggac tctcactttg gacaccaagg  51420
gctgaggacg gattggggaa gaggatacgg tttctactgg ggtgctgatg gaggttcccc  51480
actcgggacg cgaggcactg agtgggtccc ccaaactgga tatgggatcc tgggaacgga  51540
gcgagggctc taaattagag ccctgggggtg ggggtggggg gctgtaaatt aggttgggag  51600
gaaactgggg gctctgaggg cggcttctcg ctccgactgg ggaaatggag catgtgggga  51660
ctggggagca ctagggctat ctcccgcccg acccgaggag attggggttc tcttcaattc  51720
tggacagcag ggacctgaga gggaagaccg gggggggttcc cgatccggaa ccgagctacc  51780
ttgaaggcac cgggaagcgc ttcattccgg gagggcgttc ccgcggccgg ccccccgcgc  51840
cggggtgggt ggggggtgcg gccgcgccct ggtcccggcc cgcaccggga ttcggggggtc  51900
tcgctcggcc ccggagaccc aggagccccg cgggaagggg gtcccggcgc cgccgcctcc  51960
gcgggcgccc gggctcgcgg gcgagcgcgg ggctttatgc gcgcagggcg gcggggggag  52020
gagccggcag gtcggccccc ggcgggccct cccctcggcc gtccccgccc gcccgcccga  52080
gcggggtcgg gggagggggc agcatggcct gtccgtccgg cccccttcgc cgcgctcctc  52140
atctgccccg cgccgagcgc cgccgccgcc gccgccgccg ccgctccgct gcccgcgccg  52200
cccgcggctc ccgatg                                                  52216

<210> SEQ ID NO 2
<211> LENGTH: 1850
<212> TYPE: DNA
<213> ORGANISM: Homo sapiens

<400> SEQUENCE: 2
gatcctggaa ggtgggcagc aactggcaca cctcaagatg tcccttagtc tggaggtggc    60
tacatacagg tacacagtgc tgactgtcct cggcttcttc tgcggcccag aaacttggct   120
ttgtactttc tgtgactgtc agctatcgct ttgtaaaact gtcctattta tgtgtatttg   180
tgtatgtacc acatgtgtac agtgtcccta agagcccaga ggaaggcaat gggttgtgtg   240
cagctccaca ctggtgctgt gaaccaaacc cctgttctca gcaaaaagca gcaagcattc   300
ttaaccactg agccgtctgt ccagccctcg gagtcactta aaacgttttta taacatttac   360
ttatgtaatg tatttgtctg ggatggaggc ttatgagtcc cagaggtgga acaggtctgg   420
```

-continued

```
cttggcagct tggcccaccc aggttcagga ccagaagaga cggtgatgct taaaaagaca      480
gctcagtctt cagggaggag accagacaga tgagttcttt ggaaggcagg caatctccag      540
tgtctatgcc aacatcctgg ggacacctgg gcagtctcag aagagaggcc ttgcaggttt      600
gcctgatcat gctaacctgc cacctcgcct gggcctcagg tgttttgggt aagagctggc      660
ctcctagctt ttttgcttcc tttcaagccc tcatgtcact ggtcctgccc cagttctctg      720
ccctttcttt ggctgcctca ggacggctga gtggaacggc tctggtggta tgttcacagc      780
ctctgtctgt gtctcttgtg ggaaaaggcc ccagttggag tcccacggtt gagggctgag      840
gatatcactc cagagtatgg ggctaggaca ggatgccccc cttttccaga atccagcggt      900
aaagaggaaa gacagagaca ggtctaggag aggagctgga gggcccagag aaggacagcc      960
agtgagtgtc taggaaagac tgaatgcata aggcaggatg ccgcatgagg acagaggaaa     1020
gggtactttg agaaccagat gtgctcagag gccatgaatg gaaacagact agttccgaat     1080
cccatgtgaa ctgatttccc tcatctcctt caatcagctc cataggccac tgaggcaggg     1140
ccatgaacgt taagacctct gccctgaaga gtttgtgatc ctgagatgag ggctttagcc     1200
ccagtcagtc ctctgagggg aagggtccag gcagctctga ggaatgtaac cactggcgtt     1260
tgaggtctga aaaggatttg gagaaggga gctgaattca tttgcttttg tctgttacca      1320
gctctggggg cagagagaga gccatcccct gggaacagcc tgagaattcc cacttcccct     1380
gaggagccct cccttcttag gccctccaga tggtagtgtg gacaaaaggc aataattagc     1440
atgagaatcg gcctccctcc cagaggatga ggtcatcggc cttggccttg ggtggggagg     1500
cggagactga tctgaggagt ctgatataag tgttagcaat tcatttggcc ctgcctccga     1560
ctgtgggaat ctgcatgtgg ggtctccctg tgtctcaaat atgggttggc taagtatata     1620
tctgtgggta tatgactgtg tggcttttat atgacaatgg tcacaataga gattgatcct     1680
gcagtggcag gacatgctac ctcagctgga gctgaccta tctccccact ccccaccagg      1740
actctgctgg aggctgagaa ctctcggttg cagacacctg gacgaggttc ccaggcttct     1800
cttggctttc tgggtaagag gcggagccaa ctgctctcct tggaagatcc               1850
```